US006479464B1

(12) United States Patent
Haines et al.

(10) Patent No.: US 6,479,464 B1
(45) Date of Patent: Nov. 12, 2002

(54) COMPOSITIONS AND METHODS FOR HIGHLY EFFICIENT TRANSFECTION

(75) Inventors: Adrian Mark Haines, Shropshire (GB); Ross Owen Phillips, Oakwood (GB); John Hamilton Welsh, Shropshire (GB); David Robert Thatcher, Cheshire (GB); Alistair Simpson Irvine, Derbyshire (GB); Roger Kingdon Craig, Cheshire (GB)

(73) Assignee: Cobra Therapeutics Limited (GB)

( * ) Notice: Subject to any disclaimer, the term of this patent is extended or adjusted under 35 U.S.C. 154(b) by 0 days.

(21) Appl. No.: 09/023,406

(22) Filed: Feb. 12, 1998

Related U.S. Application Data

(63) Continuation-in-part of application No. 09/022,614, filed on Feb. 12, 1998, now abandoned, which is a continuation-in-part of application No. 08/861,283, filed on May 21, 1997, now abandoned, which is a continuation-in-part of application No. 08/800,079, filed as application No. PCT/GB96/01396 on Jun. 10, 1996, now abandoned, application No. 09/023,406, which is a continuation-in-part of application No. 08/861,432, filed on May 21, 1997, now abandoned.

(60) Provisional application No. 60/055,657, filed on Aug. 14, 1997.

(51) Int. Cl.$^7$ .................. A61K 48/00; C12N 15/00; C12N 15/63

(52) U.S. Cl. .............. 514/44; 435/320.1; 435/325; 435/69.1; 435/455; 435/91.4; 530/300; 530/324

(58) Field of Search ............... 435/320.1, 325, 435/455, 458; 530/300, 324; 514/44; 424/93.2, 93.21

(56) References Cited

FOREIGN PATENT DOCUMENTS

| WO | WO 94/23751 | 10/1994 |
|----|-------------|---------|
| WO | WO 96/41606 | 12/1996 |

OTHER PUBLICATIONS

Anderson, Human gene therapy, Apr. 30, 1998, Nature, vol. 392, pp. 25–30.*
Somia, Gene therapy–promises, problems and propects, Sep. 18, 1997, Nature, vol. 389, pp. 239–242.*
Chen, et al., *Human Gene Therapy* 5: 429–435 (1994).
Cotten, et al., *Methods in Enzymology* 217: 618–644 (1993).
Graham, et al., *Virology* 52:456–467 (1973).
Keown, et al., *Methods in Enzymology* 185: 527–537 (1990).
Kucherlapati and Skoultchi, *CRC Critical Reviews in Biochemistry* 16: 349–378 (1984).
Machy et al., *Proc. Natl. Acad. Sci.* 85: 8027–8031 (1988).
Mack et al., *The American Journal of the Medical Sciences* 307: 138–143 (1994).
Midoux, et al., *Nucleic Acids Research* 21: 871–878 (1993).
Plank, et al., *The Journal of Biological Chemistry* 269: 12918–12924 (1994).
Rosenkranz et al., *Experimental Cell Research* 199: 323–329, 1992.

(List continued on next page.)

*Primary Examiner*—Dave T. Nguyen
(74) *Attorney, Agent, or Firm*—Woodcock Washburn LLP

(57) ABSTRACT

The invention encompasses a transfection complex comprising a polypeptide comprising the contiguous 29 amino acids: 6G's, 2F's, 2L's, 1W, 4R's, 2E's, 2N's, 3K's, 1T, 1S, 1A, 1Y, 1M, 1C, and 1I, and having additional cationic residues to provide a net number of positive charges of equal to or greater than 8, and an isolated nucleic acid, and methods of transfecting cells using this transfection complex. The invention also includes a polypeptide having an amino acid composition including these 29 amino acids, as well as mixtures of polypeptides in which this polypeptide is present.

31 Claims, 48 Drawing Sheets

PCS analysis Results

1) Effect of CL22:DNA ratio on complex size in HEPES

CL22 batch RDH/224/42 (ratio by E280), DNA pCMVB batch SW/202/145

OTHER PUBLICATIONS

Trubetskoy, et al., *Bioconjugate Chemistry* 3: 323–327 (1992).

Wigler, et al., *Cell* 16:777–785 (1979).

Wu et al., *The Journal of Biological Chemistry* 262: 4429–4432, 1987.

Wu et al., *The Journal of Biological Chemistry* 266: 14338–14342, 1991.

Wadhwa et al., Peptide–Mediated Gene Delivery: Influence of Peptide Structure on Gene Expression, *Bioconjugate Chemistry*, (1997), 8(1), 81–88.

* cited by examiner

PCS analysis Results

1) Effect of CL22:DNA ratio on complex size in HEPES

CL22 batch RDH/224/42 (ratio by E280), DNA pCMVβ batch SW/202/145

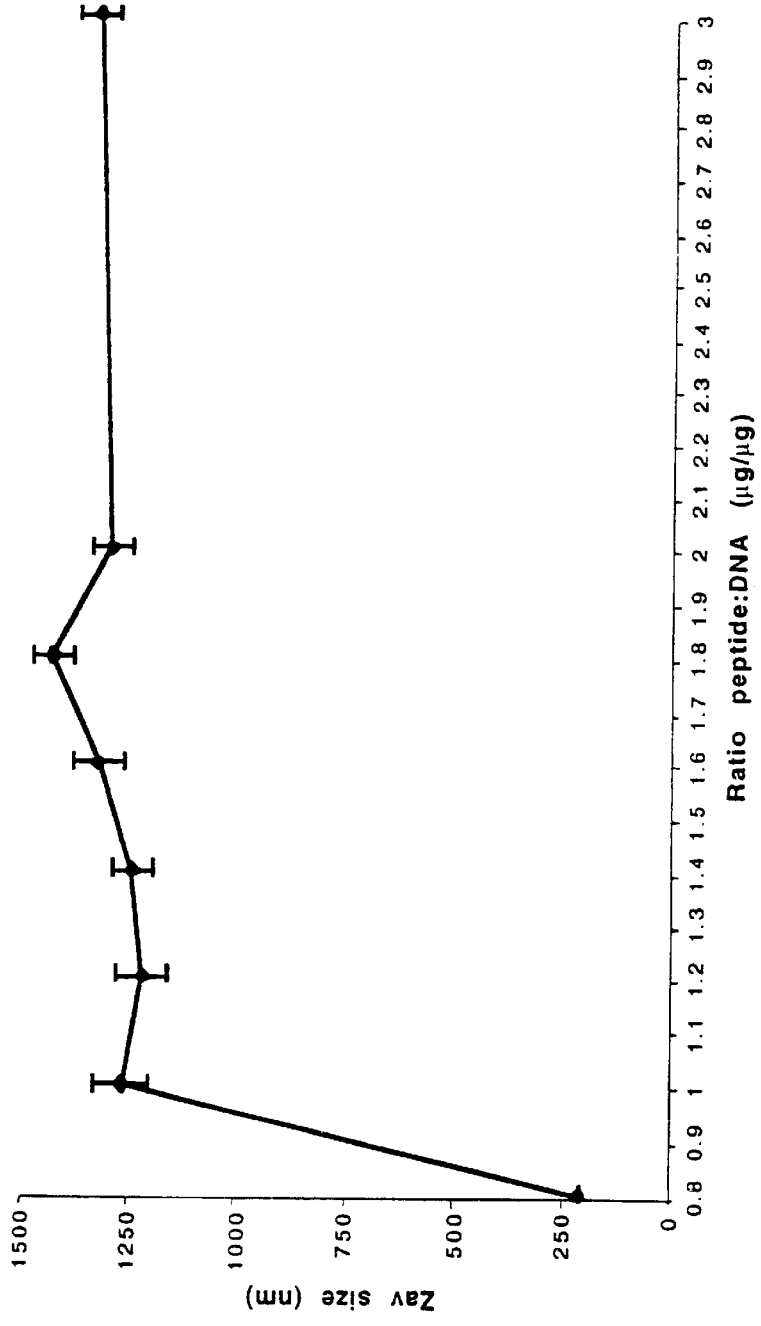

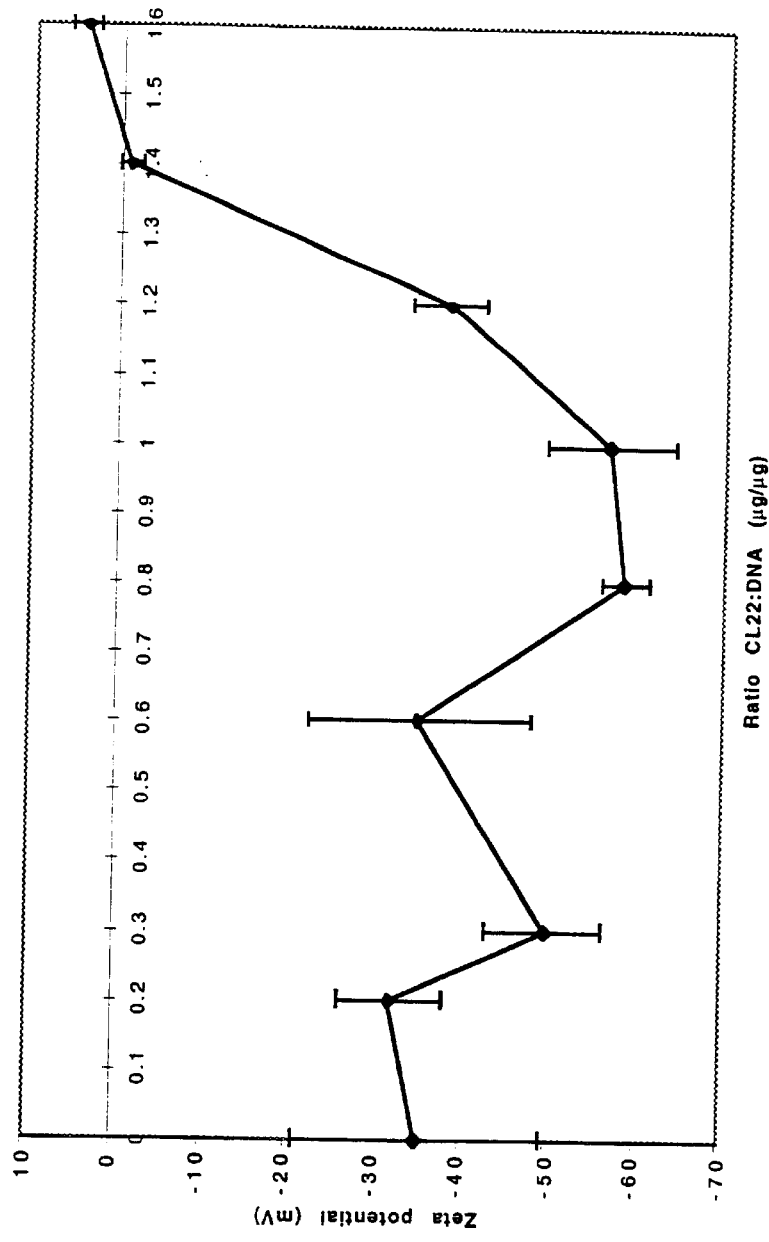

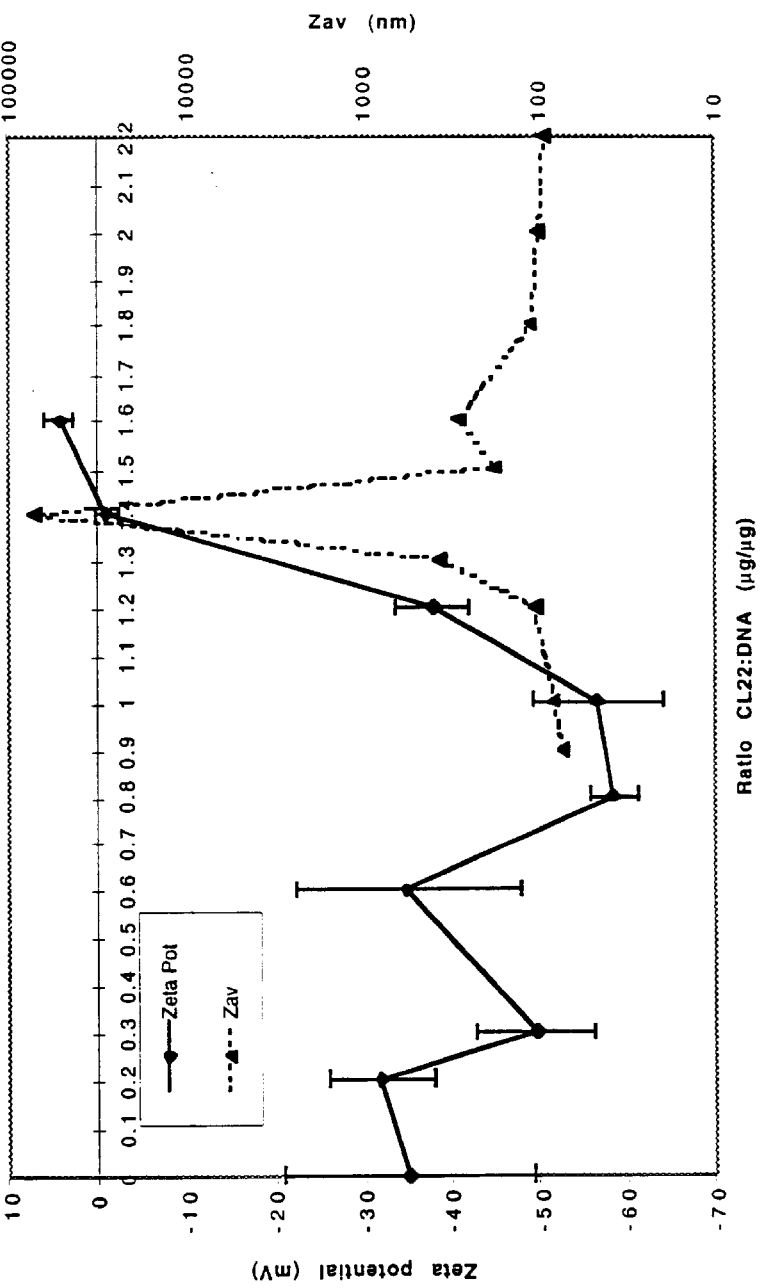

| | lum units | mg prot | lum/mg | Av (x10-6) | St. Error (x10-6) |
|---|---|---|---|---|---|
| NAKED DNA | 4623 | 0.877 | 5271.4 | 0.01 | 0.00 |
| | 4449 | 0.871 | 5107.9 | | |
| | 4526 | 0.84 | 5388.1 | | |
| K6CIII + DNA | 52408000 | 0.492 | 106520325.2 | 103.88 | 8.49 |
| | 45337400 | 0.515 | 88033786.4 | | |
| | 68721100 | 0.587 | 117071720.6 | | |

FIG. 10 Investigation of CL22:DNA ratios for transfection of two DC preparations FIG. 11 Effect of transfection time on number of transfected cells with 40 μM CQ and 2 μg/μg CL22 complexes FIG. 12 Effect of transfection time on number of transfected cells with 80 µM CQ and 2 µg/µg CL22 complexes Effect of transfection time on transfection efficiency with 20 μM chloroquine and 2μg/μg CL22 complexes

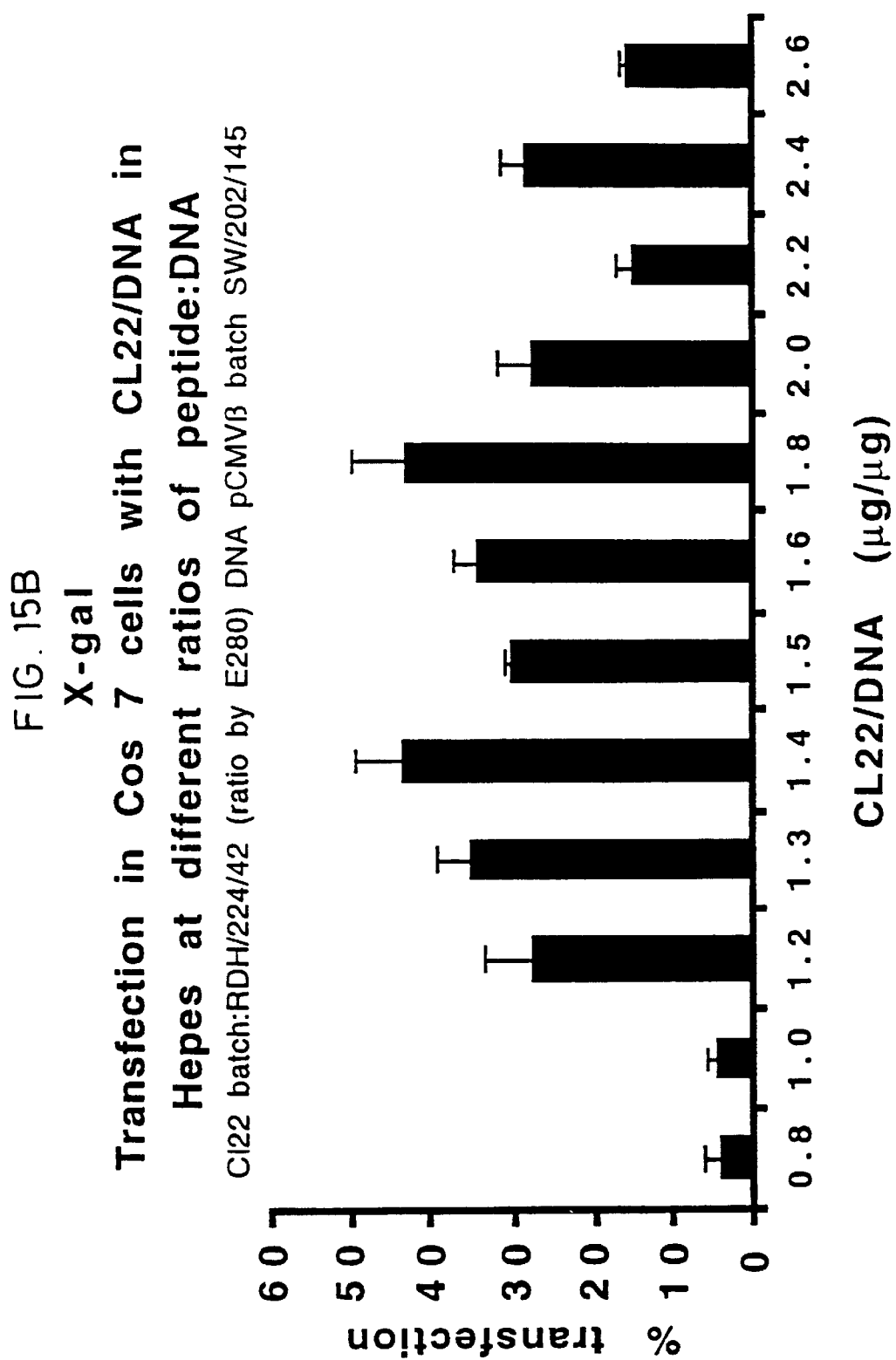

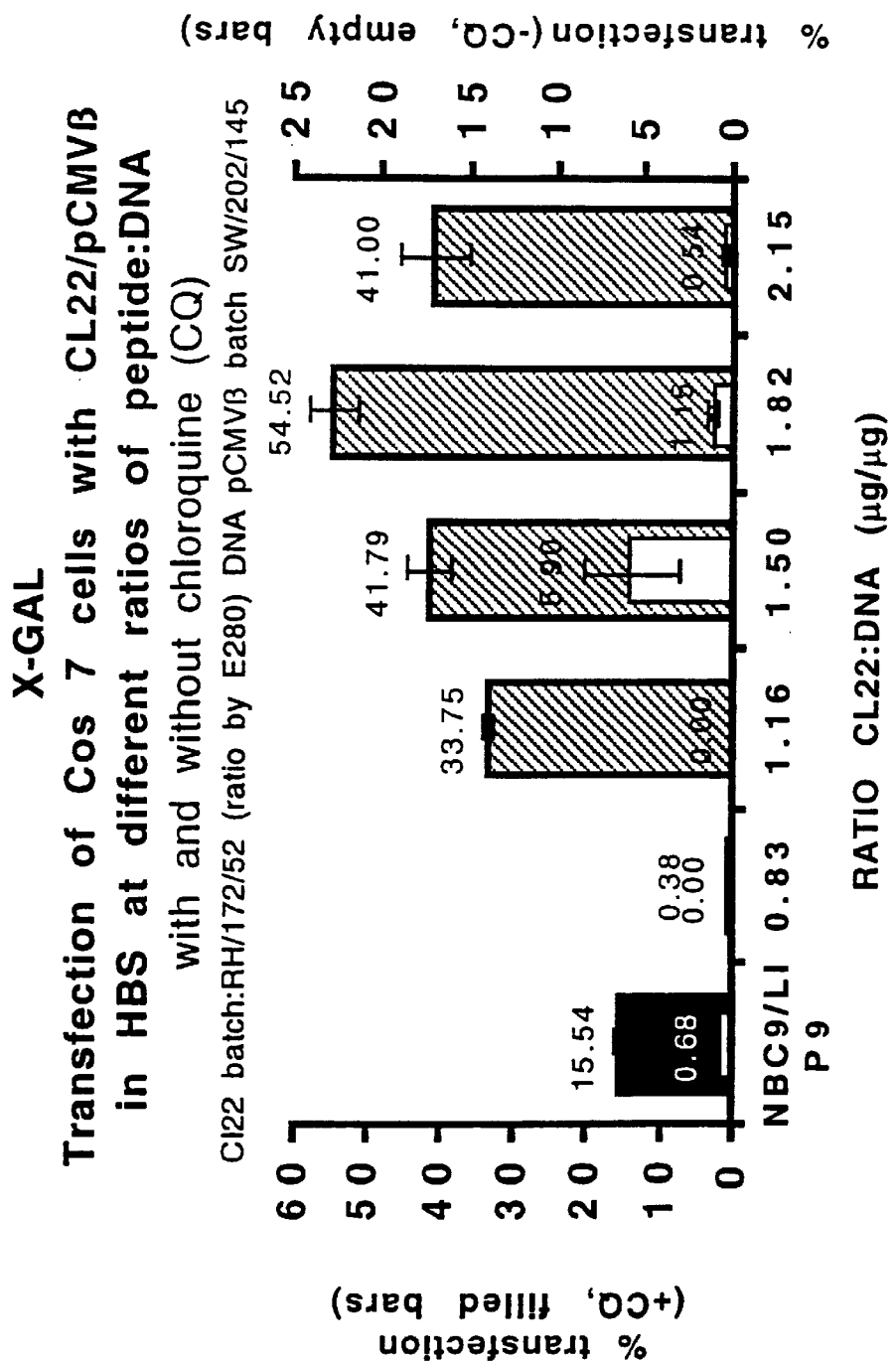

Transfection with LIC-CL22/DNA prepared in HEPES buffer and HBS

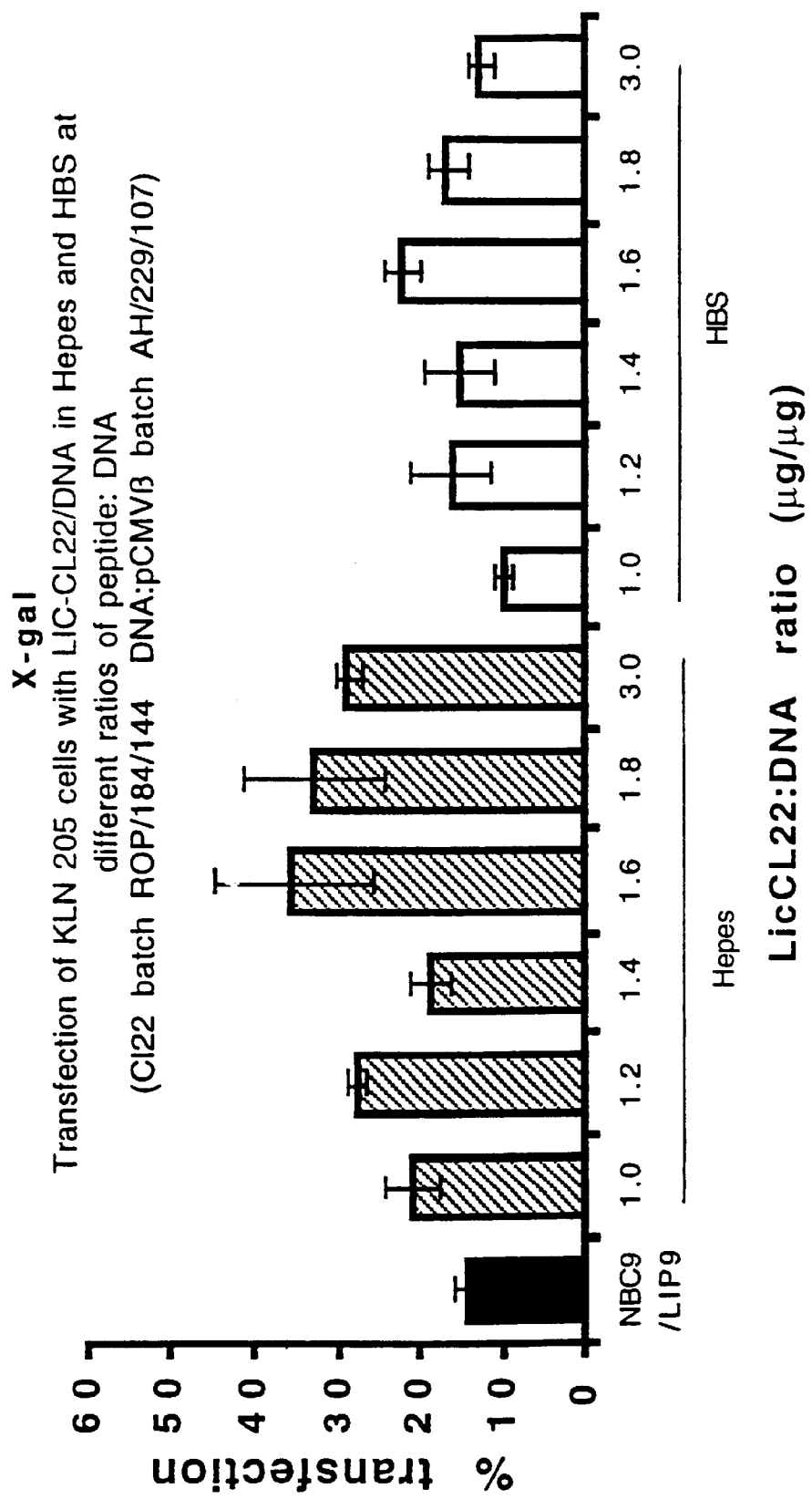

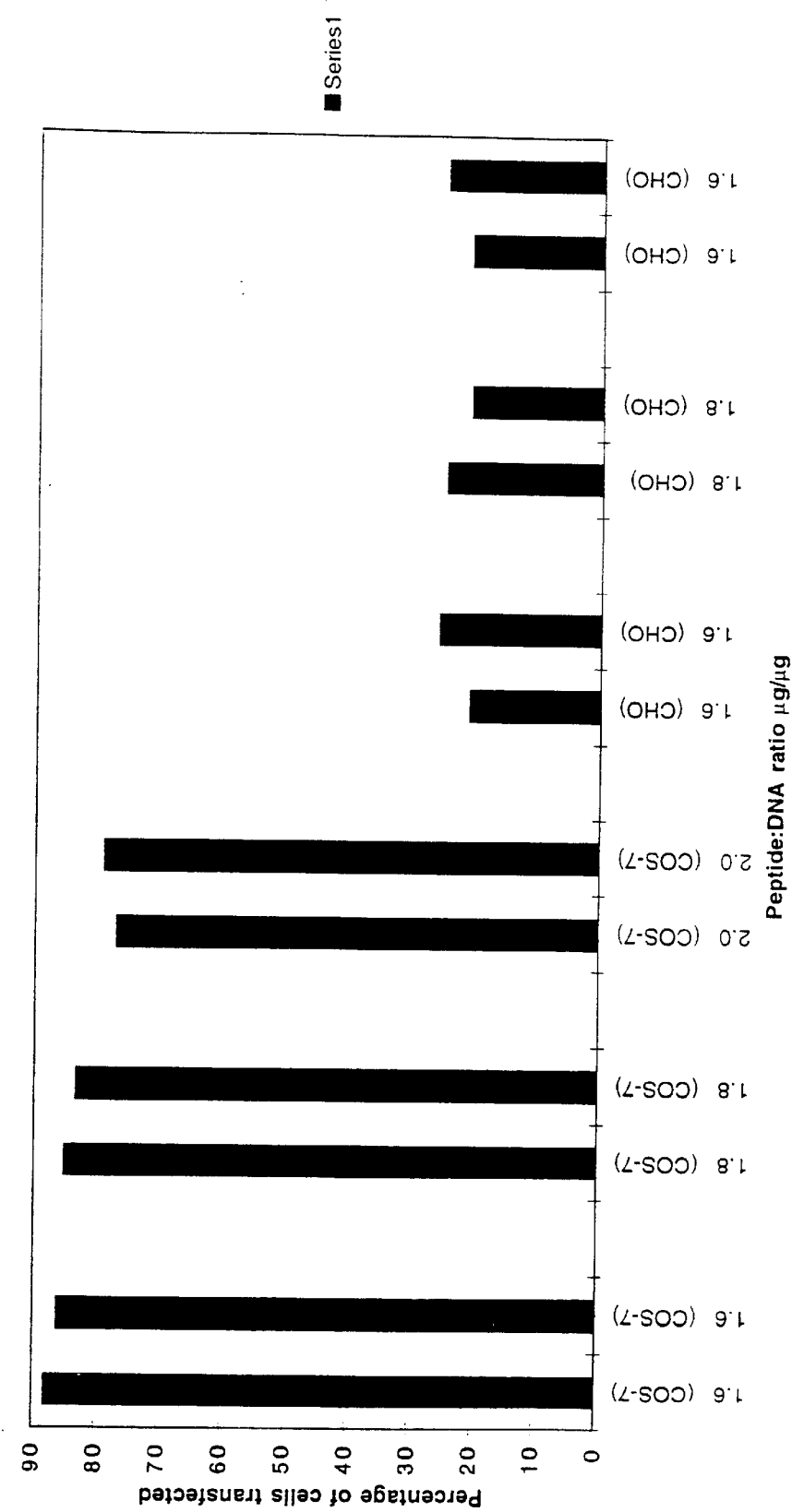

Comparison of DC transfection with CL22-based gene complexes, Lipofectin (Gibco-BRL) and SuperFect (Qiagen)

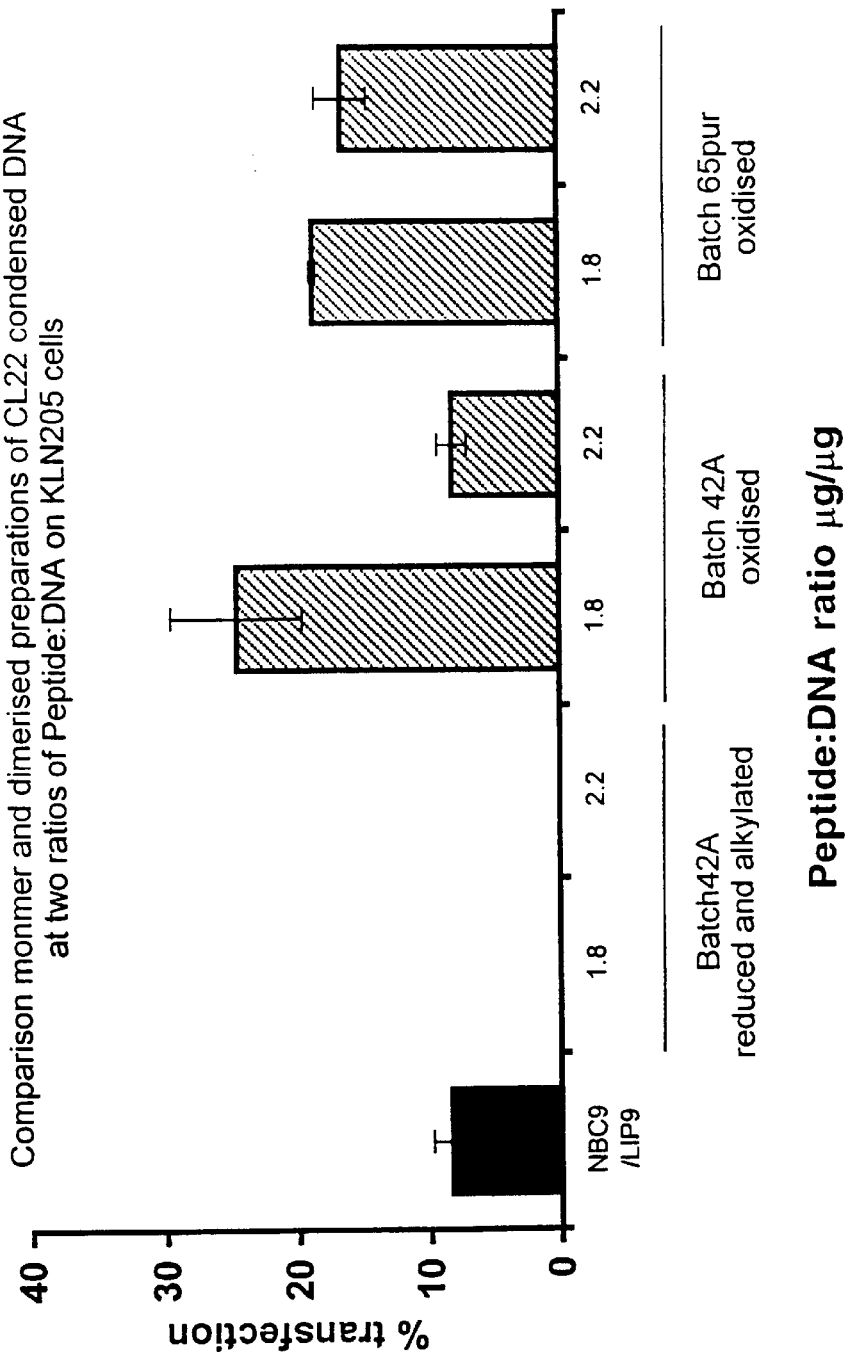

SAMPLE DETAILS:
M) MARKER PROTEINS (NOVEX)
A) REDUCED AND BLOCKED CL22 BATCH 42A
B) OXIDISED CL22 BATCH 42A
C) OXIDISED CL22 BATCH 65PUR

= polylysine sequence

FIG. 23 Effect of CL28(ox):pCMVβ on particle size and ZETA potential after overnight incubation in 10mM HEPES pH 7.4

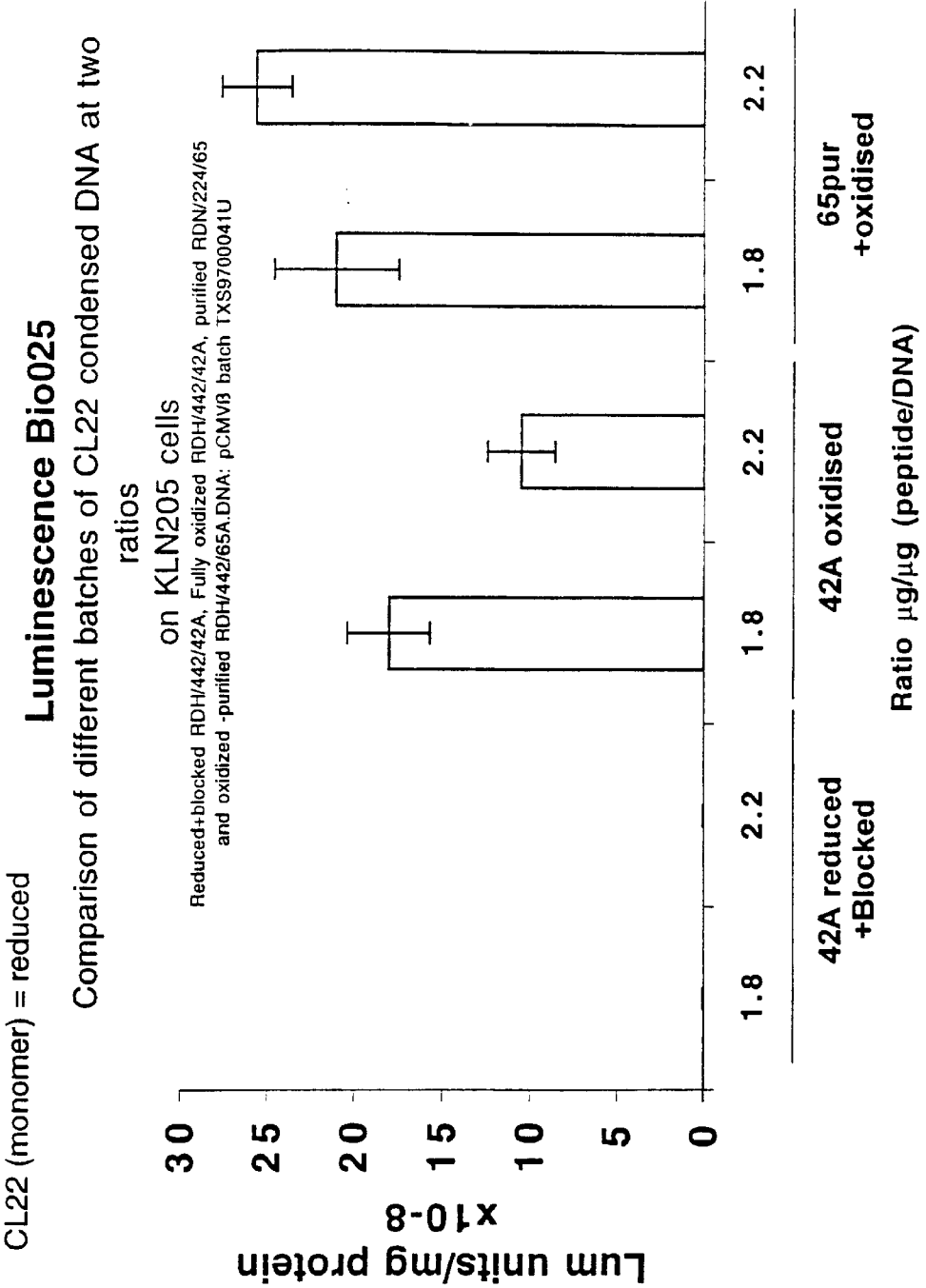

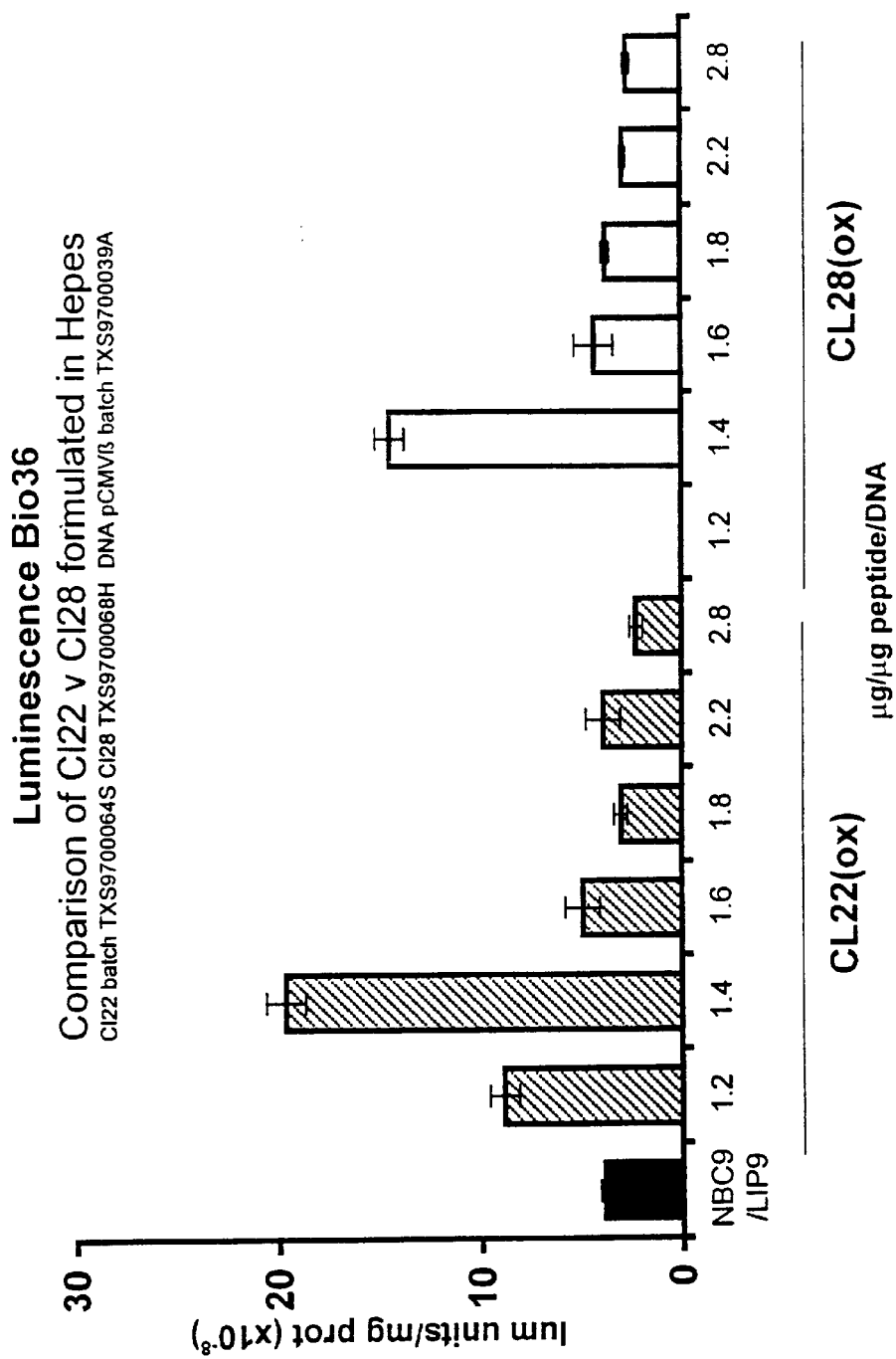

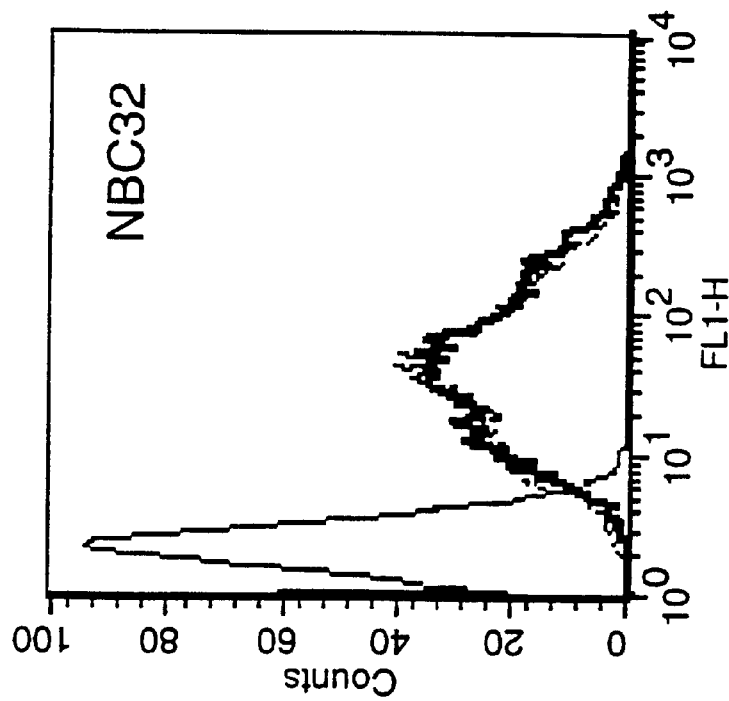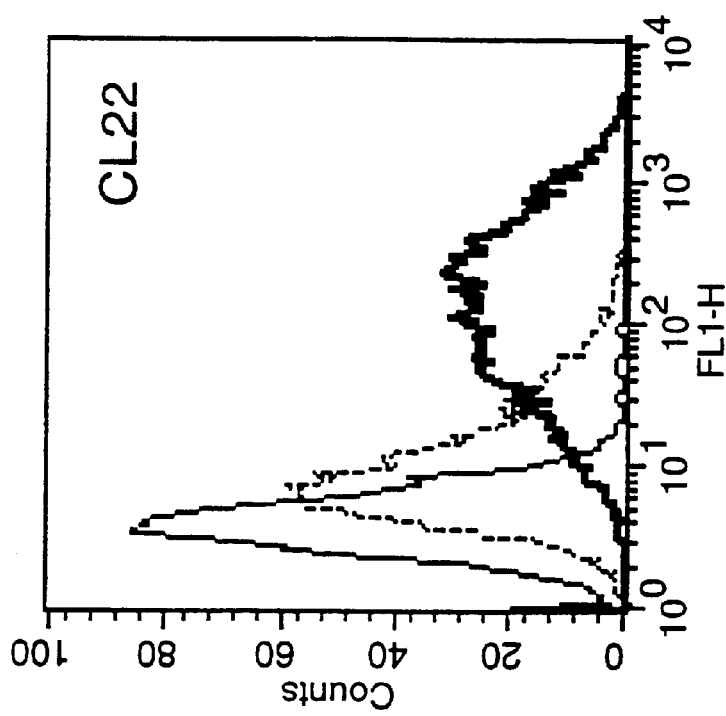
FIG. 30

Luminescence (Bio251)
Comparison of two FGF conjugates on BHK21 cells

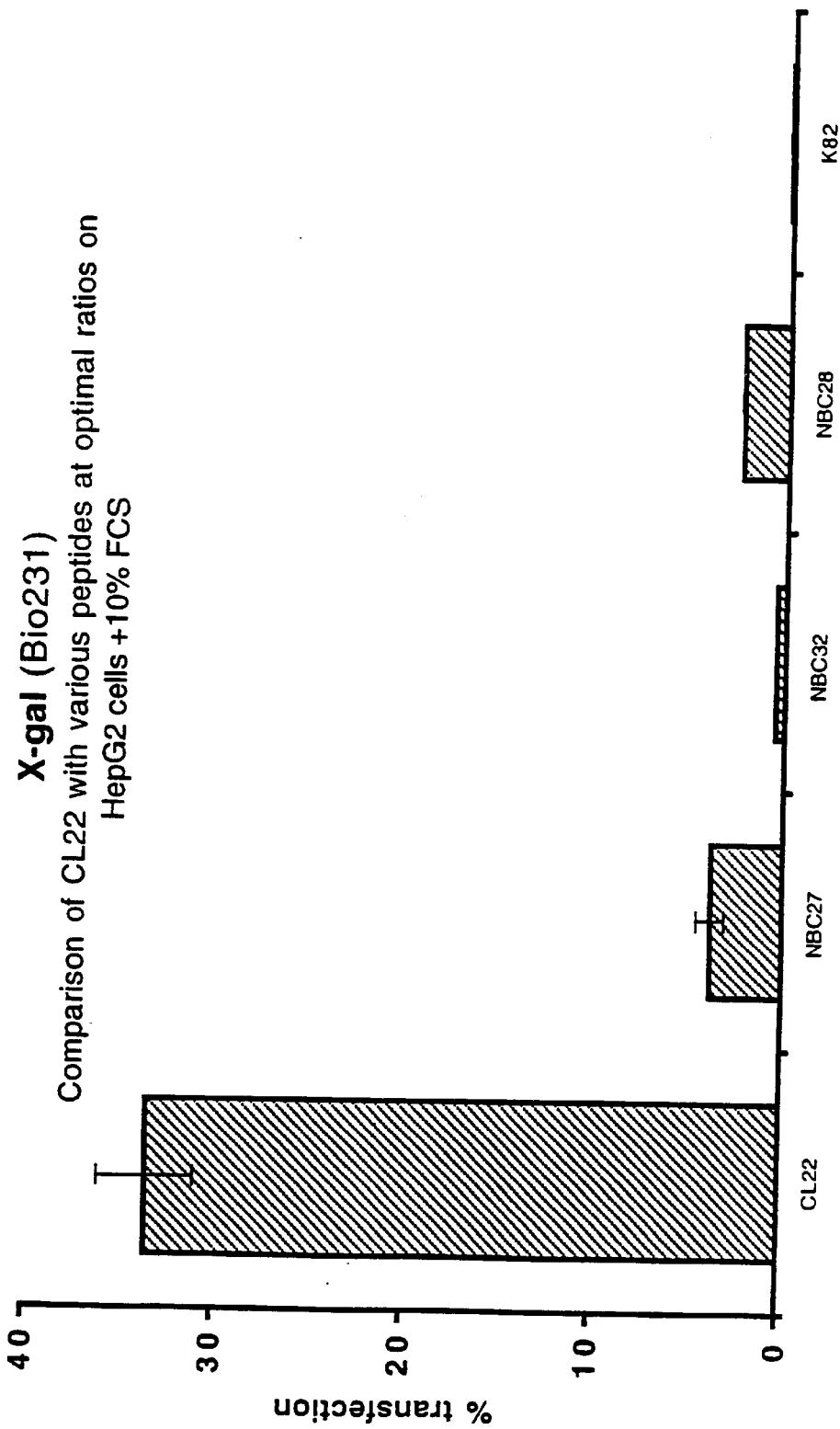

Comparison of Transfection of DC with CL22 and CL26

FIG. 34 Comparison of Transfection of DC with CL22 and CL26

Transfection of DC with CL22 and CL26

Transfection Efficiencies of different CL22 Batches

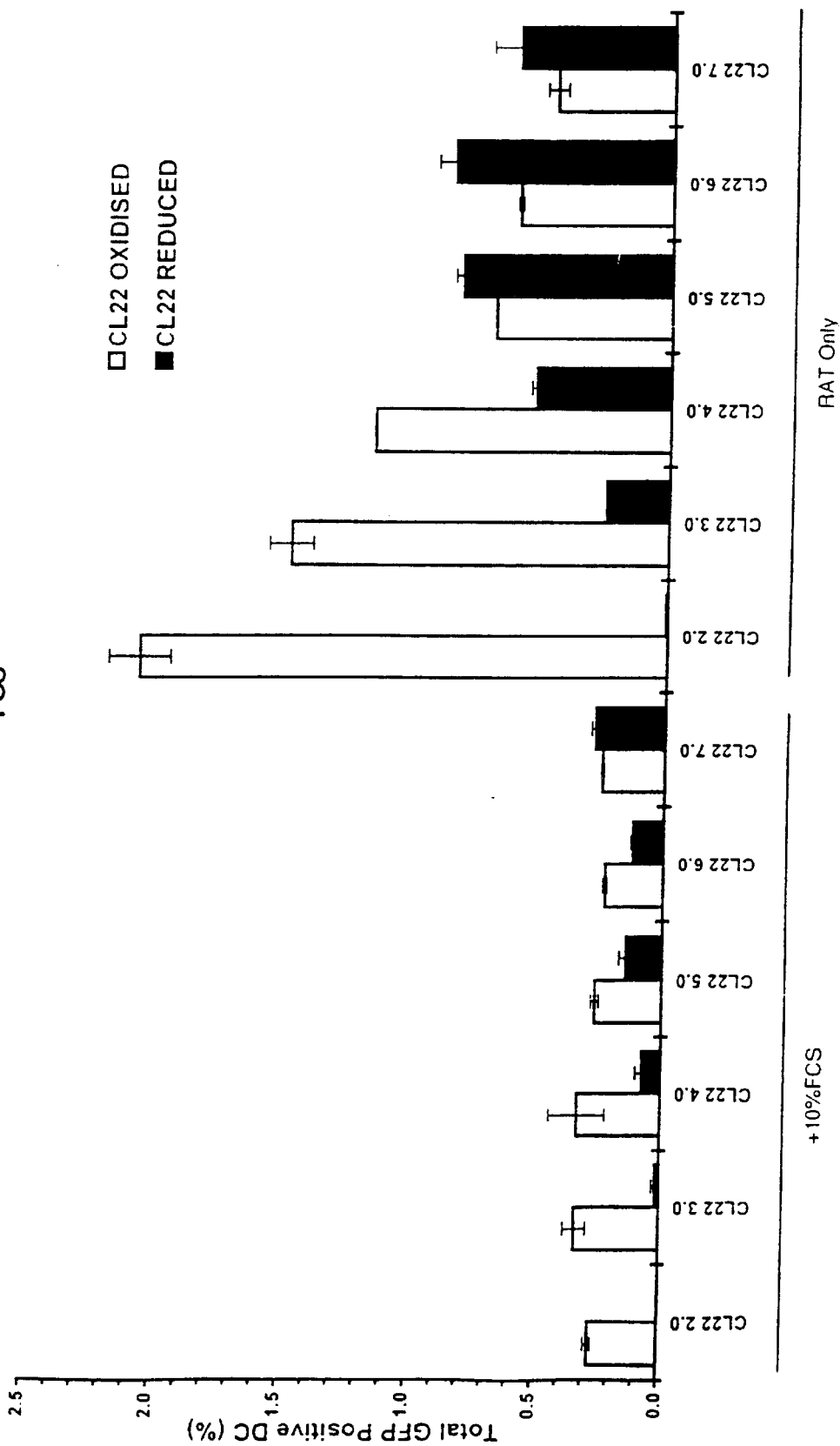

COMPOSITIONS AND METHODS FOR HIGHLY EFFICIENT TRANSFECTION

This application is a cotinuation in part of U.S. application Ser. No. 09/022,614, filed Feb. 12, 1998, now abandoned, which is a contiuation in part of U.S. application Ser. No. 08/861,283, filed May 21, 1997, now abandoned, which is a continuation in part of U.S. application Ser. No. 08/800,079, filed Feb. 12, 1997, now abandoned, which claims the benefit of Great Britain Application No. 9602777.6, filed Feb. 12, 1996 and Great Britain application No. 9614548.7, filed Jul. 11, 1996. This application is also a continuation in part of U.S. application Ser. No. 08/861,432, filed May 21, 1997, now abandoned.

FIELD OF THE INVENTION

The invention relates in general to transfection of cells and to agents which condense nucleic acid.

BACKGROUND OF THE INVENTION

Cell transfection relies on efficient delivery of DNA to target cells, and expression of the delivered DNA in the nucleus of such cells.

Early experiments on introducing DNA into mammalian cells in vitro utilized DNA in precipitated form with low efficiency of transfection and required selectable marker genes (Wigler et al. (1977) Cell 16:777–85; Graham and Van der Eb (1979) Proc. Natl. Acad. Sci. USA 77:1373–76 and (1973) Virology 52:456)). Since this time molecular biologists have developed many other more efficient techniques for introducing DNA into cells, such as electroporation, complexation with asbestos, polybrene, DEAE, Dextran, liposomes, lipopolyamines, polyornithine, particle bombardment and direct microinjection (reviewed by Kucherlapati and Skoultchi (1984) Crit. Rev. Biochem. 16:349–79; Keown et al. (1990) Methods Enzymol. 185:527). Many of these methods are unsuitable for use clinically since they give highly variable and relatively poor levels of transfection. Another obstacle to the wider use of existing transfection complexes resides in their instability in vivo. It has been shown that particles of a similar size to the transfection complexes of the prior art are rapidly and efficiently removed from the blood by the reticuloendothelial system (Poste and Kirsch, Bio/Technology 1:869 (1984)).

Soluble DNA/polylysine complexes have been generated (Li et al., (1973) Biochem. J. 12:1763) and tagged with asialoglycoprotein to target DNA to hepatocytes in vitro (Wu and Wu, J. Biol. Chem. 262:4429 (1987); U.S. Pat. No. 5,166,320). Lactosylated polylysine (Midoux et al. (1993) Nuc. Acids Res. 21:871–878) and galactosylated histones (Chen et al. (1994) Human Gene Therapy 5:429–435) have been used to target plasmid DNA to cells bearing lectin receptors, and insulin conjugated to polylysine (Rosenkrantz et al. (1992) Exp. Cell Res. 199:323–329) to cells bearing insulin receptors. However, Wagner et al. (supra) have shown that the latter approach is even less efficient than standard methods of transfection, and may therefore be considered unsuitable for pharmaceutical-development. Monoclonal antibodies have been used to target DNA to particular cell types (Machy et al. (1988) Proc. Natl. Acad. Sci. USA 85:8027–8031; Trubetskoy et al. (1992) Bioconjugate Chem. 3:323–27 and WO 91/17773 and WO 92/19287).

Peptides derived from the amino acid sequences of viral envelope proteins have been used in gene transfer when coadministered with polylysine DNA complexes (Plank et al. (1994) J. Biol. Chem. 269:12918–24). Trubetskoy et al. (supra) and Mack et al. ((1994) Am. J. Med. Sci. 307:138–143) suggest that cocondensation of polylysine conjugates with cationic lipids can lead to improvement in gene transfer efficiency. WO 95/02698 discloses the use of viral components to attempt to increase the efficiency of cationic lipid gene transfer.

Disulfide bonds have been used to link the peptidic components of a delivery vehicle (Cotten et al. (1992) Meth. Enzymol. 217:618–644); see also, Trubetskoy et al. (supra) However, the chemical modification of the various components, although group specific, is not regio-specific and leads to enormous molecular heterogeneity of the conjugated product. Disulfide bonds are also known to be unstable in biological fluids and thus limits the potency of such compounds in practice.

Similar heterogeneity is also produced by other standard conjugation methods such as carbodiimide coupling through side chain carboxyl groups (Wu et al. (1991) J. Biol. Chem. 266:14338–42). However, in addition to the above disadvantages, the resulting amide bond coupling the components is chemically stable within the cytosol and makes the components difficult to separate.

More specific coupling chemistry has been employed by Cotten et al. (supra). This method involves oxidation of the carbohydrate moieties using periodate, followed by subsequent reaction with polylysine. The Schiff base so formed was reduced with sodium cyanoborohydride to form a stable amide bond. However, due to the large number of available lysine residues, the resulting amide bond was linked at random to the polylysine component.

Trubetskoy (supra) observed increased efficiency of a conjugate made up of a heterogeneous polylysine moiety linked through the N-terminus non-specifically to amino functions on a monoclonal antibody.

Many prior art methods employ highly heterogeneous components linked by conjugation chemistry which itself leads to more heterogeneity. This heterogeneity leads to poor control during preparation and large batch-to-batch variability, low potency and poor solution stability.

Scale up and reproducible manufacture of the gene delivery vehicles described in the literature are problematic because of the extreme heterogeneity of the products and components of those systems. Key parameters such as quality control, process control and product identification are thus rendered imprecise. Therefore, an object of the invention is the development of a reproducible and scalable production process for pharmaceutical compositions which facilitate delivery of exogenous DNA to a target cell with high efficiency.

Another object of the invention is to provide an improved transfection complex having chemical components of defined stoichiometry and therefore reduced heterogeneity.

Yet another object of the invention is to provide pharmaceutical formulations for transfection which exhibit increased transfection efficiency.

SUMMARY OF THE INVENTION

The invention is based on the discovery of polypeptides which, when associated with a nucleic acid, confer a high efficiency upon host cell transfection.

The invention encompasses a polypeptide comprising or consisting of the following 29 amino acid composition: 6G's, 2F's, 2L's, 1W, 4R's, 2E's, 2N's, 3K's, 1T, 1S, 1A, 1Y, 1M, 1C, and 1I, and having additional cationic residues to provide a net number of positive charges of greater than 8. Preferably, the 29 amino acids are contiguous.

As used herein, "composition" refers to the amino acid content rather than an order of amino acids. "Cationic residue" refers to an amino acid or other molecule having a net positive charge, examples of which include but are not limited to lysine, ethyleneimine, arginine, methacrylate, amidoamine, protamine, spermine, and spermidine. "Cationic charge" refers to a net positive charge.

As the 29 amino acids specified above contained in the polypeptide contain 7 cationic residues and 2 anionic residues, and thus contain a net of 5 cationic charges, the additional cationic charges will number at least 3, preferably, 4 or 5 and more preferably number, for example, 6, 12, 18 or 24.

Polypeptides according to the invention will therefore contain the 29 amino acids specified above and additional cationic residues sufficient to net equal to or greater than 8 positively charged residues in the polypeptide, wherein the 29 amino acids specified above may be present in the polypeptide as (a) a block of: 29 contiguous amino acids and equal to or greater than ($\geq$) 3 cationic residues (monomer) or (b) as two or more blocks of the 29+$\geq$3 amino acids (dimer, trimer, etc., i.e., multimer). Where a 29+$\geq$3 polypeptide is present in a multimeric form, several individual 29+$\geq$3 polypeptides may be linked in conventional stable bonds (peptide, oxime, or thioether) or the polypeptides may be linked via labile bonds, e.g., disulfide bonds.

A cationic sequence useful herein may be a tract of contiguous cationic residues in the length range of 3 to 700, whereby the net cationic charge is at least 3. Alternatively, the tract of cationic sequences need not be contiguous, but may be dispersed among basic or neutral amino acids such that the net number of cationic charges is in the range of 3 to 700. Therefore, a polypeptide according to the invention may contain as few as (5+3=)8 net cationic charges or as many as (5+700=)705 net cationic charges. A given cationic sequence may be linked in conventional stable bonds at either the amino or carboxy terminus of the 29 amino acid tract specified above, or at both ends, or within the 29 amino acid tract. If cationic sequences are present at both ends of the 29 amino acid tract, then each end may contain a different number of cationic residues or an identical number of cationic residues. Alternatively, the cationic sequence may be bonded to the 29 amino acid tract at one or more position along its length via a labile (sulfhydryl) or a stable bond. Finally, the 29 amino acid tract may be linked to a cationic sequence at one or more position along the length of the cationic sequence via a labile or stable bond.

The invention also encompasses a polypeptide comprising the amino acid sequence, from amino to carboxy termini, NH2-KKKKKKGGFLGFWRGENGRKTRSAYERMC NILKGK-COOH (SEQ ID NO:1) (also referred to herein as K6CL22, K6CLII, CL22 or CLII).

The invention also encompasses a polypeptide comprising the amino acid sequence, from amino to carboxy termini,

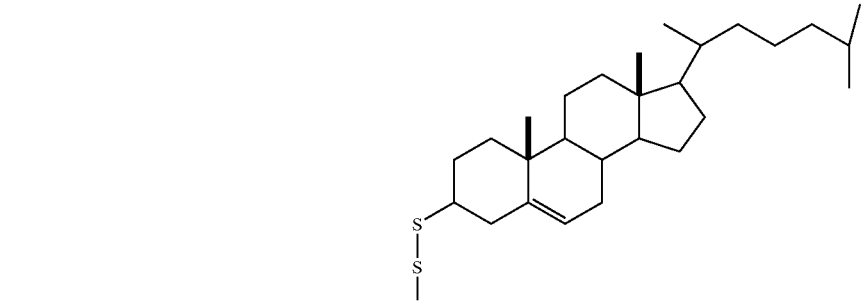

NH2-KKKKKKGGFLGFWRGENGRKTRSAYERMCNILKGK-COOH
(SEQ ID NO: 1)(also referred to herein as licK6CL22 or licK6CLII).

Preferably, the above-polypeptides consists essentially of the above-recited sequences.

The invention also encompasses a transfection complex comprising a polypeptide comprising the amino acid sequence, from amino to carboxy termini, NH2-KKKKKKGGFLGFWRGENGRKTRSAYERMC NILKGK-COOH (SEQ ID NO:1), and an isolated nucleic acid.

The invention also encompasses a transfection complex comprising a polypeptide comprising the amino acid sequence, from amino to carboxy termini,

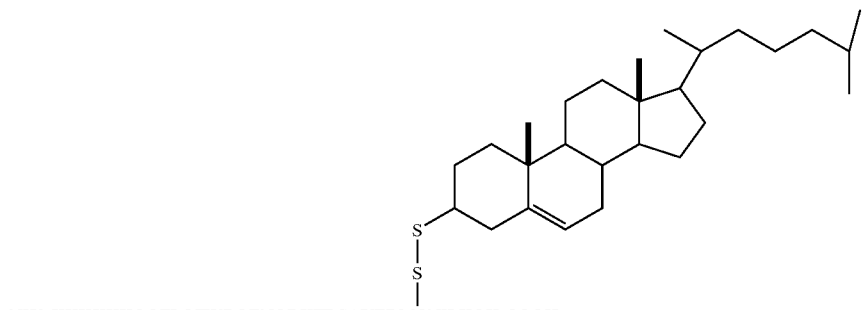

NH2-KKKKKKGGFLGFWRGENGRKTRSAYERMCNILKGK-COOH
(SEQ ID NO: 1), and an isolated nucleic acid.

The invention also encompasses a dimerized K6CL22 polypeptide comprising the amino acid sequence, from amino to carboxy termini, NH2-KKKKKKGGFLGFWRGENGRKTRSAYERMCNILKGK-COOH (SEQ ID NO: 1)
NH2-KKKKKKGGFLGFWRGENGRKTRSAYERMCNILKGK-COOH (SEQ ID NO: 1)

wherein S—S refers to a cystine linkage (disulfide bond) between each cysteine residue of the two peptides.

The invention also encompasses a polypeptide comprising the following amino acid sequence from amino to carboxy terminus:

H-KKKKKKGGFLGFNTKERNLKRGWEICRSAMGYGRK-OH (SEQ ID NO:2) (CL28).

The invention also encompasses a polypeptide comprising the following amino acid sequence from amino to carboxy terminus:

H-KKKKKKKKKKKKGGFLGFWRGENGRKTRSAYERMCNILKGK-OH (SEQ ID NO:3) (CL26).

The invention also encompasses a dimerized CL26 polypeptide comprising the following amino acid sequence from amino to carboxy terminus:

The invention also encompasses a transfection complex comprising a mixture of polypeptides of two or more different amino acid sequences, wherein the mixture of polypeptides includes as one of the polypeptides of the mixture any one of the polypeptides (monomers or multimers) described above. For example, one polypeptide of the mixture is the polypeptide having the sequence NH2-KKKKKKGGFLGFWRGENGRKTRSAYERMCNILKGK-COOH (SEQ ID NO: 1), and an isolated nucleic acid.

Another example of a transfection complex according to the invention comprising a mixture of polypeptides of two or more different amino acid sequences, wherein the mixture of polypeptides includes as one of the polypeptides of the mixture the polypeptide having the sequence H-KKKKKKKKKKKKGGFLGFWRGENGRKTRSAYERMCNILKGK-OH (SEQ ID NO: 3)
H-KKKKKKKKKKKKGGFLGFWRGENGRKTRSAYERMCNILKGK-OH (SEQ ID NO: 3)

wherein S—S refers to a disulfide bond between each cysteine residue of the two polypeptides.

The invention also encompasses the polypeptide referred to herein as NBC30, comprising the following:

H-WKKKKKKKKKKKKKKKKKKKCG-OH (SEQ ID NO: 4)(NBC26)
H-KKKKKKGGFLGFWRGENGRKTRSAYERMCNILKGK-OH (SEQ ID NO: 4)(K6CL22)

wherein S—S refers to a disulfide bond between each cysteine residue of the two polypeptides.

As used herein, the term "transfection complex" refers to a mixture of a peptide according to the invention and a nucleic acid which is preferably DNA but which also may be RNA, the nucleic acid of which is condensed.

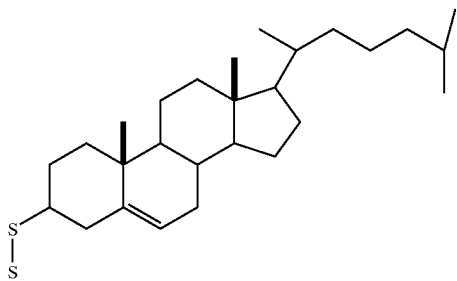

NH2-KKKKKKGGFLGFWRGENGRKTRSAYERMCNILKGK-COOH
(SEQ ID NO: 1), and an isolated nucleic acid.

As used herein, the phrase "different amino acid sequences" refers to a sequence that differs from one of the above described amino acid sequences at one or more residues, or that differs from this sequence in length by one or more residues.

It is preferred that the polypeptide and nucleic acid are associated such that said nucleic acid is condensed.

The invention also encompasses a pharmaceutical formulation for taansfection of cells, comprising an amino acid sequence as described above, an isolated nucleic acid, and a pharmaceutically acceptable diluent.

Preferably, the polypeptide and said nucleic acid are associated such that said nucleic acid is condensed.

The invention also encompasses host cells containing the polypeptide or the transfection complex described herein, and methods of transfection.

The transfection methods encompassed by the invention include wherein a host cell is contacted with the transfection complex, or the pharmaceutical formulation containing the transfection complex.

Although the host cell may be any type or species of cell, it is preferred that the host cell is a eukaryotic cell, such as a mammalian cell, including cells that are human, mouse, monkey, hamster, and the like. Cell types transfectable according to the invention include somatic cells, including primary cells as well as cell lines, such as dendritic cells, tumor cells, fibroblasts, muscle cells, and germline cells, such as ovarian cells.

The methods also include introducing a nucleic acid into a host cell in vivo by administering to a patient a transfection complex or a pharmaceutical formulation according to the invention.

The methods also contemplate improvements over known methods of delivering a nucleic acid to a cell wherein a nucleic acid delivery complex is administered to a patient, the improvement comprising wherein the delivery complex comprises a nucleic acid and a polypeptide mixture which includes as one of the polypeptides of the mixture the polypeptide having the composition or sequences described herein.

The invention also contemplates a method of preparing a transfection complex, comprising contacting the a polypeptide according to the invention, or a mixture of polypeptides containing this polypeptide, with a nucleic acid under conditions which permit the condensation of the nucleic acid and the association of the polypeptide and the condensed nucleic acid in a particle.

Further features and advantages of the invention will become more fully apparent in the following description of the embodiments and drawings thereof, and from the claims.

BRIEF DESCRIPTION OF DRAWINGS

The drawings are briefly described.

FIG. 2 is a graph which shows that in the presence of 150 mM NaCl large particles/aggregates of complex of approx. 1000 nm are formed after one hour.

FIG. 3 is a graph of zeta potential results for different ratios of peptide:DNA.

FIG. 4 is a graph which indicates that as the peptide:DNA ratio is increased the zeta potential of the complex becomes less negative.

FIG. 7a presents data for triplicate transfections of Cos cells with naked DNA or K6CL22 and DNA transfection complexes. The values provided are: luminescence units read from a luminometer (1 um units); the amount of protein found in the sample (mg); luminescence units per mg protein (1 um/mg); average luminescence units per mg of protein each condition (Av); standard error (St. Error).

FIG. 7b is a bar graph of the data presented in FIG. 7a.

FIG. 15b shows luminescence and X-gal results of Cos7 cell transfection at different K6CL22/DNA ratios.

FIG. 16b shows luminescence and X-gal results of Cos7 cell transfection at different K6CL22/DNA ratios.

FIG. 18 shows transfection results in which CL22/DNA (pCMVβ) was used to transfect Cos 7 cells or CHO cells, as indicated, in the presence of 120 μM chloroquine.

FIGS. 20A and 20B present a comparison of transfection efficiencies using DNA transfection complexes containing the reduced or oxidized form of the CL22 peptide.

FIGS. 25A and 25B are bar graphs of transfection efficiencies for CL22 monomer and dimer transfection complexes.

FIGS. 27A and 27B are bar graphs of transfection efficiencies of CL22 dimer (d) and CL28 dimer (d) transfection complexes.

FIG. 30 represents a FACScan analyses measuring uptake of K6CL22/DNA and NBC 32/DNA transfection complexes by KLN 205 cells.

FIG. 37 is a bar graph of transfection efficiency for CL22 monomer and dimer in dendritic cells.

DESCRIPTION

Figure 1:
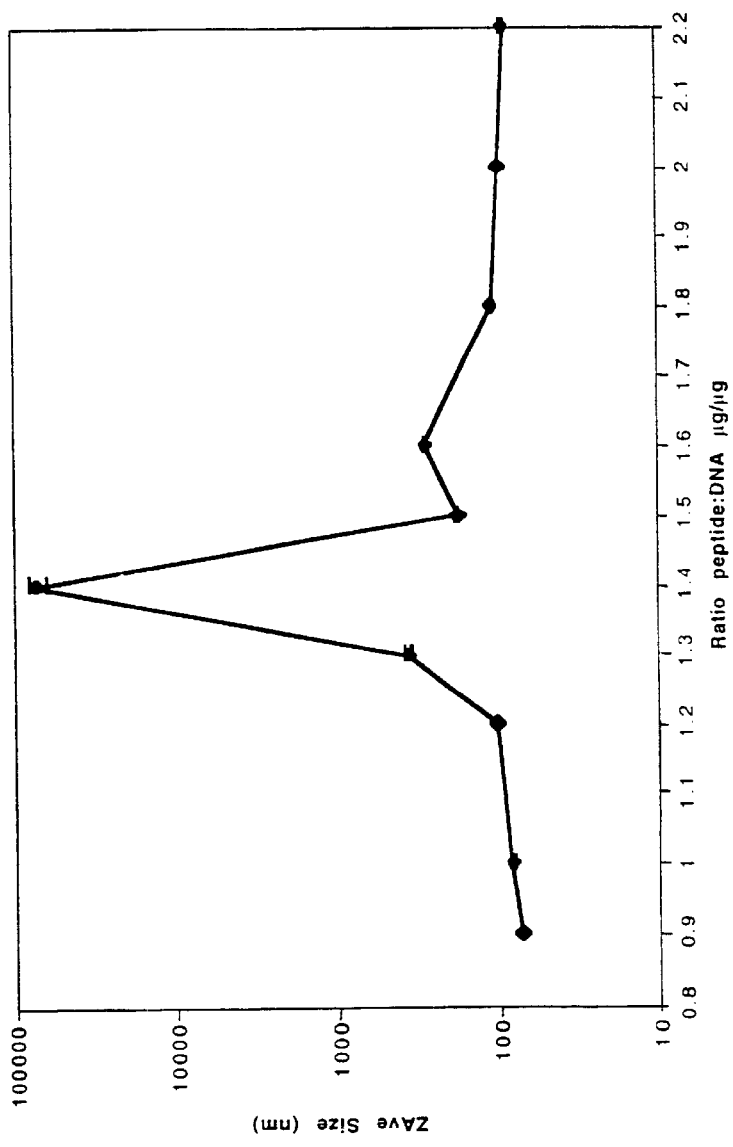
FIG. 1 is a graph indicating that small particles are formed at various ratios of peptide:DNA in HEPES buffer in the absence of added NaCl.
Figure 5B:
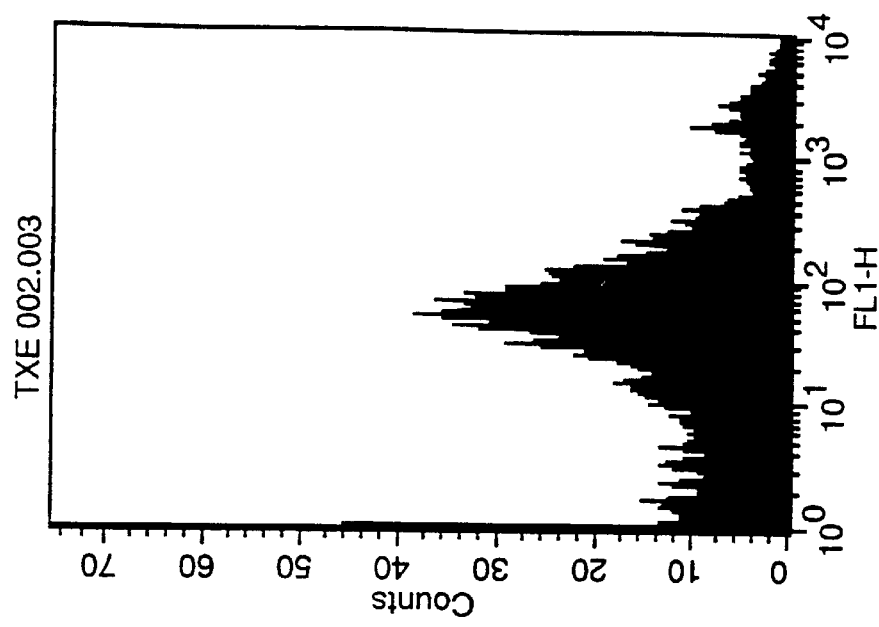
FIG. 5 represents FACScan analysis of Cos cells incubated with either buffer (A), peptide alone (B), or complex (C). D represents an overlay plot (thin line, buffer; solid broad line, peptide, lined line, complex).
Figure 5A:
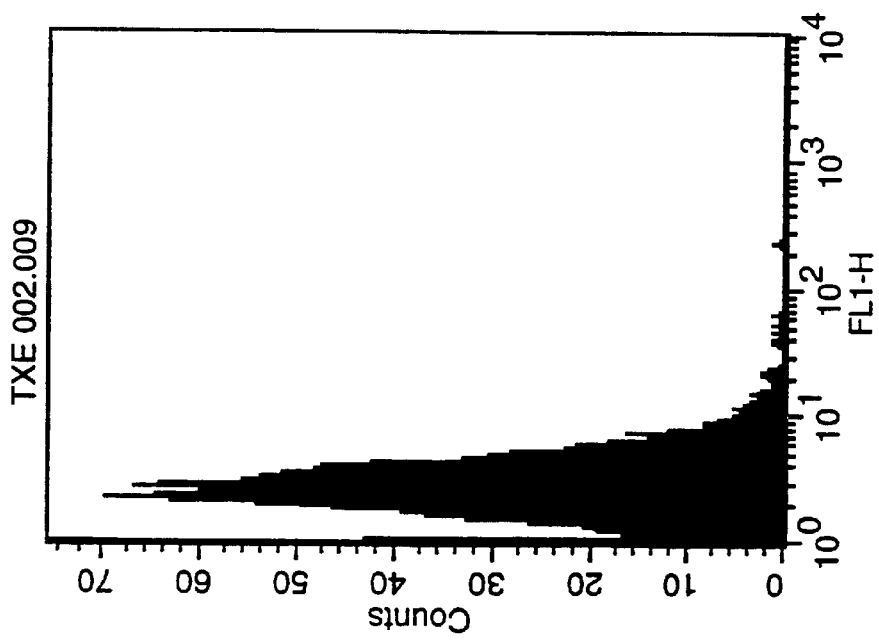
Figure 5D:
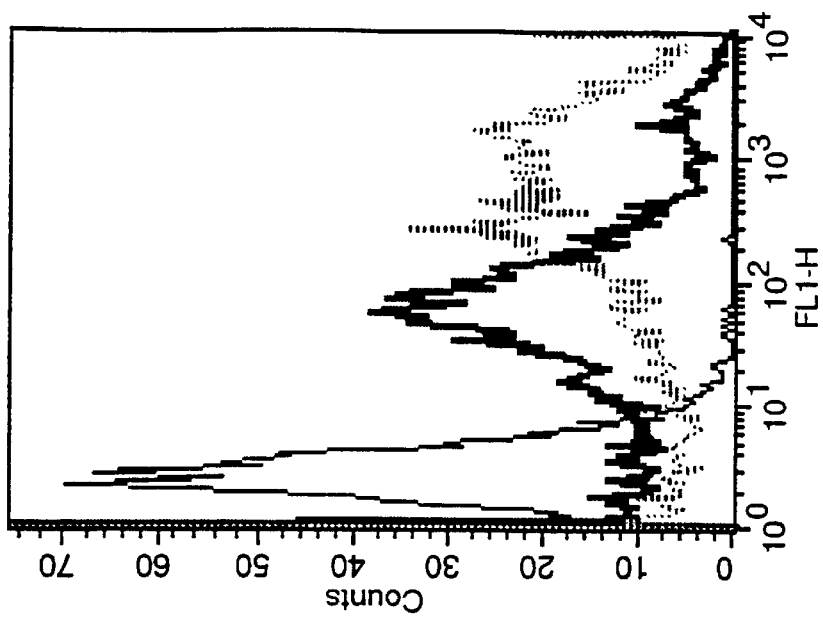
Figure 5C:
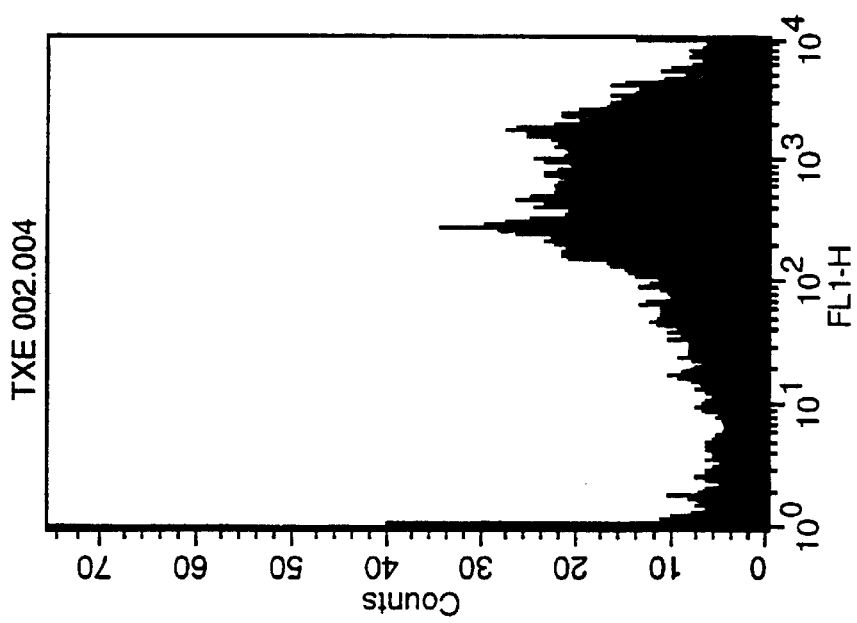

The invention is illustrated by the following nonlimiting examples wherein the following materials and methods are employed. The entire disclosure of each of the literature references cited hereinafter are incorporated by reference herein.

The invention is based on the discovery of polypeptides which, when associated with a nucleic acid, dramatically increase the efficiency by which the nucleic acid is introduced into the cell.

The polypeptides as well as their synthesis are described herein, as well as preparation of the polypeptide transfection complexes. Transfection of a host cell using a polypeptide/nucleic acid complex also is described hereinbelow.

Polypeptides according to the invention have the following 29 amino acid composition: 6G's, 2F's, 2L's, 1W, 4R's, 2E's, 2N's, 3K's, 1T, 1S, 1A, 1Y, 1M, 1C, and 1I, and have additional cationic residues to provide a net number of positive charges of equal to or greater than 8. Cationic residue refers to an amino acid or other molecule having a net positive charge, examples of which include but are not limited to lysine, ethyleneimine, arginine, methacrylate, amidoamine, protamine, spermine, and spermidine. The 29 amino acids specified above contained in the polypeptide contain 3 cationic residues and 2 anionic residues and thus contain a net of 5 cationic charges, and the additional cationic residues will number at least 3 and preferably 4 or 5, and more preferably number, for example, 6, 12, 18 and 24.

Polypeptides according to the invention will therefore contain the 29 amino acids specified above and additional cationic residues sufficient to net equal to or greater than 8 positively charged residues in the polypeptide, wherein the 29 amino acids specified above may be present in the polypeptide as (a) a block of: 29 contiguous amino acids and equal to or greater than (≧) 3 cationic residues (monomer) or (b) as two or more blocks of the 29+≧3 amino acids (dimer, trimer, etc., i.e., multimer). Where a 29+≧3 polypeptide is present in a multimeric form, several individual 29+≧3 polypeptides may be linked in conventional stable bonds (peptide, oxime, or thioether) or the polypeptides may be linked via labile bonds, e.g., disulfide bonds.

A cationic sequence useful herein may be a tract of contiguous cationic residues in the length range of 3 to 700, whereby the net cationic charge is at least 3. Alternatively, the tract of cationic sequences need not be contiguous, but may be dispersed among basic or neutral amino acids such that the net number of cationic charges is in the range of 3 to 700. Therefore, a polypeptide according to the invention may contain as few as (5+3=)8 net cationic charges or as many as (5+700=)705 net cationic charges. A given cationic sequence may be linked in conventional stable bonds at either the amino or carboxy terminus of the 29 amino acid tract specified above, or at both ends, or within the 29 amino acid tract. If cationic sequences are present at both ends of the 29 amino acid tract, then each end may contain a different number of cationic residues or an identical number of cationic residues. Alternatively, the cationic sequence may be bonded to the 29 amino acid tract at one or more position along its length via a labile (sulfhydril) or a stable bond. Finally, the 29 amino acid tract may be linked to a cationic residue at one or more position along the length of the cationic sequence via a labile or stable bond.

Preparation of Polypeptides According to the Invention via Recombinant DNA Methods The preparation of K6CL22 is provided as a representative polypeptide. K6CL22 may be prepared by expression of a nucleotide sequence encoding K6CL22. For example, the following sequence may be expressed in *E. coli*.

```
NH2- K   K   K   K   K   K   G   G   F   L
  5'AAA AAA AAG AAA AAA AAA GGT GGT TTG CTG

G   F   W   R   G   E   N   G   R   K   T   R
  GGT TTC TGG CGT GGT GAA AAC GGT CGT AAA ACC CGT

S   A   Y   E   R   M   C   N   I   L   K   G
  TCT GCT TAC GAA CGT ATG TGC AAC ATC CTG AAA GGT

K     -COOH (SEQ ID NO:1)
  AAA 3' (SEQ ID NO:7)
```

The polypeptide may be expressed from this sequence in any given expression system known in the art, and purified according to conventional purification techniques.

Synthesis of K6CL22 and LicK6CL22

The following abbreviations are used. Boc-t-Butoxycarbonyl; Fmoc-Fluorenylmethoxycarbonyl; tBu-tButyl; Pbf-2,2,4,6,7-pentamethyldihydrobenzofuran-5-sulfonyl; PEG-polyethyleneglycol; PS-polystyrene; Trt-trityl; RP-HPLC-reverse phase high performance liquid chromatography.

Preparation of K6CL22 Peptide

K6CL22 has the following amino acid sequence:
NH2-KKKKKKGGFLGFWRGENGRKTRSAYERMC NILKGK-COOH (SEQ ID NO:1).

K6CL22 was prepared by solid phase peptide synthesis on Fmoc-Lys(Boc)-O-PEG-PS-Resin at a 0.85 mmol scale. The synthesis was accomplished using a Biosearch 9050 plus Pepsynthesizer in extended synthesis cycle mode. Lysine and tryptophan side chains were Boc protected; arginine side chains were Pbf protected; serine, threonine and tyrosine side chains were tBu protected; the asparagine and cysteine side chain was Trt protected and glutamate side chains were tBu protected. The amino acid derivatives were coupled in a 3 molar excess using 0.6M O-(1H-benzotriazo-1-yl) tetramethyluronium tetrafluoroborate (TBTU) in dimethylformamide/ 0.9M N-ethyldiisopropylamine in dimethylformamide as activating agents. Deprotection of the N-termninal Fmoc group before each coupling was achieved using a solution of 20% piperidine in dimethylformamide (1 min at high flow rate followed by 10 min at 3 ml/min.). The coupling time for each residue was 1.5 h.

On completion, the resin conjugated peptide was washed with dichloromethane and dried. The peptide was cleaved from the resin using trifluoroacetic acid/triisopropylsilane/ thioanisole/1,2-ethanedithiol (92.5:2.5:2.5:2.5) for 1.5 h at room temperature, which simultaneously deprotected the amino acid side chains. The resin was then removed by filtration and washed with trifluoroacetic acid. The combined filtrate and washings were concentrated by evaporation then precipitated using diethyl ether followed by centrifugation to give the crude peptide. The crude peptide was dissolved in a minimum volume of 20 mM ammonium acetate, pH 4.6 and purified using a Sephadex G25 (Superfine) gel filtration column (100×2.6 cm) run in the same buffer. The fractions containing peptide, as determined by analytical RP-HPLC, were pooled and lyophilised. Further purification was achieved by preparative HPLC using a $C_{18}$ RP-HPLC column (Dynamax 83-221-C) and a gradient of 20–50% acetonitrile (0.1% trifluoroacetic acid) in water (0.1% trifluoroacetic acid) over 30 min. The fractions corresponding to the major peak on the chromatograph were pooled and lyophilised. Finally, the peptide was desalted using a Sephadex G15 (Medium) gel filtration column (70×2.6 cm) run in 20 mM ammonium acetate, pH 4.6. The peptide fractions, which were detected by analysis at 226 nm, were pooled and lyophilised. The pure peptide was stored at −20° C.

The peptide (expected molar mass 4101.9) was characterized using matrix assisted laser desorption/ ionization (MALDI) mass spectrometry. 0.1–0.5 mg of peptide was dissolved in 1 ml of 0.1% trifluoroacetic acid, and 0.5 μl applied to the target and analyzed using a Kratos Kompact MALDI II-tDE spectrometer.

Disulphide Formation to Give K6CL22 Dimer 1.0 ml of 20 mM ammonium bicarbonate was added to 10.0 mg free thiol containing K6CL22 peptide. The cysteine thiols were left to oxidise at 25° C. in a vial left open to the air. The progress of dimerisation was followed by observing the change in original retention time of the peptide by capillary electrophoresis. After 16 h the peptide was judged to have dimerised completely. Addition of 10 mM DTT to a peptide subsamnple reversed the observed shift in retention time. Dimer formation was also confirmed by gel filtration analysis using a Superdex Peptide (HR 10/30) column. Finally, the peptide was frozen and lyophilised to give the bicarbonate salt.

Preparation of LIC-K6CL22 Lipopeptide

LIC-K6CL22 is a disulphide-linked cholesterol-K6CL22 conjugate with the following structure:

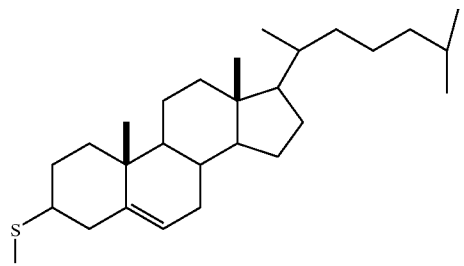

NH2-KKKKKKGGFLGFWRGENGRKTRSAYERMCNILKGK-COOH
(SEQ ID NO: 1).

21.0 mg (97 μmol) 2,2'-dithiodipyridine was dissolved in 1 ml methanol and added to 40.0 mg (9.7 μmol) K6CL22 made up in 4 ml methanol. The reaction was left at room temperature for 1 h. The methanol was evaporated off under vacuum and 2 ml water added to the solid residue. The suspension was passed through a 0.4 μm filter, and the filtrate was injected onto a preparative $C_{18}$ RP-HPLC (Dynamax 83-221-C) column and purified using 0–30% acetonitrile (0.1% trifluoroacetic acid) in water (0.1% trifluoroacetic acid) gradient. The peptide containing fractions were pooled and lyophilised. 10 mg (45 μmol) modified K6CL22 were dissolved in 2 ml methanol and 0.5 mg 3β-thiocholesterol in 1 ml chloroform added. The solution was mixed and left at room temperature for 48 h. The solvents were evaporated off under vacuum and the residue dissolved in 2 ml water and filtered to remove excess lipid. The peptide was purified finally on a preparative $C_4$ RP-HPLC column (Dynamax 83-523-C5) using a 5–100% acetonitrile (0.1% trifluoroacetic acid) in water (0.1% trifluoroacetic acid) gradient. The lipopeptide containing fractions were pooled and lyophilised.

The pure lipopeptide, LIC-K6CL22 (expected molar mass 4502.1), was characterized by mass spectrometry as described for K6CL22.

Structure of CL28 Peptide

CL28 has the following amino acid sequence:
H-KKKKKKGGFLGFNTKERNLKRGWEICRSAMGY GRK-OH (SEQ ID NO:2).

The amino acid composition of CL28 is identical to that of K6CL22 except that in the case of CL28, the sequence of residues 13–35 is randomized.

Preparation of CL28 Peptide

CL28 was prepared by solid phase peptide synthesis using the method described for K6CL22. CL28 was purified using the method described for K6CL22.

The peptide (expected molar mass 4101.9) was characterized using matrix assisted laser desorption/ionisation (MALDI) mass spectrometry. 0.1–0.5 mg of peptide was dissolved in 1 ml of 0.1% trifluoroacetic acid, and 0.5 μl applied to the target and analysed using a Kratos Kompact MALDI II-TDE spectrometer.

Disulphide Formation to Give CL28 Dimer 1.0 ml of 20 mM ammonium bicarbonate was added to 10.0 mg free thiol containing CL28 peptide. The cysteine thiols were left to oxidise at 25° C. in a vial left open to the air. The progress of dimerisation was followed by observing the change in original retention time of the peptide by capillary electrophoresis. After 16 h the peptide was judged to have dimerised completely. Addition of 10 mM DTT to a peptide subsample reversed the observed shift in retention time. Dimer formation was also confirmed by gel filtration analysis using a Superdex Peptide (HR 10/30) column. Finally, the peptide was frozen and lyophilised to give the bicarbonate salt.

Structure of CL26 Peptide

CL26 has the following amino acid sequence:
H-KKKKKKKKKKKKGGFLGFWRGENGRKTRS AYERMCNILKGK-OH (SEQ ID NO:3).

The amino acid composition of CL26 is identical to that of K6CL22 except a six lysine sequence extension at the Nterminus.

Preparation of CL26 Peptide

CL26 was prepared by solid phase peptide synthesis using the method described for K6CL22. CL26 was purified using the method described for K6CL22.

The peptide (expected molar mass 4871.0) was characterised using matrix assisted laser desorption/ionisation (MALDI) mass spectrometry. 0.1–0.5 mg of peptide was dissolved in 1 ml of 0.1% trifluoroacetic acid, and 0.5 μl applied to the target and analysed using a Kratos Kompact MALDI 11-tDE spectrometer.

Disulphide Formation to Form CL26 Dimer

Disulfide bond formation was carried out as described for CL28.

Structure of NBC26 Peptide

NBC26 has the following amino acid sequence:
H-WKKKKKKKKKKKKKKKKKKKCG-OH (SEQ ID NO:4).

Preparation of NBC26 Pepide

NBC26 was prepared by solid phase peptide synthesis and purified in a method similar to that described for K6CL22.

The peptide (expected molar mass 2671.6) was characterised using capillary electrophoresis, HPLC and matrix assisted laser desorption/ionisation (MALDI) mass spectrometry. 0.1–0.5 mg of peptide was dissolved in ml of 0.1% trifluoroacetic acid, and 0.5 μl applied to the target and analysed using a Kratos Kompact MALDI II-tDE spectrometer.

Structure of NBC30 Peptide

NBC30 is comprised of two polypeptide chains and has the following amino acid sequence and secondary structure:

H-KKKKKKGGFLGFWRGENGRKTRSAYERMCNILKGK-OH (SEQ ID NO: 1)

The amino acid composition of chain I is identical to that of NBC26. The amino acid composition of chain II is identical to that of K6CL22. The K6CL22 chain is linked via a cystine bridge to the lysine rich sequence NBC26.

Preparation of NBC30 Peptide

NBC26 and K6CL22 chains were prepared separately by solid phase peptide synthesis and purified as described earlier.

The two chains were linked as follows:
1. NBC26 (20 mg; 7.5 μmol) was dissolved in 1.0 ml 50% acetonitrile in water.

Solid 2,2'-dipiyridyldisulphide (10 mg; 50 μmol) was added to the stirred peptide solution, and the reaction mixture left at room temperature in the dark for 1 h. The solution was then frozen, lyophilised and the peptide dissolved in 1.0 ml water in an Eppendorf. The insoluble residual reagent was removed by centrifugation. The peptide was purified by preparative RP-HPLC on Dynomax $C_{18}$ (83-221-C) using a gradient of 0–50% B=acetonitrile (0.1% TFA). The thiol-activated NBC26 was frozen and lyophilised.

2. To 7 mg (2.6 μmol) thiol-activated NBC26 in 1.0 water were added to 10 mg (2.4 mmol) K6CL22. The reaction was left overnight at 4° C. and the dimer formation confirmed by analytical gel filtration (Pharmacia Superdex Peptide HR10/30 column). Finally, the peptide dimer was purified by semipreparative RP-HPLC on a BDS Hyperpep 300 C18 column using a gradient of 0–50% B over 20 min, where A and B are described above; dimer containing fractions were pooled and lyophilised to give solid NBC30.

The peptide (expected molar mass 6771.5) was characterised using capillary electrophoresis, HPLC and matrix assisted laser desorption/ionisation (MALDI) mass spectrometry. 0.1–0.5 mg of peptide was dissolved in 1 ml of 0.1% trifluoroacetic acid, and 0.5 µl applied to the target and analysed using a Kratos Kompact MALDI II-tDE spectrometer (observed mass =6773.5; constituent peptide chain masses also observed at 2674.0 and 4104.2 due to partial disulphide reduction during MALDI analysis).

Preparation of K6CL22-DNA Complexes for PCS and Zeta Analysis and Transfection Assays K6CL22 concentration was determined by absorbance at 280 nm using $E^{280}{}_{0.1\%}=1.67$ cm$^{-1}$ DNA concentration was determined by absorbance at 260 nm using $E^{260}{}_{0.1\%}32$ 20 cm$^{-1}$.

Complexes between K6CL22 and DNA were formed in the following way in a laminar flow hood: A stock solution of K6CL22 (typically 8–12 mg/ml) was stored in water at −20° C. This was thawed and diluted to 4–400 µg/ml in either 10 mM HEPES pH7.4 (Hepes) or 10 mM HEPES/150 mM NaCl pH 7.4 (HBS). (It should be noted that these non-reducing conditions favor the formation of peptide dimers via disulfide bonding between peptides of cysteine residues in the peptide). A stock solution of pCMVβ plasmid DNA (typically 2–4 mg/ml in either water or TE buffer) was diluted to 40 µg/ml in Hepes or HBS. Peptide (typically 0.4–1 ml) was added to an equal volume of diluted DNA. Different target ratios of Peptide:DNA were achieved by varying the concentration of added peptide. Samples were immediately mixed by gently sucking up and down in a pipette tip and left to incubate at room temperature for a minimum of one hour or if required overnight at 4° C.

In FIG. 1, peptide and DNA were mixed as described above and incubated over night at 4° C. The final DNA concentration was 40 µg/ml.

This graph indicates that small particles in the size of about 100 nm are formed at various ratios of peptide:DNA in HEPES buffer in the absence of added NaCl. However there is a particular ratio at which large particles/aggregates are formed. With this peptide the ratio is approx. 1.4:1 (peptide:DNA).

In FIG. 2, peptide and DNA were mixed as described above and incubated for one hour at room temperature. The final DNA concentration was 40 µg/ml.

This graph shows that in the presence of 150 mM NaCl large particles/aggregates of complex of approx. 1000 nm are formed at similar peptide:DNA ratios. Larger aggregates may form on further incubation. Little variation of size is observed with increased peptide/DNA ratio.

Photon Correlation Spectroscopy (PCS)/Quasi-Elastic Laser Light Scattering (QUELLS)

For PCS analysis the buffers used in the preparation of samples were filtered through 20 nm filters. Analyses were carried out at 25° C. and at an angle of 90° using a Malvern Instruments 4700 PCS instrument fitted with an argon-ion laser. Samples were allowed to equilibrate to 25° C. prior to measuring, and an average Zav was determined from a minimum of three measurements. Typically the laser power was set to 12 mW. The PMT aperture was 100 µm. Zav and intensity and volume distributions were determined using Malvern PCS software. Constants used in the software calculations were as follows: Viscosity=0.88cP, RI medium=1.33, RI particle=1.6 Imaginary RI of particle=0.

Zeta Potential Analysis

Zeta potential was determined on samples prepared in Hepes using a Malvern Instruments Zetasizer 3000 fitted with a standard Zeta cell. The Zeta cell was first flushed with 20 nm filtered Hepes to equilibrate the cell followed by a pulse of air to blow out the buffer. A 2 ml sample was then loaded into the cell. The Zeta potential was determined from an average of 6 measurements for each sample. The data was analyzed using Malvern Zeta software with automatic settings.

In FIG. 3, samples prepared in HEPES for PCS analysis were also analyzed for Zeta potential.

This graph indicates that as the peptide:DNA ratio is increased the zeta potential of the complex becomes less negative. At a ratio of 1.4:1 that zeta potential is zero.

FIG. 4 shows the same results above but overlaid with the corresponding PCS results which demonstrate that the average (Zav) particle size is approximately 100 nm, and aggregation is occurring at a ratio in the range of 1.2–1.6 µg peptide/µg DNA, with an average of 1.4.

Preparation of Transfection Complexes and Determination of Condensing Activity

A "transfection complex" as used herein, refers to a non-covalent association of K6CL22 and nucleic acid, that is, an association based on charge:charge (+:−) interaction between the negatively charged phosphate groups of the nucleic acid and the positively charged cationic groups (e.g., amino groups) of the peptide.

A transfection complex including K6CL22 and a nucleic acid comprises condensed nucleic acid at certain peptide-:nucleic acid ration.

One can determine whether or not a nucleic acid is condensed by a gel retardation assay in which condensed nucleic acid migrates slower or remains in the well of an agarose gel or a nondenaturing polyacrylamide gel.

Preparation of transfection complexes and a gel retardation assay is performed as follows.

Transfection complexes are prepared by combining nucleic acid and K6CL22 peptide under conditions which permit condensation of the nucleic acid. A concentration of nucleic acid is selected, for example 20, 30, or 40 µg/ml and possibly 50, 60, 70, or 100 µg/ml, and prepared in a low salt buffer, e.g., 150 mM NaCl.

In one embodiment, the required amount of DNA is made up to 20 µg/ml in 150 mM NaCl; 25 mM HEPES, pH 7.4, or in 0.6 M NaCl; 25 mM HEPES, pH 7.4 and aliquoted between wells on a multiwell plate. The amount of conjugate or peptide required to give positive charge:phosphate ratios of between 0.1 and 5.0 is calculated. This is made up to an equal volume to the DNA aliquots (0.05–0.5 ml) in either 150 mM sodium chloride; 25 mM HEPES, pH 7.4 or 0.6 M sodium chloride; 25 mM HEPES, pH 7.4. The plate containing the DNA is placed on a plate shaker and shaken while the peptide is added at a rate of 0.1 volume per minute. After addition of K6CL22 peptide is complete, the solution is incubated at room temperature for at least 30 minutes. A sample for each positive charge:phosphate ratio is subjected to electrophoresis on an agarose gel. The gel is stained with ethidium bromide and visualized under UV light. Condensed DNA remains in the well of the gel and does not migrate in the electric field.

Characteristics of the Transfection Complex

1) Overall Size

It is preferred according to the invention that the size of a transfection complex when formulated and measured by PCS fall within the range of 5 nm to 1500 nm. Complex size is measured by lasar light scattering or atomic force microscopy, or electron microscopy.

2) Ratio of K6CL22 peptide/nucleic acid.

A transfection complex according to the invention may have a ratio of the number of peptide/the number of nucleic acid molecules in a particle that is within the range of 10/1 to 1,000,000/1. This ratio will depend upon the relative sizes of the peptide and nucleic acid molecules, the degree of condensing activity of the peptide, and the degree of condensation that the nucleic acid attains. More particularly, the range will be 200/1–20,000/1. For example, for K6CL22 in combination with an approximate 8 kb vector, a useful ratio for untargeted delivery of the vector to cells is approximately 2,500:1 (relative numbers of molecules). For licK6CL22 (K6CL22 conjugated to lipid) in combination with an 8 kb vector, a useful ratio for targeted delivery of the vector to cells is approximately 2,000:1. Where the nucleic acid is an oligonucleotide of, e.g., 10–50 nucleotides in length, the ratio of peptide/oligonucleotide is in the range of 0.1–10.0 and is preferably 0.5–1.0.

In terms of tg peptide/pg nucleic acid, it has been determined that the ratio of K6CL22 peptide/nucleic acid which is most useful in transfection is in the range of 1.0–3.0, with the highest transfection efficiency generally attained in the range of 1.6–2.2.

The ratio of positive/negative charges in a transfection complex containing K6CL22 and a nucleic acid may be within the range 0.2–20 per phosphate residue in the nucleic acid; this ratio more preferably being within the range 0.8–3.0.

3) Chloroquine

Increased transfection efficiency is observed when a transfection complex containing K6CL22 or lipidated K6CL22 is coadministered with chloroquine. The range of concentrations useful according to the invention are generally from 10 $\mu$M to 1 mM. At the higher dosage, the maximum amount of chloroquine administered with the transfection complex in vivo should not exceed 3.5 mg/kg body weight. For ex vivo applications, the final concentration of chloroquine after dilution from the formulation is in the range of 50 nM–200 $\mu$M, with a preferred range of 1 $\mu$M–100 $\mu$M.

It has also been found that transfection efficiency is increased by extending the time period to which the target cells are exposed to the transfection complex in the presence of chloroquine. This time period may be from 2 hours to as much as 24–48 hours, with the longer incubation times resulting in increased transfection efficiency in the presence of chloroquine.

4) Functional groups.

K6CL22 also may contain one or more attached functional groups, for example, a lipid (licK6CL22). Other functional groups refer to a protein, peptide, lipid, or chemical group that is covalently or non-covalently (e.g., via a coiled coil interaction) linked to K6CL22 or licK6CL22, and which may confer an additional biological function with respect to complex stability in biological fluids, entry into a cell, or delivery of DNA to the cell nucleus, or integration into the chromosome. The covalent linkage may be a stable or labile linkage. Thus, where it is desired to add a functional group to K6CL22 via chemical means, this may be accomplished via addition of the functional group to an internal Serine, Threonine, or Cysteine residue, preferably at a position in the sequence which will be exposed for conjugation to a selected ligand. Cysteine allows specific conjugation via the thiol side chain to compounds containing other reactive thiol groups (via disulfides), alkylating functions (to form thioether bonds), or other thiol reactive groups such as maleimide derivatives. Bonds of "defined stability" are described herein below, and include bonds such as acid labile bonds (hydrazone) or linkages that are less stable in the reducing environment of the cytosol (disulfide). Such bonds are useful for carrying functional groups on the transfection complex. Where the functional group is a peptide, the covalent linkage may be a peptide bond, thus creating a fusion protein.

Examples of functional groups useful according to the invention include but are not limited to the following: a) a ligand, such as i) an antigenic peptide, or ii) a targeting molecule having a cognate receptor on the surface of a target cell; b) a lipid; c) a neutral hydrophilic polymer; d) an endosomal disruption agent; e) an enzyme, and f) an agent which promotes intracellular trafficking into the nucleus, and combinations thereof.

As used herein, the term "lipid" refers to a four-thirty carbon molecule that is insoluble in water and soluble in alcohol. The term includes fats, fatty oils, essential oils, waxes, sterols, cholesterols, phospholipins, glycolipins, sulfolipins, aminolipins, chromolipins, and fatty acid. K6CL22 can be specifically modified by condensation with an lipid, for example, an activated ester of a fatty acid. The fatty acid is ideally either palmitic acid, oleic acid, such as dioleoylphosphatidylethanolamine, myristic acid, or cholesterol, although other fatty acids, such as stearic acid, may also be employed.

A functional group useful according to the invention also includes a ligand which serves to promote cellular uptake, e.g., by disrupting membrane structure, such as the HA peptide from the influenza virus. Additional fusogenic peptides useful according to the invention include the fusogenic peptide from Sendai Virus (D. Rapaport and Y. Shai, J. Biol. Chem. 1994,263,15124–15131), the fusogenic peptide sequence from HIV gp41 protein (M. Rafalaski, J. D. Lear and W. F. DeGrado, Biochemistry 1990,29,7917–7922), the fusogenic peptide sequence from Paradaxin (D. Rapaport, G. R. Hague, Y. Pouny and Y. Shai, Biochemistry 1993,32, 3291–3297), and the fusogenic peptide sequence from Melittin: (C. R. Dawson et al., Biochem. Biophys. Acta: 1978,510,75).

Transfection of Cells

As described below, cells are transfected with a complex comprising K6CL22 and a nucleic acid, and the nucleic acid or its gene product is detected in the cell.

Transfection Protocol 1

1. Trypsinise cells to harvest and seed into 6-well plates, 1×10⁵ cells/well in 3 ml. Allow triplicate wells per point (usually Mock, positive control and 12 samples) and two sets of plates per experiment. Incubate at 37° C. overnight to establish.

2. Next day aspirate medium from wells and carefully wash with SF RPMI (1×).

3. Add 875 $\mu$l RAQ (or RA where the experiment is done in the absence of chloroquine) per well. Then add 125 $\mu$l complex (or SF RPMI) dropwise, using a gilson. Gently swirl plates to ensure mixing. Incubate at 37° C. for 5 hours.

4. After incubation, aspirate the transfection media from the wells and replace with 3 ml fresh DF10 per well. Incubate overnight.

5. Assess transfection efficiency the following day by (a) Galacto-light and X-gal staining for CMVβ plasmid or (b) Immunostaining and ELISA for ntr-containing plasmids. (CMVβ was bought from Clontech Laboratories, Inc. Catalogue Number 6177-1. Originally made by MacGregor & Caskey, Nucl. Acids Res. vol 17 p2365 (1989).)

RAQ

Add 11.36 ml human serum albumin to 500 ml RPMI. Store this (RA) at 4° C. Prior to setting up transfections, dispense the required volume of RA (0.875 ml×no. of wells) into a sterile container and add 13.7 $\mu$l of 10 mM chloroquine (Q) per ml. This leads to a final concentration of 120 $\mu$M chioroquine in the transfection media after the addition of complex.

Mocks

Mock wells are essentially negative controls, i.e., not transfected. Add 125 $\mu$l SF RPMI to the RAQ (step 3 above) instead of complex.

Positive control

Stock DNA is kept at concentrations of around 0.5 mg/ml; higher concentrations should be diluted down to this with $dH_2O$ and the exact concentration determined.

PEG diluent (see below): 10 g PEG 8000
5 ml 0.5M $PO_4$–pH7.4
750 µl 5M NaCl

Make up to 100 ml with $dH_2O$ and filter through a 0.2 µM filter to sterilize.

Make up 'positive control' complex as follows;

a) Add the following in descending order to a well of a 'v'-bottomed 96-well plate:

| | | |
|---|---|---|
| 15 mg/ml NBC9 | 2.4 µl | (2 µg/µg peptide/DNA) |
| $dH_2O$* | 103.8 µl | |
| 0.5 M $PO^-_4$ | 9.0 µl | |
| 5M NaCl | 21.6 µl | |
| DNA* | 36.0 µl | |
| 1 mg/ml LIP9 | 7.2 µl | (0.4 µg/µg peptide/DNA) |
| | (180 µl final) | |

*amounts are given for a 0.5 mg/ml DNA solution. For other stock DNA concentrations adjust amounts accordingly. A final concentration of 100 µg/ml is required.

NBC9 is a histone based peptide with the following amino acid sequence:

H2-TKKSPKKAKKPAAKKSPKKAKKPAAKKSP KKAKKPAAC(Acm)-COOH (SEQ ID NO:5). The terminal cysteine of NBC9 is blocked with an acetamidomethyl group.

b) Cover plate with a plate sealer plus lid (to minimize evaporation) and incubate for 1 hour at RT, followed by overnight in the fridge.

c) Just prior to transfection, add 660 µl of PEG diluent to a well of a 24-well plate and put plate on shaker in hood. Set to shake at 500–600. Remove 165 µl of complex from 96-well plate and add dropwise to PEG whilst shaking.

d) Add 125 µl diluted complex to RAQ in wells (use within 1 hour of dilution).

Samples are at 20 µg/ml DNA. Add 125 µl per well.

X-gal Staining (CMV-transfected cells)

Protocol 2

1. Remove supernatant and wash cells with PBS (approx. 2 mls/well).
2. Fix cells with 1 ml/well of 0.05% gluteraldehyde. Incubate at RT for 10 mins.
3. Wash cells with PBS.
4. Stain cells with 1ml/well of X-gal solution. Incubate plate overnight at 37° C.
5. Next day look for presence of blue cells. Blue stained cells indicate that the gene has been successfully delivered to the cells.

Gluteraldehyde

Stock gluteraldehyde at 25% is obtained from SIGMA and kept frozen in aliquots. Dilute to 0.05% with PBS (1 in 500 dilution).

X-gal Solution

X-gal stock: 40 mg/ml in Dimethyl formamide.

X-gal buffer: 20 mM $K_3Fe(CN)_6$ Potassium Ferricyanide (0.66 g/100 mls) 20 mM $K_4Fe(CN)_6.3H_2O$ Potassium Ferrocyanide (0.84 g/100 mls) 2 mM $MgCl_2$ in PBS.

Dilute X-gal stock in X-gal buffer by a factor of 1 in 40 to give a 1 mg/ml solution.

Galacto-Light Assay (CMVβ-transfected cells)

Protocol 3

1. Wash cells 1×with PBS.
2. To prepare cell extracts, add 250 µl lysis buffer/well of the 6-well plate. Scrape off cells and pipette up and down to aid cell lysis.
3. Transfer to eppendorf. Centrifuge @ 13K rpm for 2 mins.
4. Transfer supernatants to clean eppendorfs.
5. For each supernatant, transfer 10 µl to an illuminometer tube.
6. Prepare positive and negative controls.
7. Add 100 µl of Reaction buffer (with repeat pipette) to each illuminometer tube. Shake to mix. Incubate at room temperature for 60 mins.
8. Prepare illuminometer by washing through with Light Emission Accelerator, three times, by selecting 'others', 'operator function', 'wash cycle', 'start'(2×). Exit out of wash cycle.
9. Run samples by selecting 'measure', 'raw data', 'continue', 10 s (enter), 1 replicate (enter). Setting the illuminometer time for 10 seconds per point will allow the injection of 100 µl Light Emission Accelerator per tube. Remember to check level of Light Emission Accelerator at regular intervals.
10. If readings are too high dilute samples with Galacto-Light Buffer Diluent (10 µl sample in 90 µl buffer) and re-read.
11. Wash illuminometer through with dH20 after use (exit 'measure' program and re-enter wash cycle as indicated in step 7).

Lysis Buffer

Add fresh 100 MM stock DTT (Dithiothreitol) to kit lysis solution to 1 mM (1%).

Reaction Buffer

Warm Galacton Substrate and Galacto-Light Buffer Diluent to room temperature. Dilute Galacton Substrate 100-fold with Galacto-Light Buffer Diluent just prior to use.

Positive Control

Add 1 µl of 0-galactosidase (10 units/ml, see Galacto-Light protocol for details) to 9 µl mock transfected cell extract.

Negative Control

Assay a volume of cell extract equivalent to the volume of experimental cell extract used (i.e. mocks).

Gene Therapy

1. Ex-Vivo Delivery

A transfection complex of the invention also may be demonstrated to be capable of high level transfection of primary cells, e.g., cells of the hematopoietic system, e.g., medium peripheral blood mononuclear cells prepared from peripheral blood by standard Ficoll gradient centrifugation. The cells are incubated using standard assay conditions except that 100 mM chloroquine may be included in the transfection. Transfected cells may be administered to a patient in a dosage that is dependent upon the gene being delivered to the patient, as described below. This dosage may be repeated as called for and as determined by the physician. Parameters which determine the dosage are indicated by the severity of the disease, amenability to treatment by the presence of the gene or gene product, and by a decrease in symptoms of the disease upon treatment.

2. In Vivo Delivery

A murine carcinoma model may be used to demonstrate the efficiency of the transfection complex in vivo, as follows. Three BDF1 male mice (a strain developed by the Paterson Institute of Cancer Research, Manchester U.K. by crossing C57B 16 with DBA2 mice) may be implanted subcutaneously with cells of carcinoma line T50/80, a murine mammary carcinoma cell line which arose spontaneously in BDF1 mice (Paterson Institute; Dodd et al 1989 British J. Cancer 60, 164). 8 weeks after implantation each of the mice carried a 6–9 mm diameter tumor mass on the right flank.

A solution of plasmid DNA (800 mg/ml) coding for the β-galactosidase (lacZ) reporter gene in 25 mM HEPES buffer containing 0.85 mM sodium chloride is mixed at 300 rpm using a vortex mixer (IKA-Schuttler MT4). An equal volume of 800 mg/ml of peptide K6CL22 in the same buffer is added dropwise to the DNA at a rate of 0.1 vol/min. The complex is incubated overnight at 4° C. LicK6CL22 at a final concentration of 0.3 mg/mg DNA is then added to the complex mixture and incubated at 37° C. for 30 minutes.

Three mice bearing T50/80 tumors are anaesthetized with ether and the tumor mass injected with 20 ml of the following solutions: animal (a) HEPES buffer containing 7.14 mg plasmid DNA; animal (b) delivery complex containing 7.14 mg and animal (c) is injected with the same solution as animal (b) with an additional 0.24 ml of a 10 mM solution of chloroquine dissolved in the formulation buffer.

Mice are sacrificed by cerebral dislocation 48 h after injection. Tumors are removed by dissection snap frozen in liquid nitrogen and sectioned (14 mm sections cut through the center of the tumor mass) before fixing in 0.25% glutaraldehyde in phosphate buffered saline. Sections are stained for β-galactosidase activity for 24 h in X-GAL (Sigma Ltd., Poole U.K.) And counter stained with Nuclear Fast Red stain as described by Bout et al.(Exp. Lung Res. 19, 193–202). In this assay cells expressing β-galactosidase activity stain blue.

The slides are examined microscopically. Representative sections of these tumors are presented in photographs taken of sections through tumor tissue transfected with plasmid DNA coding for the reporter gene lacZ, which leads to the expression of the enzyme β-galactosidase. The sections are prepared and stained to show the location of cells expressing β-galactosidase. Slides are examined by and recorded using a standard microscope fitted with bright field optics.

EXAMPLE 1

Transfection of Cos Cells using K6CL22/DNA

Cos7 cells (monkey kidney fibroblasts, A.T.C.C. CRL1651) have been transfected with complexes consisting of K6CL22 peptide (also referred to as K6CL22) and pCNWP (Clonetech) whereas Cos7 cells incubated with an equivalent amount of naked DNA show no transfection.

The DNA and complex solutions were made as follows: DNA solution: 100 μg/ml pC β, 25 mM phosphate pH 7.4, 0.6 M NaCl. Complex solution: 100 μg/ml pCMVβ, 25 mM phosphate pH 7.4, 0.6 M NaCl, 200 μg/ml K6CL22. These solutions were incubated at room temperature for 1 hour and then 4° C. overnight. Cos cells were seeded at 1×10$^5$ cells per well in 6 well plates (in DMEM, 10% Fetal calf serum (FCS)) 24 hours before incubation with complex or DNA.

Figures 7A, 7B:
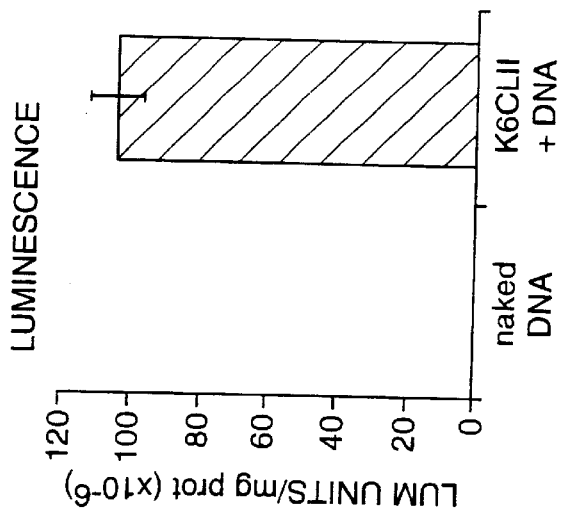

The DNA and complex solutions were diluted into PEG diluent (10% PEG 8000, 25 mM phosphate pH 7.4, 37.5 mM NaCl) to a final DNA concentration of 20 μg/ml. Just prior to transfection the Cos cells were washed with PBS and 875 μl RATQ medium (RAT medium with 137.14 μM chloroquine) was added per well. 125 μl of diluted complex or DNA solution was then added per well and the cells were incubated at 37° C. for 5 hours. The cells were then assayed for β-galactosidase activity using the Tropix Galacto-Light™ kit (Tropix, catalogue no. BL300G) according to the manufacturers instructions. Briefly, the wells were washed with DMEM, 10% FCS, and then 250 μl of lysis buffer (provided by the kit, with dithiothreitol added to 1 mM) was added per well. The cells were then scraped off and were pipetted up and down to aid cell lysis. The lysed cells were transferred to an eppendorf tube and centrifuged at 13K for 2 mins. The supernatant was transferred to a clean eppendorf tube. 2–10 μl of the supernatant was added to a luminometer assay tube and was made up to 10 μl with lysis buffer. 100 μl of Reaction buffer is added to each tube, the samples are incubated at room temperature for 60 mins and then analyzed using Light Emission Accelerator and a Barthoid lumat LB 9501 luminometer. The protein concentration of the cleared cell lysate was measured using the Bio-Rad DC protein assay kit (Bio-Rad). The results are then expressed as relative light units per mg of protein (FIG. 7). Each transfection was carried out in triplicate.

Clearly, there is no detectable transfection of the Cos cells with naked DNA, but there is very efficient transfection with K6CL22/DNA complex.

K6CL22 peptide was fluorescently labeled through the cysteine using Fluorescein-maleimide. The labeling was approximately 7% efficient. The protocol for the labeling was as follows: 4.2 mg K6CL22 was dissolved in 0.5 ml 20 mM MES, pH 6.5. Next, 2.1 mg fluorescein-5-maleimide (Molecular Probes, Europe) was dissolved in 250 μl ethanol and added to the peptide solution. Ethanol was added dropwise until the agitated solution cleared. After 1h at 24° C. the sample was desalted on a PD-10 column (Pierce & Warriner, UK) using 50% aqueous acetonitrile. The fractions containing labeled peptide were lyophilised and stored at −20° C. This peptide will be termed K6CL22-Fl.

Figure 6:
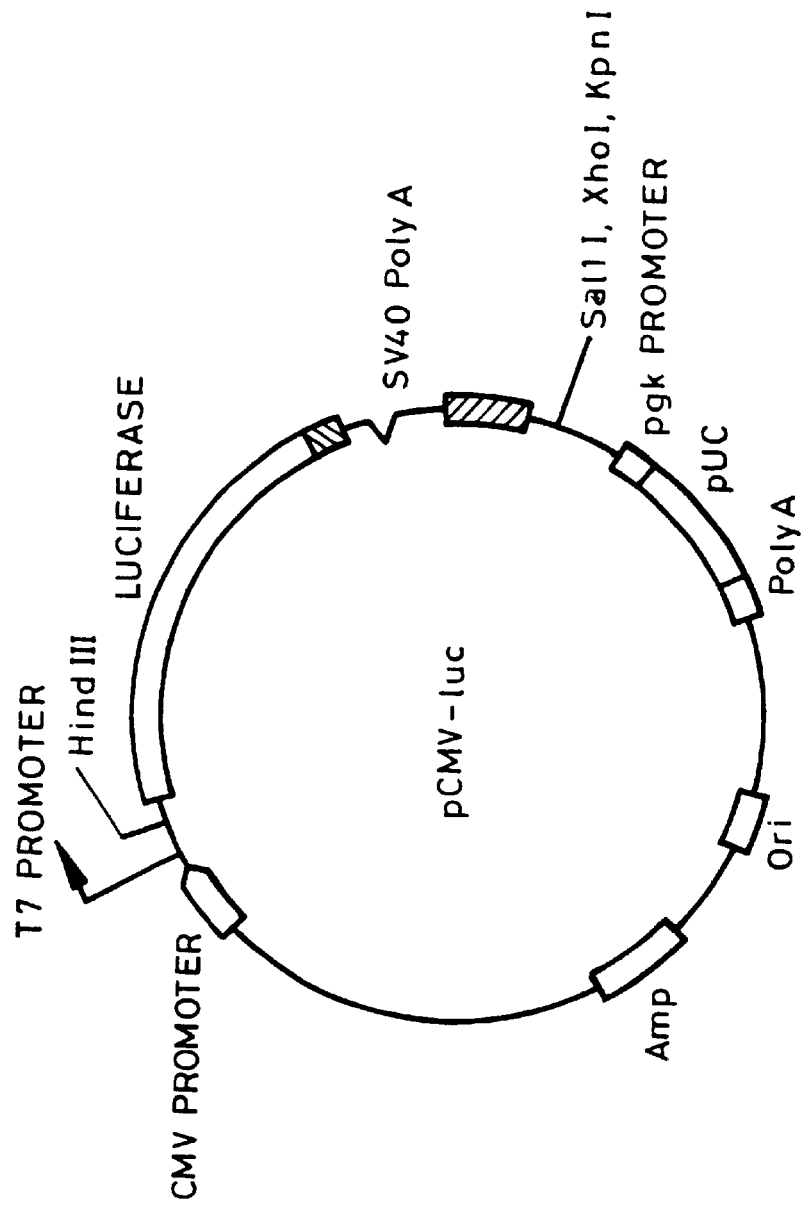
FIG. 6 is a schematic illustration of the plasmid pCMVluc, a luciferase expression vector which has the luciferase gene driven from the CMV immediate early promoter. The plasmid includes the luciferase gene, which contains an SV40 intron and polyA sequence, a bacterial origin of replication and the beta-lactamase gene for selection in bacteria. The plasmid also includes the puromycin gene for selection in eukaryotic cells.

A delivery system was made using K6CL22-Fl and pCM-Vluc (FIG. 6). The delivery vehicle was made in the following way. DNA and peptide solutions were made as follows: DNA Peptide solution: 19.2 ml of K6CL22-Fl (@ 5 mg/ml in sterile water) was added to 1180.8 ml of 10 mM HEPES, 150 mM NaCl (HBS). DNA solution: 56.5 ml of pCMVluc (@ 0.5 mg/ml) was added to 1143.5 ml of HBS.

The peptide solution was then flash mixed with the DNA solution by adding quickly by pipette followed by repeated pipetting. The complex solution was left at room temperature for 1–2 hours before adding to the cells. A control peptide solution contained 19.2 ml of K6CL22-Fl (@ 5 mg/ml) was added to 2380.8 ml of 10 mM HEPES, 150 mM NaCl (HBS).

Cos cells were seeded at 1×10$^5$ cells per well in 6 well plates 24 hours before incubation with complex, peptide or buffer. The Cos cells were washed once with PBS and 800 ml RAT medium was added. 200 ml of complex, free peptide or HBS were then added to the cells. After an incubation of 30 mins the cells were washed twice with PBS and then incubated with 2 ml PBS, 1 mM EDTA to release the adhered cells. The cells were harvested, resuspended in 500 ml PBS and analyzed by FACS analysis (Beckton Dickinson FACScan). The FACS data clearly show that the cells to which complex has been delivered are associated with more fluorescence and therefore more peptide than those incubated with peptide alone (FIG. 5).

EXAMPLE 2

Transfection of Human Dendritic Cells with K6CL22/DNA

Generation of Human Dendritic Cells (DC)

Figure 8:
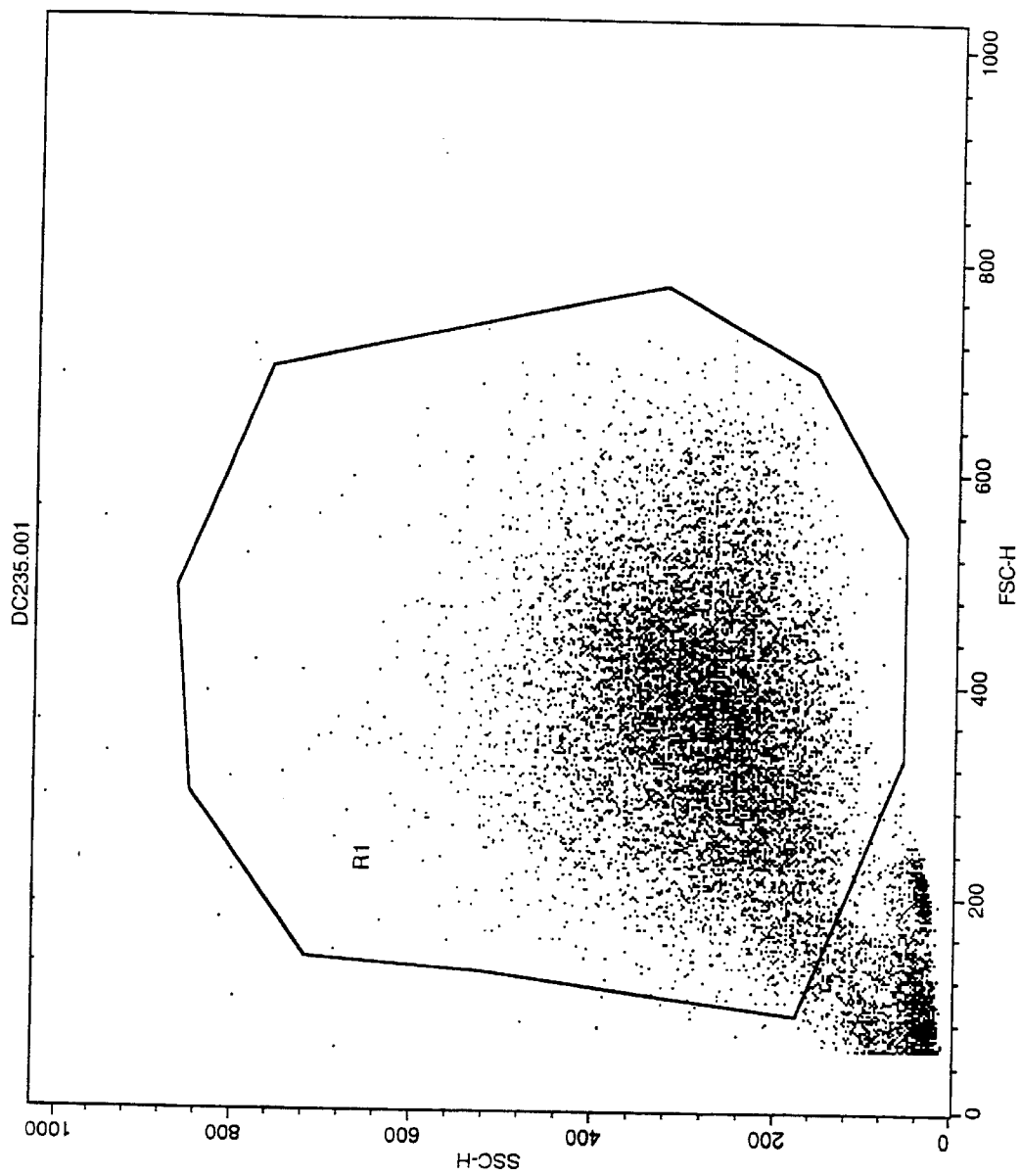
FIG. 8 shows a population of cells analyzed by forward and side scatter on a FACScan.
Figure 9:
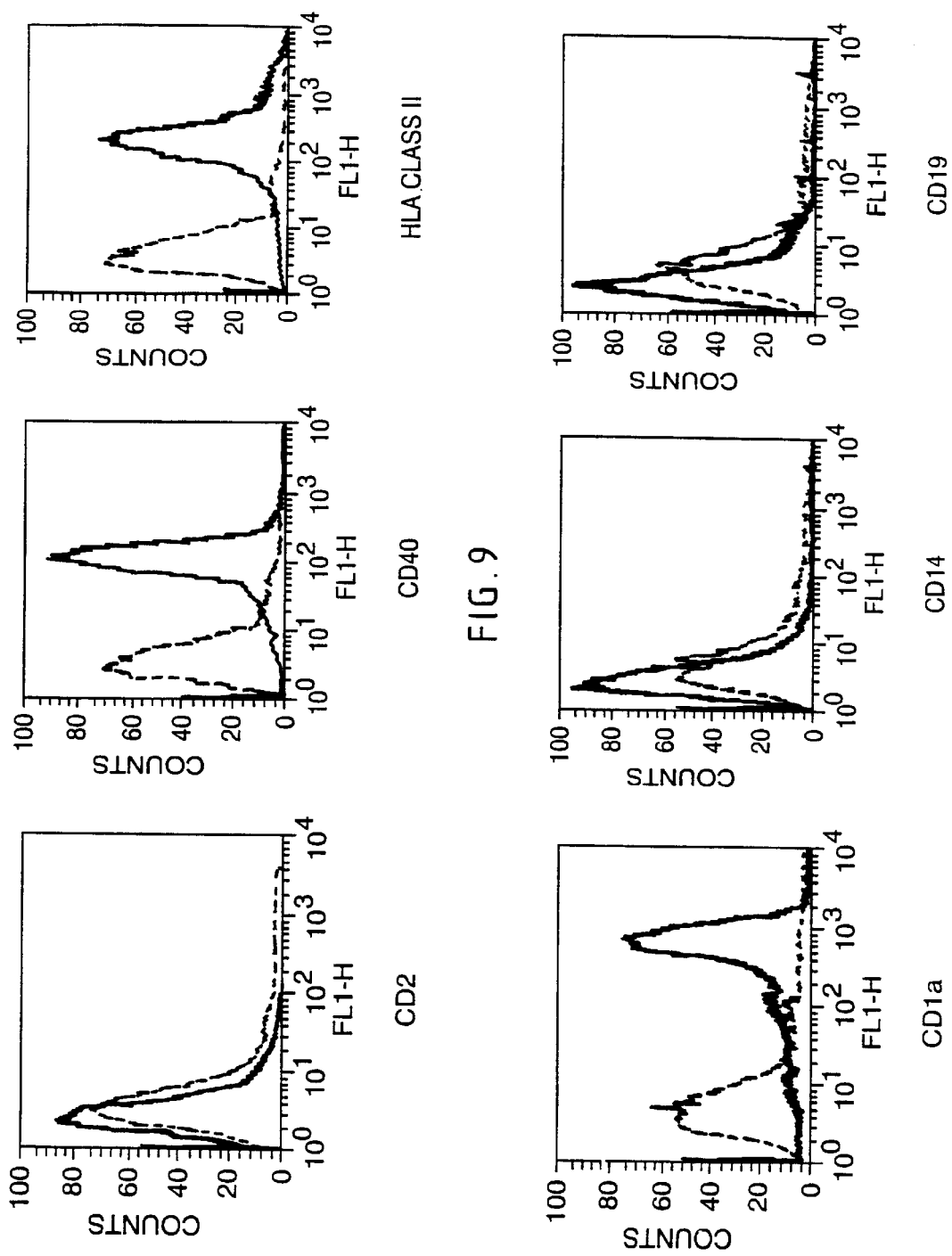
FIG. 9 shows dendritic cells analyzed for surface markers using FITC or PE labeled antibodies specific for those markers and a Becton Dickinson FAC scan and some isotype negative control antibodies.

Human DC were provided as described by Romani et al. (J. Exp. Med. 1994 180:83–93). Briefly, human PBMC were prepared from Buffy coats by standard protocols known in the art. The PBMC were resuspended in DC medium (RPMI-1640, 10% FCS, 2 mM glutamine, 1% non-essential amino acids, 50CM β-mercaptoethanol, 10 units/ml penicillin, 100 μg/ml streptomycin) and were allowed to adhere to plastic tissue culture dishes. After 2 hours at 3 7° C., 5% $CO_2$ the nonadherent cells were removed, the adherent cells were gently washed and subsequently cultured with DC medium plus cytokines (GM-CSF (800 U/ml) and IL-4 (500 U/ml)). The cultures were fed with cytokines every second day of culture. After 6 to 7 days of culture the cells have the 'DC-like' surface markers which are known in the art to identify these cells. Typically, the population of cells is relatively homogeneous as analyzed by forward and side scatter on a FAC scan (FIG. 8) and the surface markers characteristic of these cells are as expected ($CD 14^-$, $CD19^-$, $HLA-DR^+$, $CD1a^+$, $CD40^+$; FIG. 9). In FIG. 9, dendritic cells were analyzed for surface markers using FITC or PE labeled antibodies specific for those markers. A Becton Dickinson FAC scan and some isotype negative control antibodies were used.

Transfection of DC

On day 6 of culture the cells are harvested and resuspended to $3.44 \times 10^5$ cells/ml in RAT medium (RPMI 1640, human serum albumin 1 mg/ml; human transferrin (partly saturated) 50 μg/ml). Using 24 well plates an appropriate amount of 10 mM chloroquine and 125 μl of complex is added to a single well but in such a way as the samples do not mix. 871 μl of DC in RAT (described above) is then added to the well. The complex is made as described in the section entitled "Preparation of K6CL22-DNA complexes for PCS and zeta analysis and in transfection assays" except the plasmid pEGFP-N1 (Clontech) was used in place of pCMVβ. The plates are spun at 1100 rpm for 5 minutes and are incubated at 37° C., 5% $CO_2$ for a given time period. The cells are removed from the wells, harvested, resuspended in 1 ml DC medium plus cytokines per well and returned to the plate for incubation at 37° C., 5% $CO_2$ (NB: depending on the length of the transfection period some of the cells may have adhered to the well. The adhered cells are left in the well while the suspension cells are washed.) The length of the incubation prior to harvesting (expression time) can be varied. Each well is then harvested, cytospun onto a slide and transfected cells are visualized using a LEICA fluorescence microscope (positive cells appear green). The number of positive cells per slide are counted. If there are an excessive number of positive cells either a known fraction of the cells are cytospun or a known fraction of the slide area covered by cells is counted. Thus, the total number of transfected cells can be determined.

Figure 10:
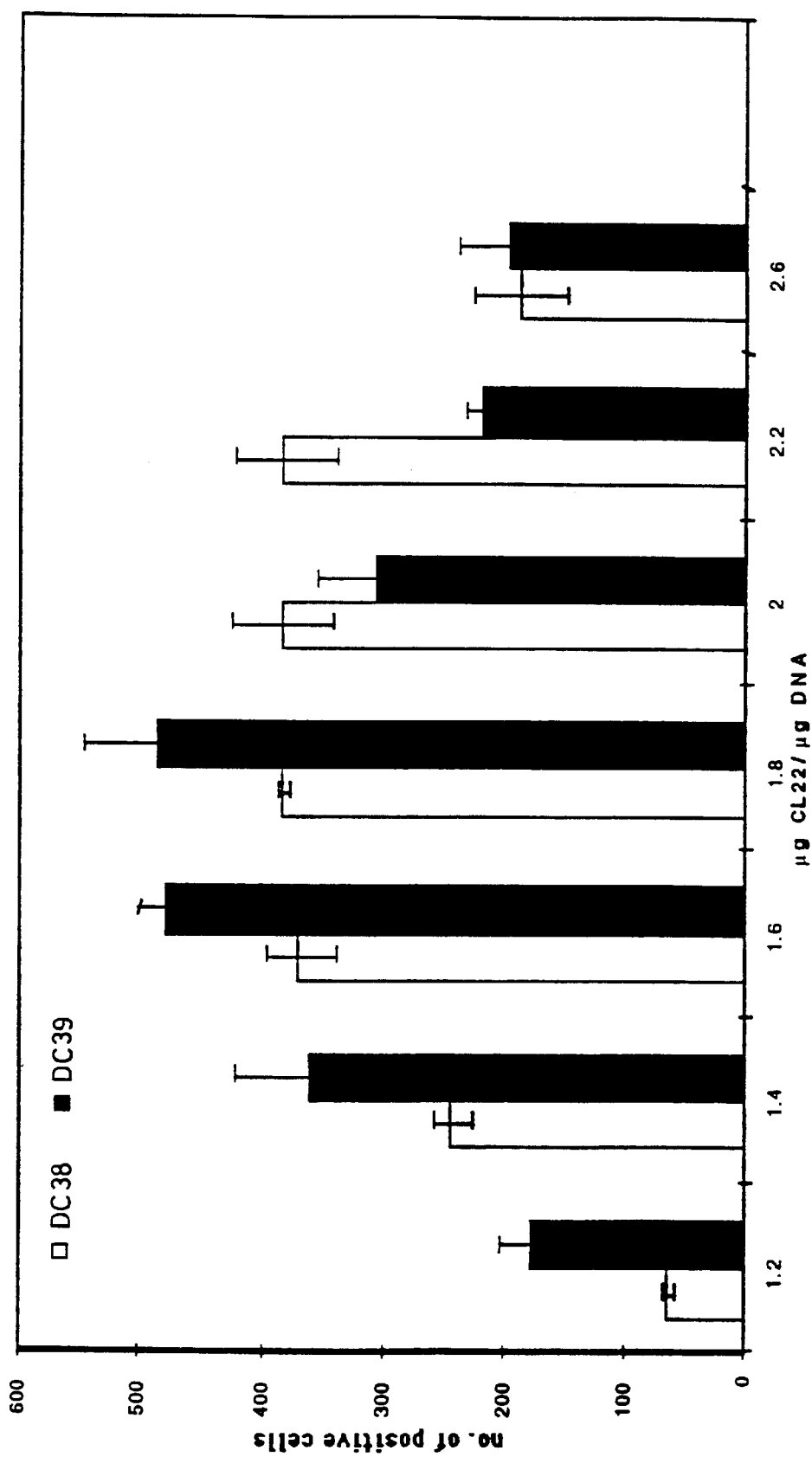
FIG. 10 shows a graph of transfection efficiency wherein the peptide/DNA ratio was varied between 1.2 and 2.6.

FIGS. 10–14 show results of transfections for two different preparations of dendritic cells in which certain variables were tested in order to determine the effect on transfection efficiency. In FIG. 10, the peptide/DNA ratio was varied between 1.2 and 2.6, with the highest transfection efficiency being obtained at ratios in the range of 1.4–2.0. The transfections were performed in 40 μM chloroquine, with a transfection time of 4 hours and an expression time of overnight.

Figure 11:
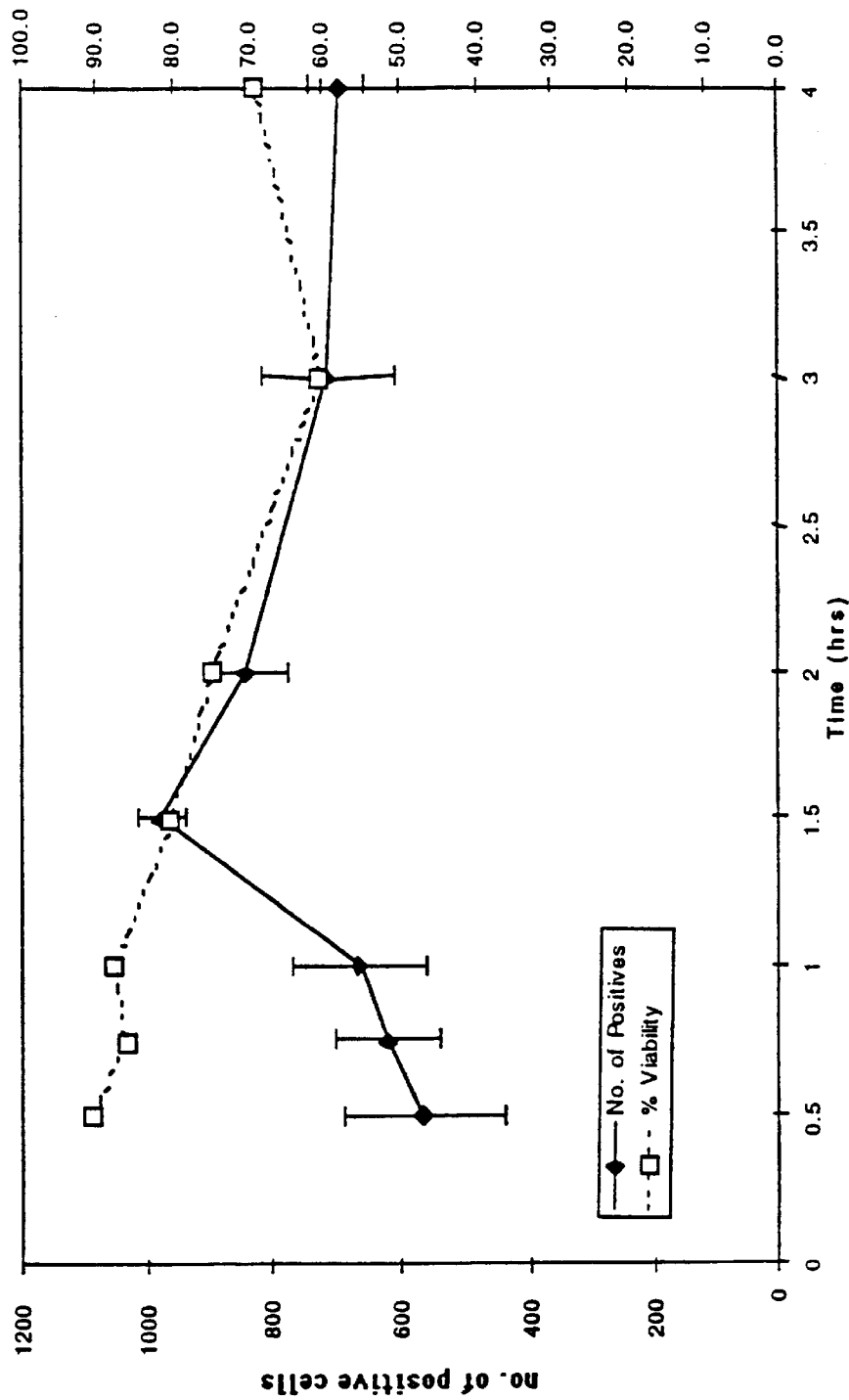
FIG. 11 shows results of transfections of dendritic cells with a variable transfection time.

FIG. 11 shows results of transfections of dendritic cells with a variable transfection time. Dendritic cells were transfected with 2 μg K6CL22/μg DNA for various transfection times, as indicated, in 40 μM chloroquine. The expression time was overnight and the cell viability was also assessed, at the time of harvest, by trypan blue staining.

Figure 12:
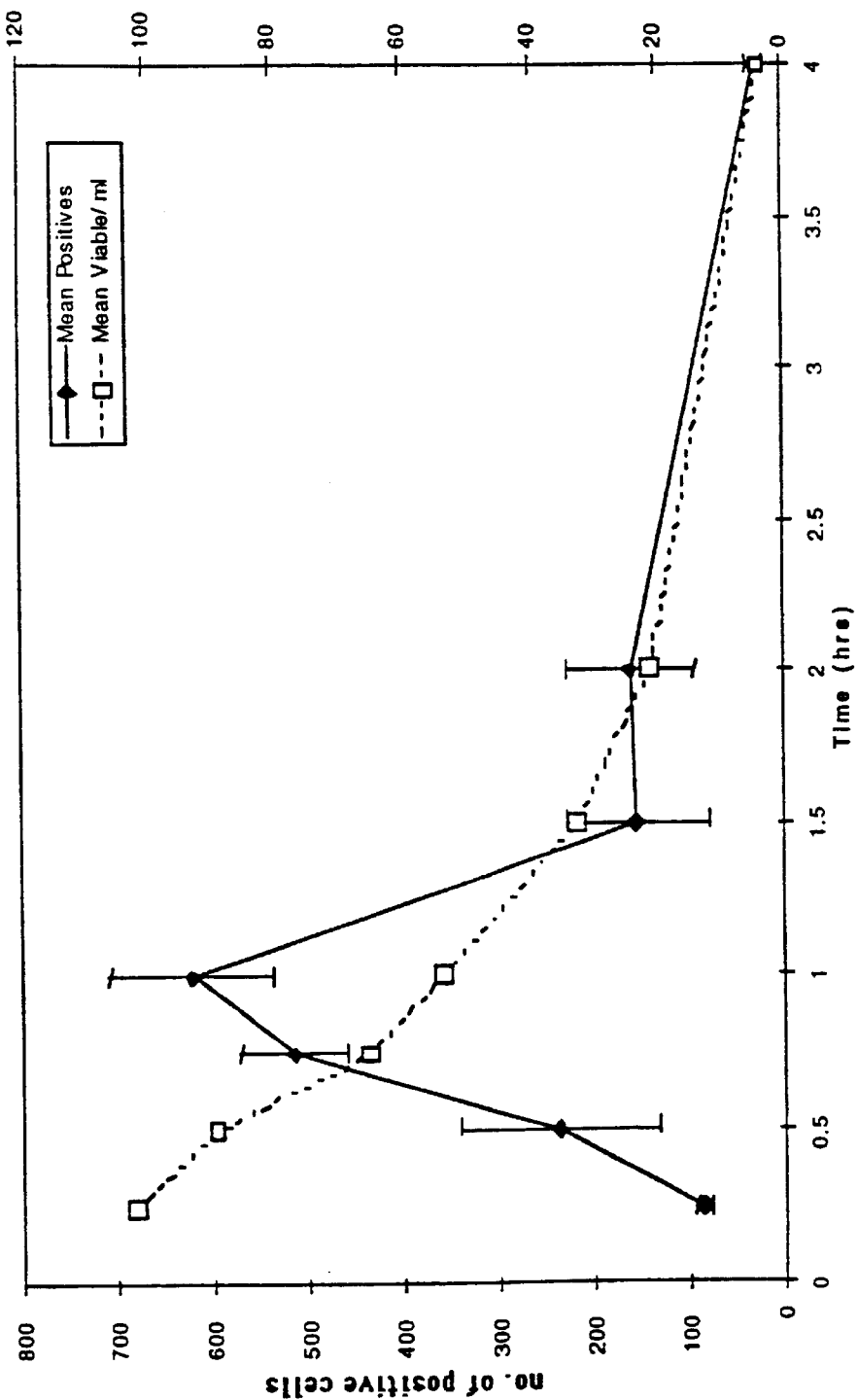
FIG. 12 shows results of transfections of dendritic cells with a variable transfection time.

FIG. 12 shows results of transfections of dendritic cells with a variable transfection time. Dendritic cells were transfected with 2 μg K6CL22/μg DNA for various transfection times, as indicated, in 80 μM chloroquine. The expression time was overnight and the cell viability was also assessed, at the time of harvest, by trypan blue staining.

Figure 13:
FIG. 13 shows results of transfection efficiency in which the time of transfection is varied.

FIG. 13 shows results of transfection efficiency in which the time of transfection is varied. Transfection of dendritic cells was performed using 2 μg K6CL22/μgDNA in the presence of 40 μM Chloroquine. Transfection efficiency is calculated as (total number of positive cells divided by total number of viable cells)×100. Expression time was overnight.

Figure 14:
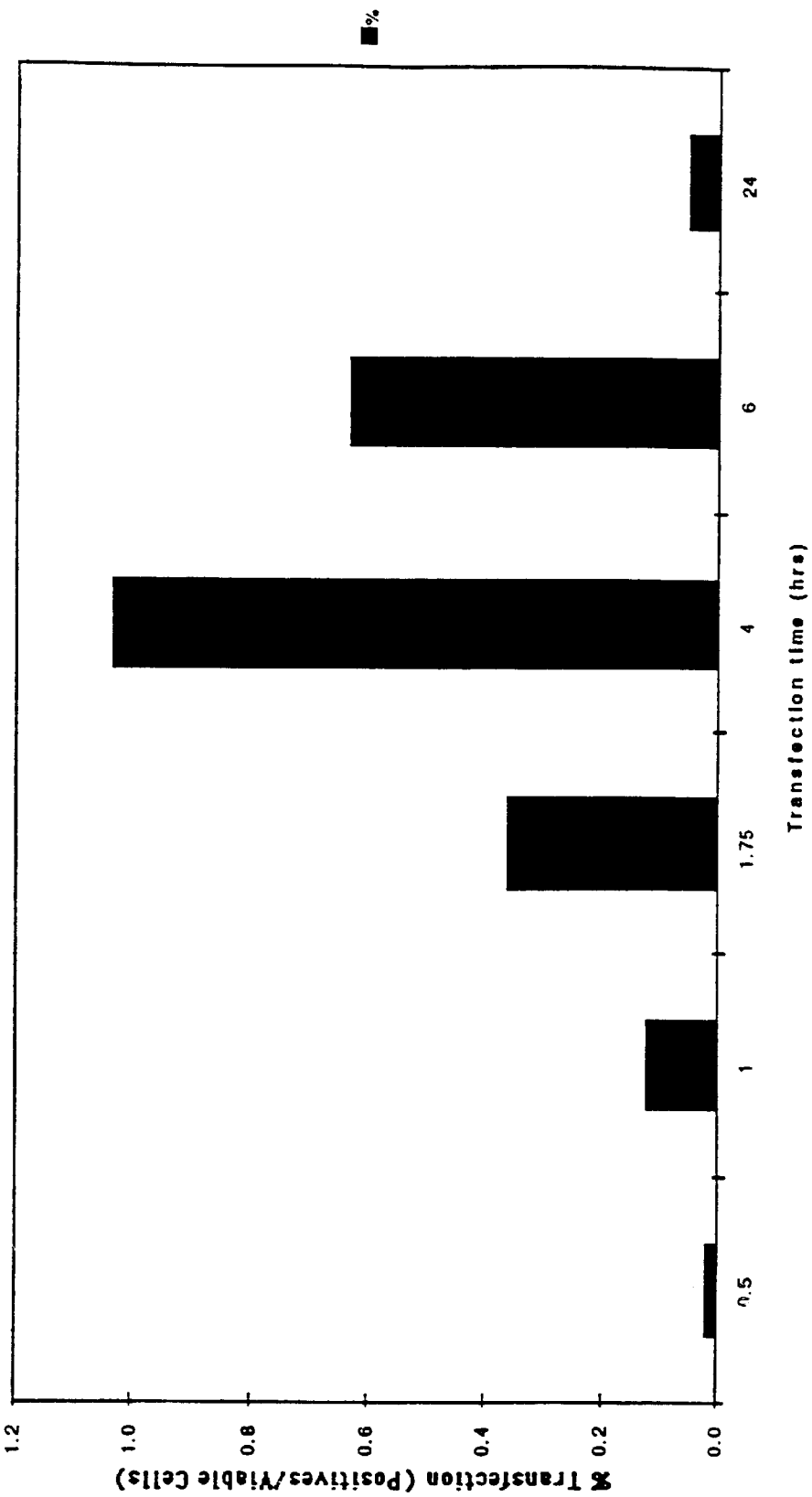
FIG. 14 shows the effect of transfection time on transfection efficiency using 2 μg K6CL22/μg DNA and 20 μM chloroquine.

FIG. 14 shows the effect of transfection time on transfection efficiency using 2μg K6CL22/μg DNA and 20 μM chloroquine. Transfection efficiency is calculated as (total number of positive cells divided by total number of viable cells)×100. Expression time was overnight.

EXAMPLE 3

Transfection of Cos 7 Cells with K6CL22/DNA

Figure 15A:
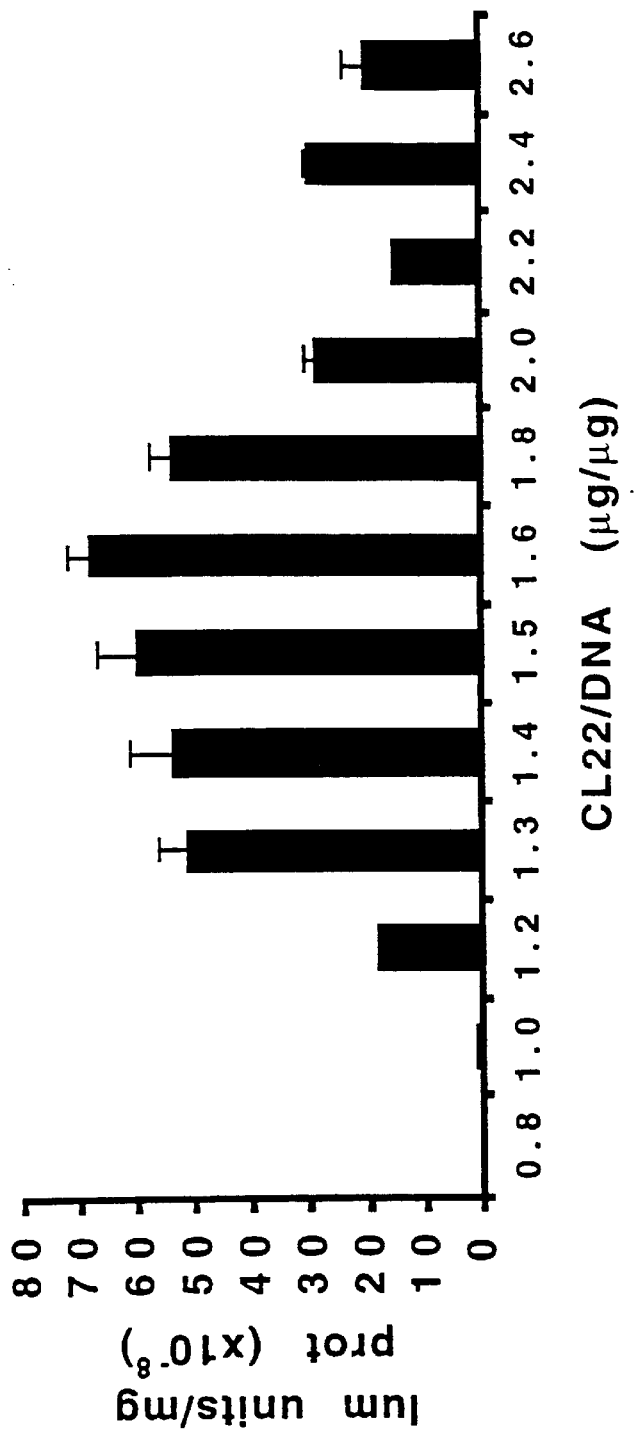
FIG. 15a shows luminescence and X-gal results of Cos7 cell transfection at different K6CL22/DNA ratios.

Transfection was performed as described above in "Preparation of K6CL22-DNA Complexes for PCS and Zeta analysis and transfection assays" and in which K6CL22/DNA (pCMVβ) was prepared in HEPES buffer. FIG. 15*a* and *b* show luminescence and X-gal results of transfection at different K6CL22/DNA ratios.

EXAMPLE 4

Transfection of Cos 7 Cells with K6CL22/DNA

Figure 16A:
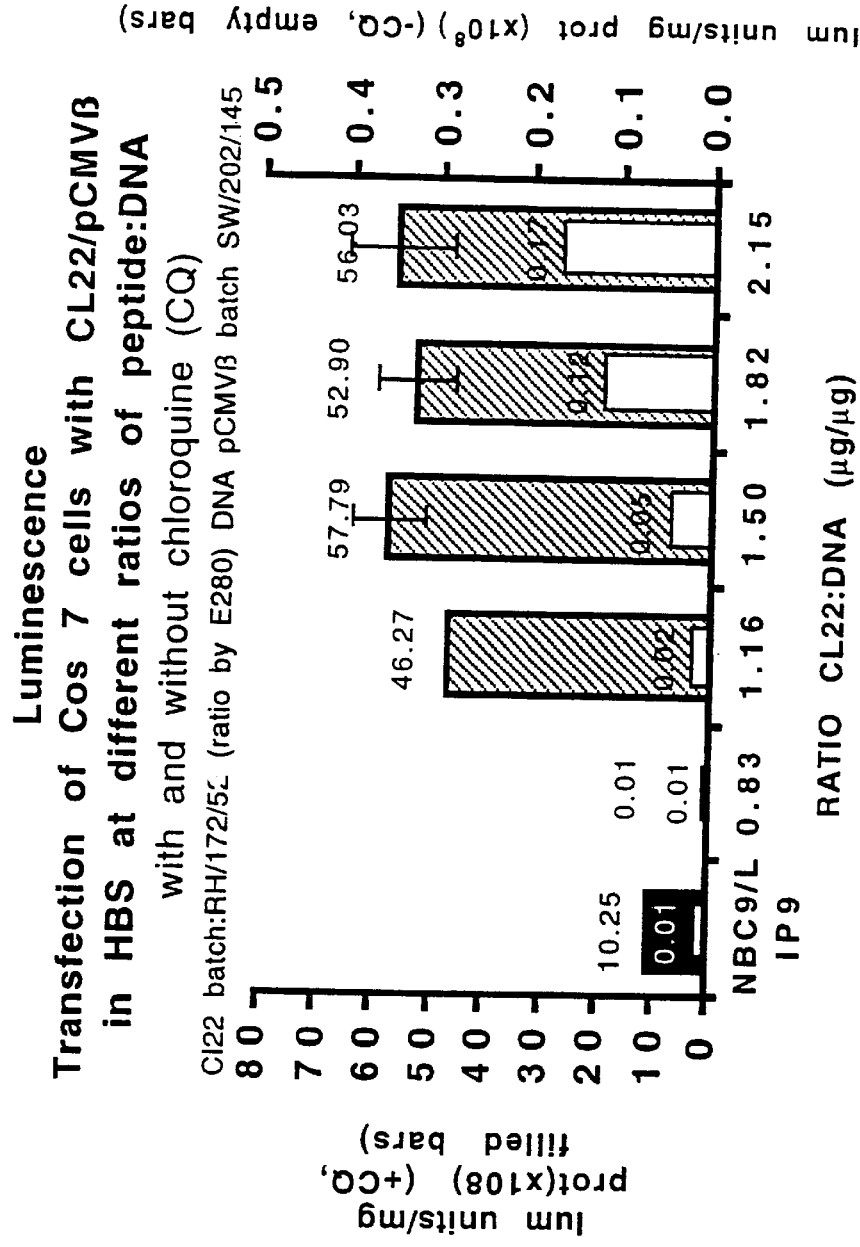
FIG. 16a shows luminescence and X-gal results of Cos7 cell transfection at different K6CL22/DNA ratios.

Transfection was performed as described above in Example 3 in which K6CL22/DNA (pCMVβ) was prepared in HBS (HEPES buffered saline), with and without chloroquine (CQ). FIG. 16*a* and *b* show luminescence and X-gal results of transfection at different K6CL22/DNA ratios. The presence of chloroquine (at 120 μM) is indicated by the hatched bars.

EXAMPLE 5

Transfection of KLN 205 Cells with K6CL22/DNA

Figure 17A:
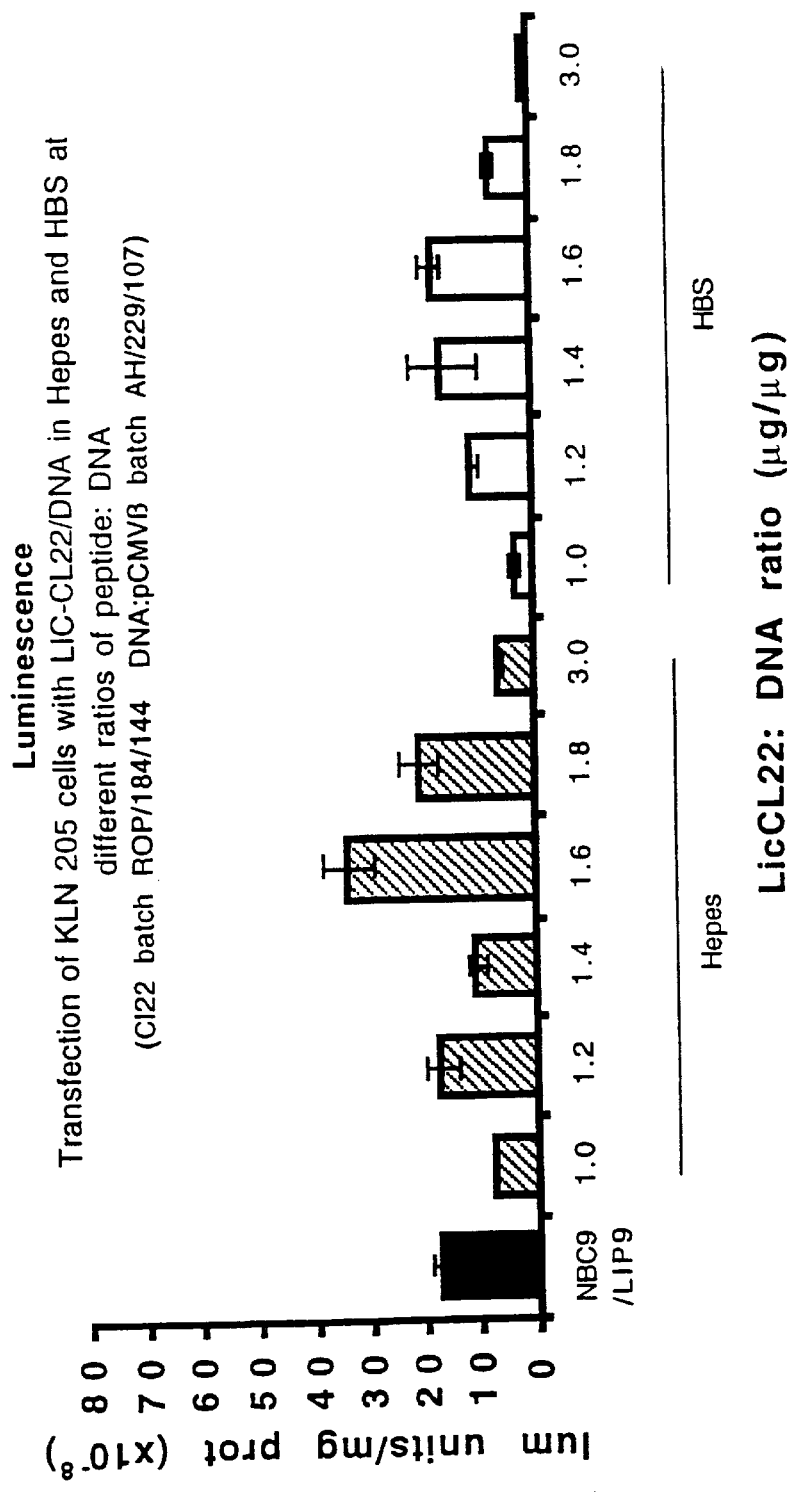
FIGS. 17a and b show the transfection results using KLN 205 cells.

KLN 205 cells (mouse squamous cell carcinoma with epithelial characteristics, A.T.C.C. CRL1453). Transfection was performed as described above in Example 3 in HEPES buffer or in HBS, as indicated, at different lic-K6CL22/DNA (pCMVβ) ratios. FIG. 17*a* and *b* show the transfection results.

EXAMPLE 6

Transfection of Cos 7 Cells and Chinese Hamster Ovary Cells with K6CL22/DNA

FIG. 18 shows transfection results in which K6CL22/DNA (pCMV) was used to transfect Cos7 cells or CHO cells, as indicated, in the presence of 120 μM chloroquine. Cells were seeded at $5 \times 10^5$ cells/well in 2 ml medium, otherwise transfection was carried out as described above in Example 3.

EXAMPLE 7

Figure 19:
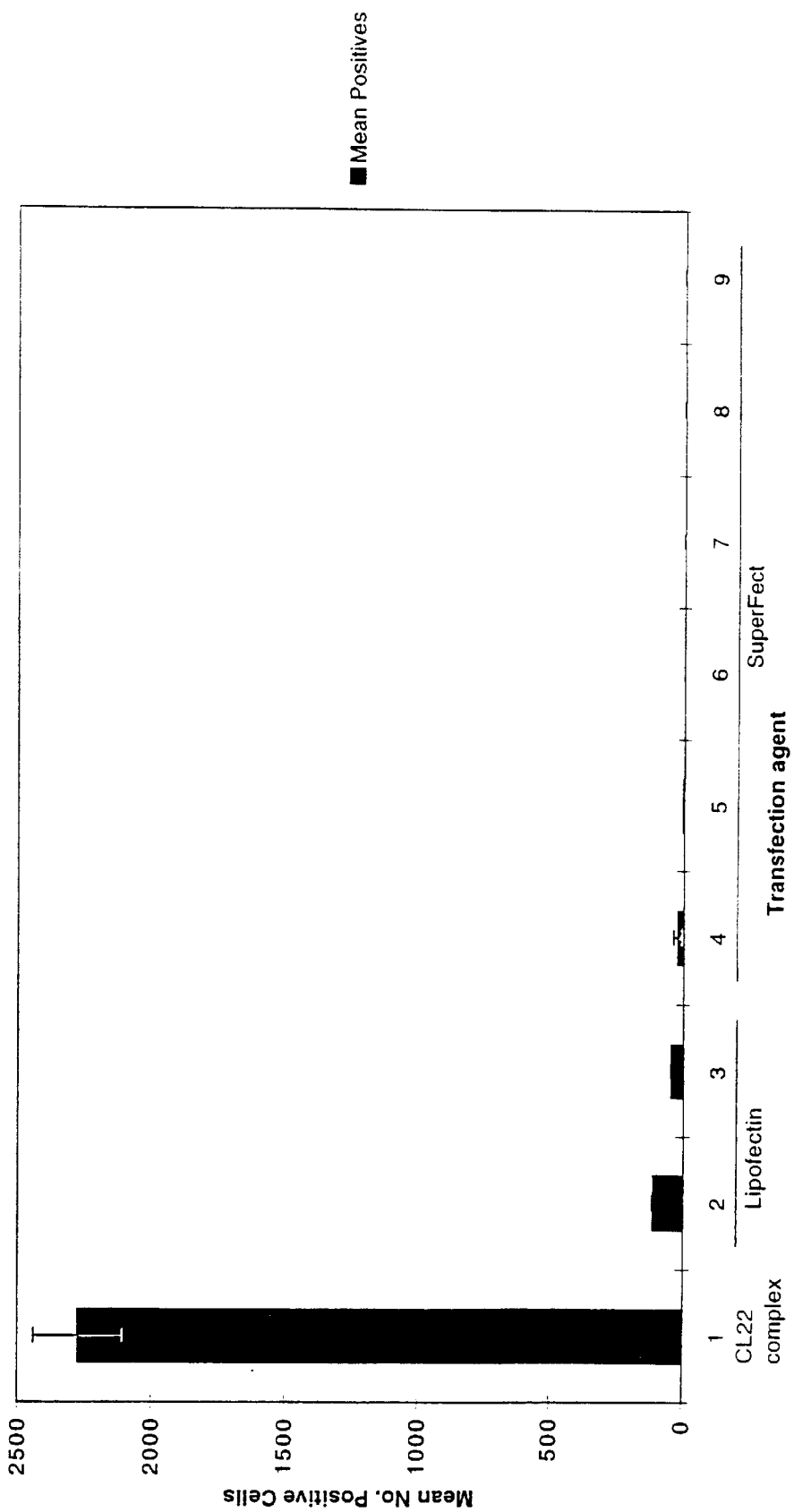
FIG. 19 presents a comparison of CL22 based delivery complexes with Lipofectin (Gibco-BRL) and SuperFect (Qiagen).

Comparison of K6CL22 Transfection Complex and Lipofectin and Superfect with Respect to Efficiency of Transfection of Dendritic Cells Equal numbers of dendritic cells from the same preparation were transfected with the following agents, all the cells were then cytospun and the number of positive cells counted by visualization using fluorescence microscope. The transfection agents were; 2 μg K6CL22/μg pEGFP-N1 delivery complexes with 80CM chloroquine and a transfection time of 1 h (1); Lipofectin used at 2.5 μg pEGFP-N1/10 μl Lipofectin (2) and 10 μg pEGFP-N1/20 μl Lipofectin (3); SuperFect used at various amounts of pEGFP-N1/ SuperFect-1 μg/2 μl (4), 1 μg/4 μl (5), 1 μg/8 μl (6), 2.5 μl/5 μl (7), 2.5 μl/10 μl (8) and 2.5 μl/20 μl (9). The transfections with Lipofectin were carried out as described in the product protocol (Gibco, BRL) with a four hour transfection period followed by three fold dilution and an overnight expression period. The transfections with SuperFect were carried out as described in the product protocol (Qiagen) again with an overnight expression period. The results, shown in FIG. 19, are the means of at least triplicate points (except 2 which is the mean of duplicate points) and the error bars are standard errors.

EXAMPLE 8

Comparison of Monomer and Dimerized Preparations of K6CL22

Blocking of Cysteine Thiol of K6CL22 using N-Ethylmaleimide (NEM) 6.0 mg (1.5 μmol.) K6CL22 (batch 42A) was dissolved in 0.90 ml PBS and the cysteine reduced by adding 3.0 mg (20 μmol.) DTT in 0.10 ml water. After 2 h at room temperature the DTT was removed by gel filtration using a 1.6×30 cm column packed with Sephadex G25 Fine, and using 20 mM ammonium acetate, pH 5.0, as running buffer. The fractions containing peptide were pooled, lyophilized and 4.0 mg freshly reduced peptide made up to 1.0 ml in PBS. The molar ratio of free thiol to peptide, as determined by an Ellman's assay (ref: Hermanson, GT (1996) "Bioconjugate Techniques" pp.88–90. (Published by Academic Press Ltd, London), was 0.88.

To 900 μl 4.0 mg/ml freshly reduced K6CL22, 100 μl water containing 0.8 mg (6.4 μmol) NEM was added. After 3 h incubation at 25° C. an Ellman's assay failed to detect the presence of free thiols. The excess NEM was removed by gel filtration, as described above, before lyophilization to give 2.1 mg thiol blocked peptide. Analysis by MALDI-TOF mass spectrometry gave an observed molecular weight of 4227.8 (expected MW 4227.0) for the blocked peptide; there was also a minor peak corresponding with the mass of the unblocked peptide, which may have been due to thiol deprotection during analysis.

Disulphide Formation to Give K6CL22 Dimers

To 1.0 ml of 5.0 mg/ml free thiol containing K6CL22 peptide in water was added 1.0 ml 0.1 M sodium borate, pH 8.0. The cysteine thiols were left to oxidize at 25° C. in a vial left open to the air. The progress of dimerisation was followed by observing the change in original retention time of the peptide by capillary electrophoresis. After 16 h the peptide was judged to have dimerised completely. Addition of 10 mM DTT to a peptide subsample reversed the observed shift in retention time. Dimer formation was also confirmed by gel filtration analysis using a Superdex Peptide (HR10/30) column. Finally, the sodium borate salt was removed by gel filtration in ammonium acetate followed by lyophilization, as described previously.

SDS PAGE analysis

Figure 21:
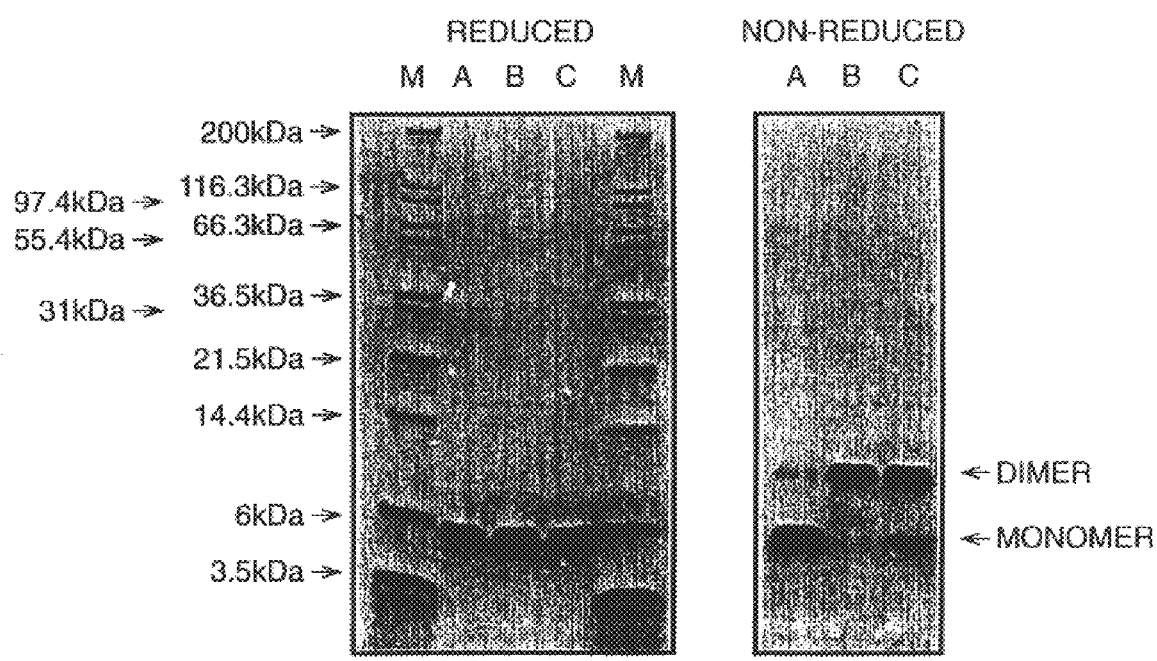
FIG. 21 presents a polyacrylamide gel of reduced and non-reduced CL22.

Samples of reduced and alkylated (blocked) K6CL22, and two batches of completely oxidized (dimerised) K6CL22 were analyzed by SDS-PAGE. 0.5μg/lane of each sample was loaded in reducing and non reducing sample buffer onto a 16% tris-tricine gel (Novex) and electrophoresed for 1 h 35 min. At 125v constant voltage. The gel was stained with coomassie blue. FIG. 21 shows the gel image.

The analysis demonstrates that under non-reducing conditions (sample A) the reduced and alkylated batch of K6CL22 is primarily monomer, whilst the oxidized batches (samples B and C) are dimerised. Under reducing conditions, all samples are monomer, consistent with the primarily dimer being formed by a disulphide bridge.

Figure 20A:
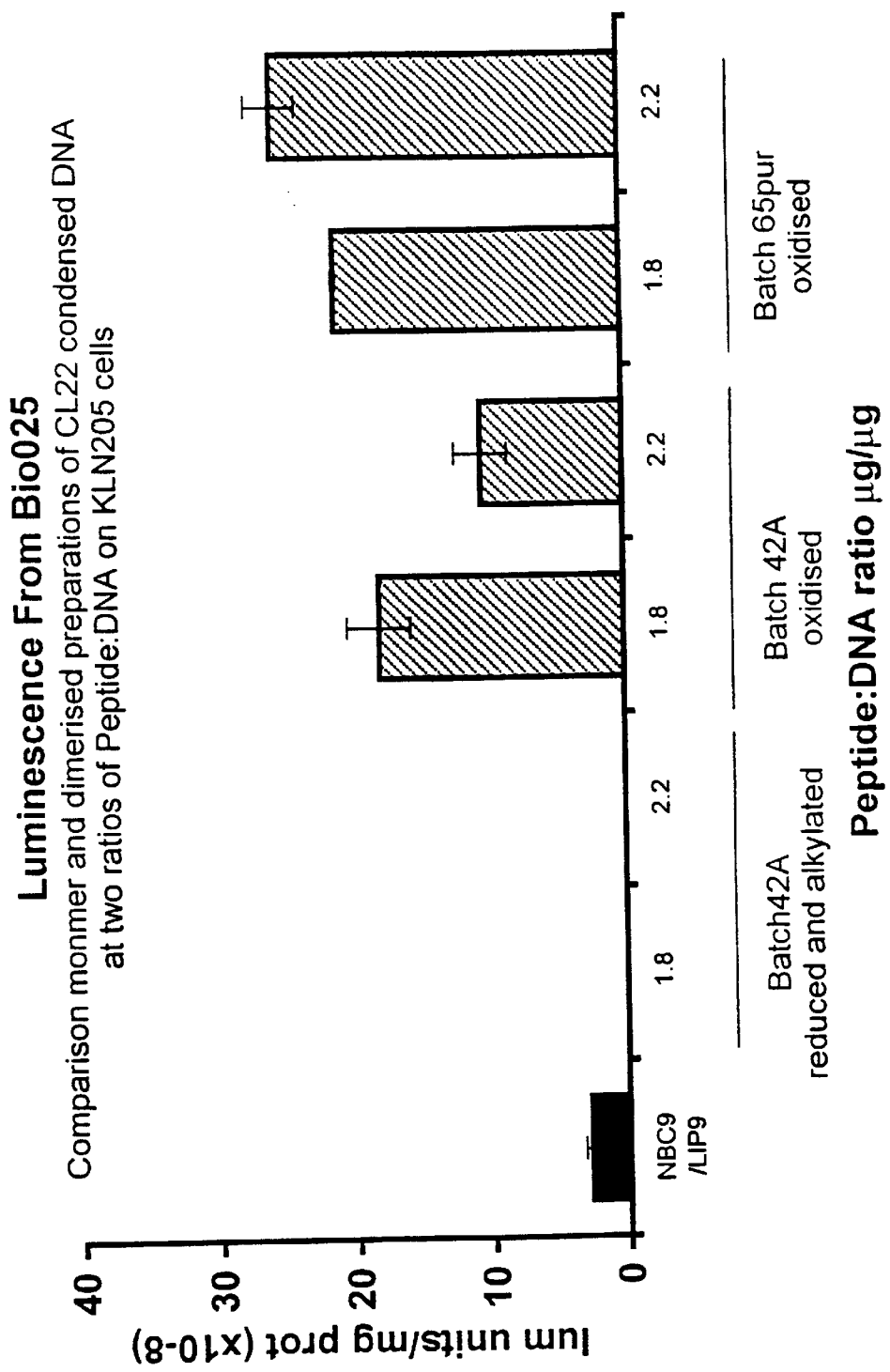

FIG. 20 shows luminescence and X-gal results after transfection of KLN 205 cells with K6CL22: DNA ratios as indicated, using reduced and alkylated versus oxidized forms of peptide, as indicated. The results demonstrate the oxidized form of the peptide produces a significantly higher efficiency of transfection than the reduced/alkylated form.

EXAMPLE 9

Various polypeptides according to the invention have been tested for transfection efficiency as described above. The results are shown in FIGS. 22–29. In the figures, "peptide ox" refers to the oxidised version of the peptide which is the disulphide linked dimer e.g. K6CL22 ox=K6CL22 dimer.

Figure 22:
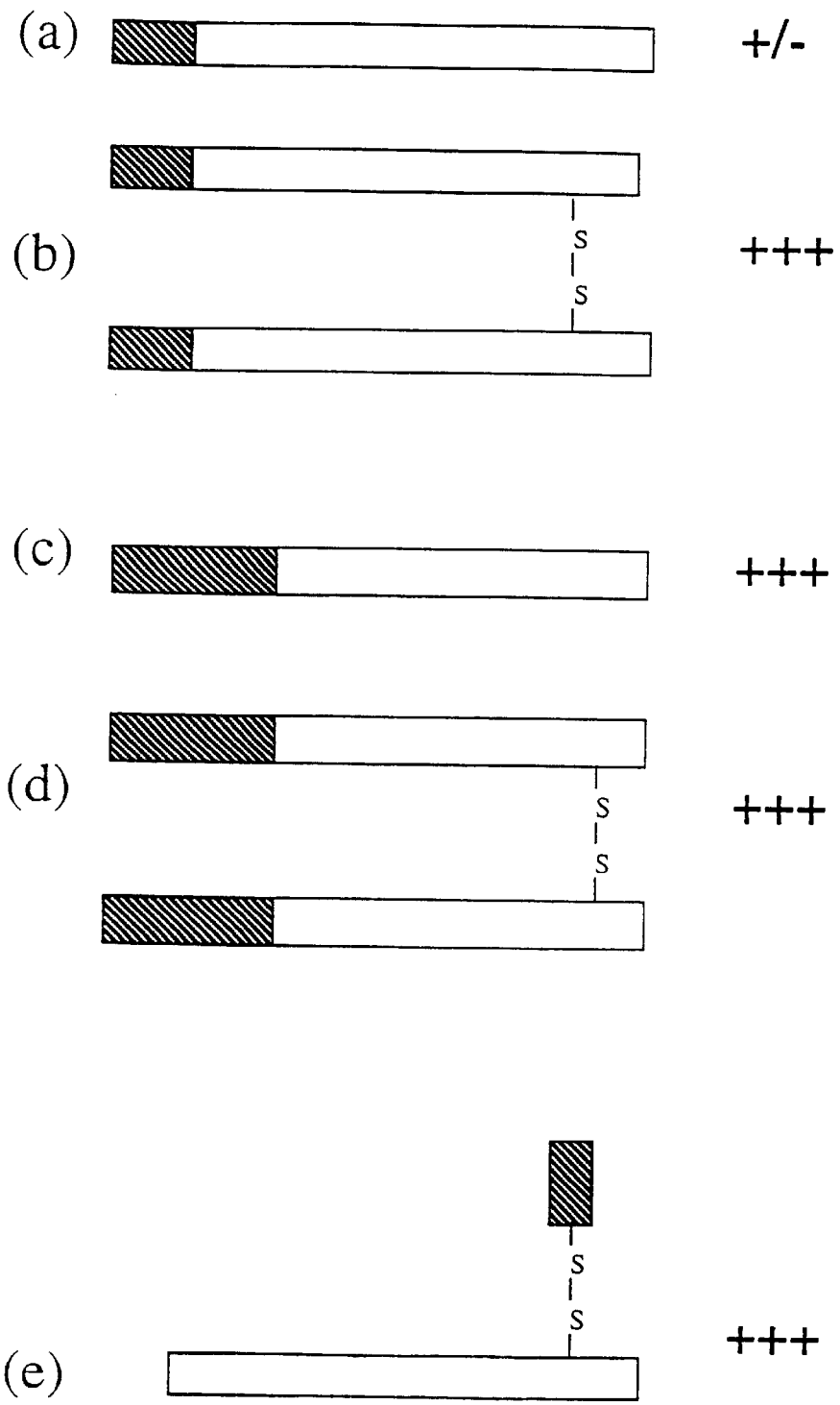
FIG. 22 is a schematic illustration of CL22 in monomer (a) and dimer (b) form; CL26 in monomer (c) and dimer (d) form; and NBC30 (monomer).
Figure 23:
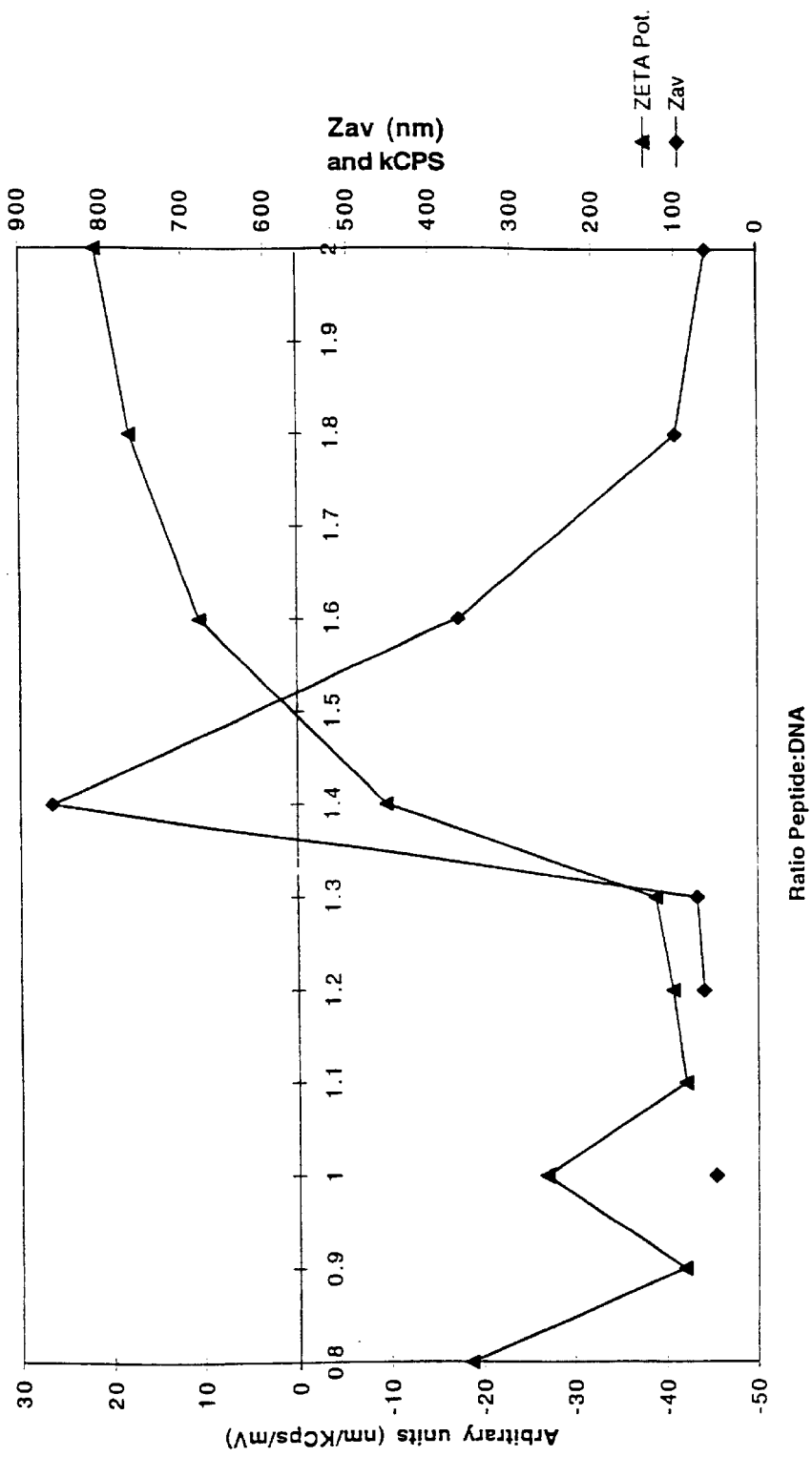
FIG. 23 is a graph in which the ratio of particle size and zet potential at different ratios of peptide:DNA.
Figure 24:
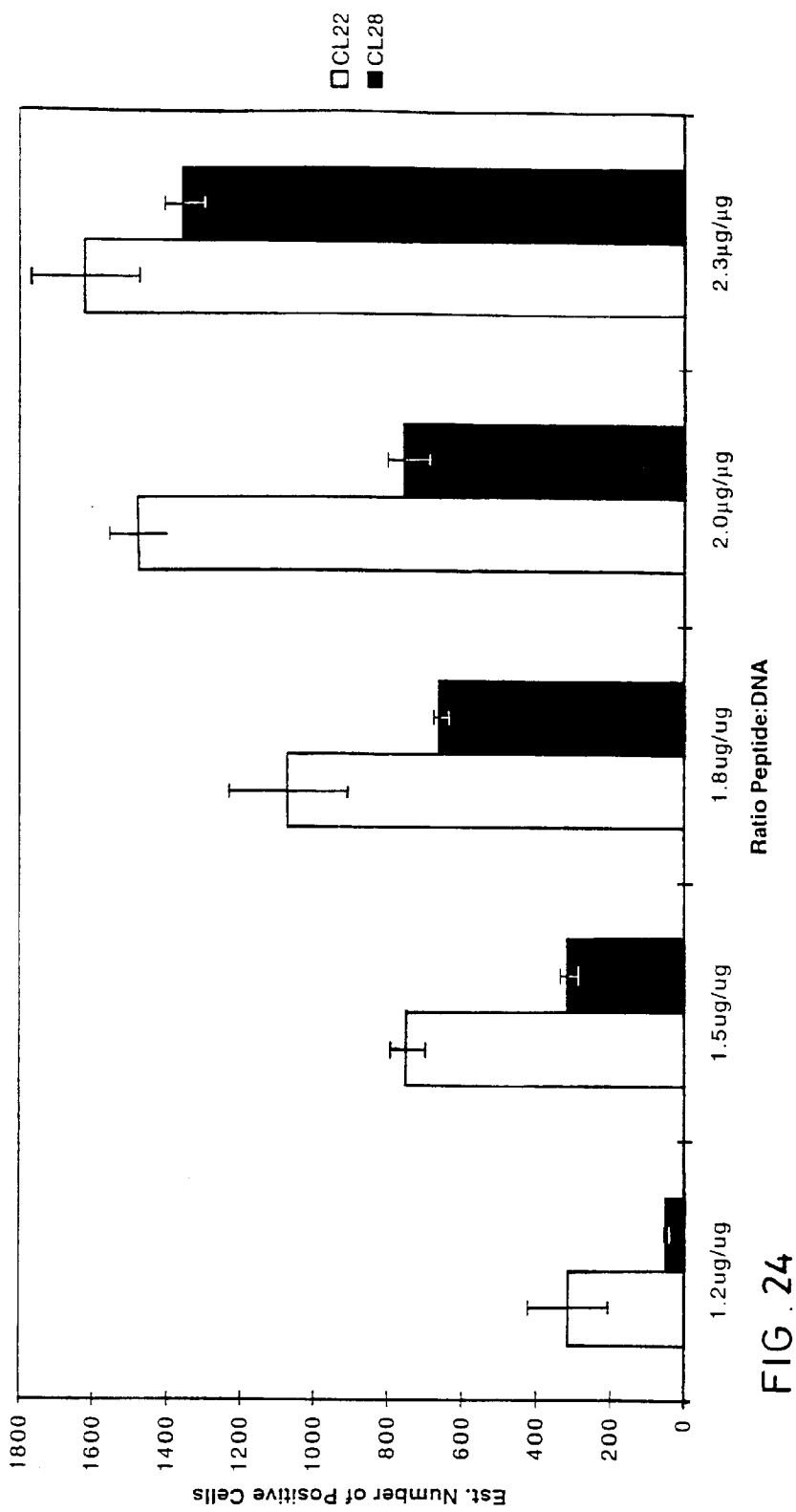
FIG. 24 is a bar graph of transfection efficiency as it relates to ratio peptide: DNA.
Figure 25B:
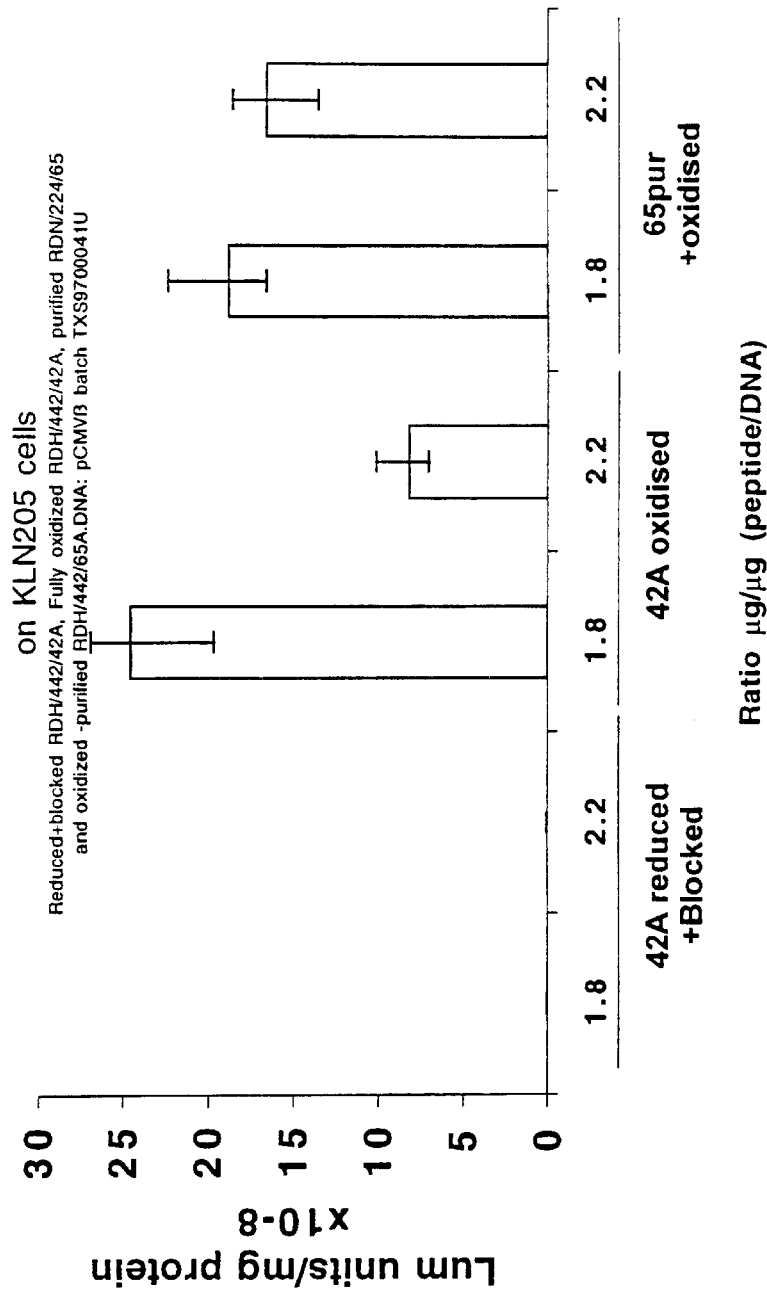
Figure 26A:
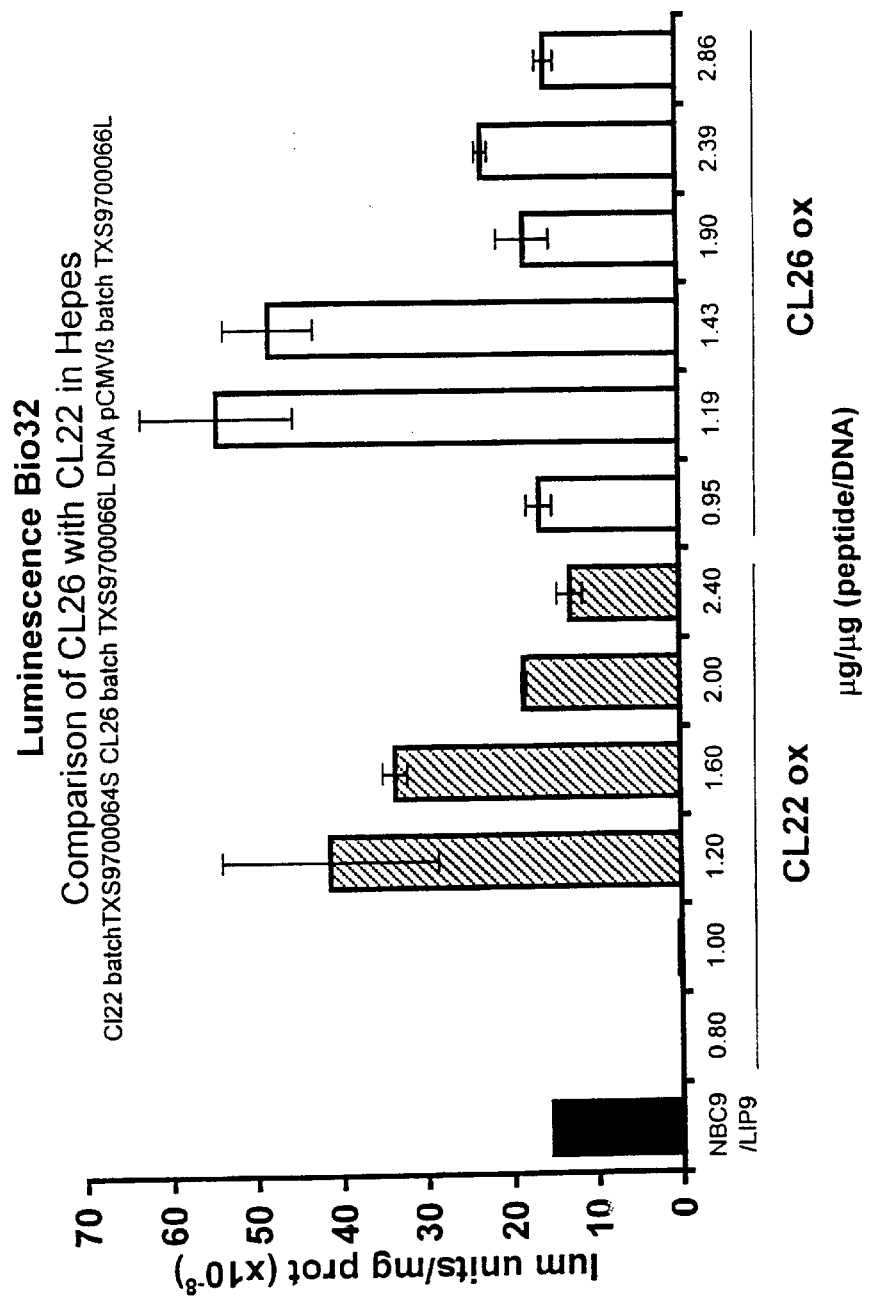
FIGS. 26A and 26B are bar graphs of transfection efficiencies of CL26 dimer (d) and CL22 dimer (d) transfection complexes.
Figure 26B:
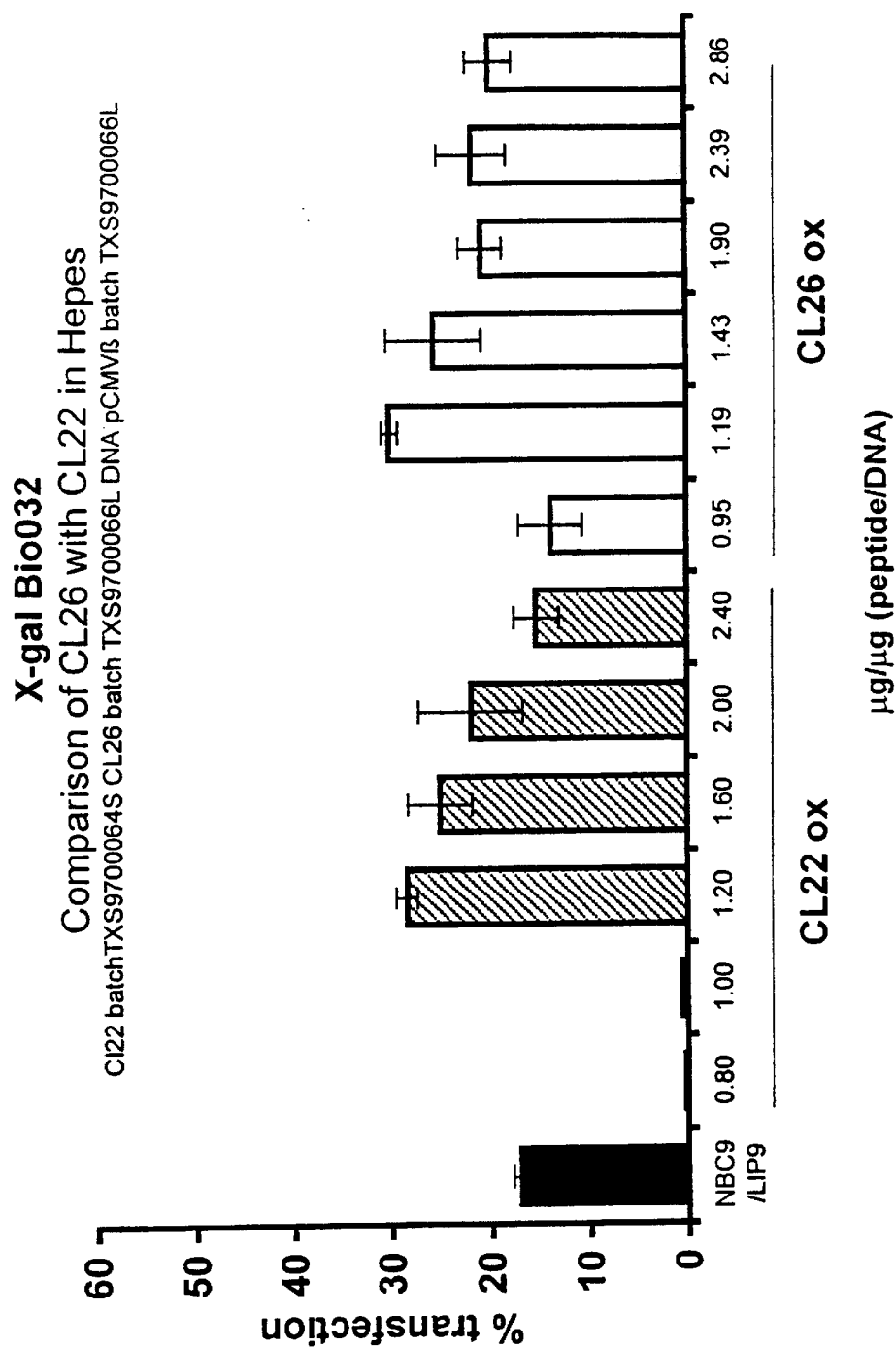
Figure 27B:
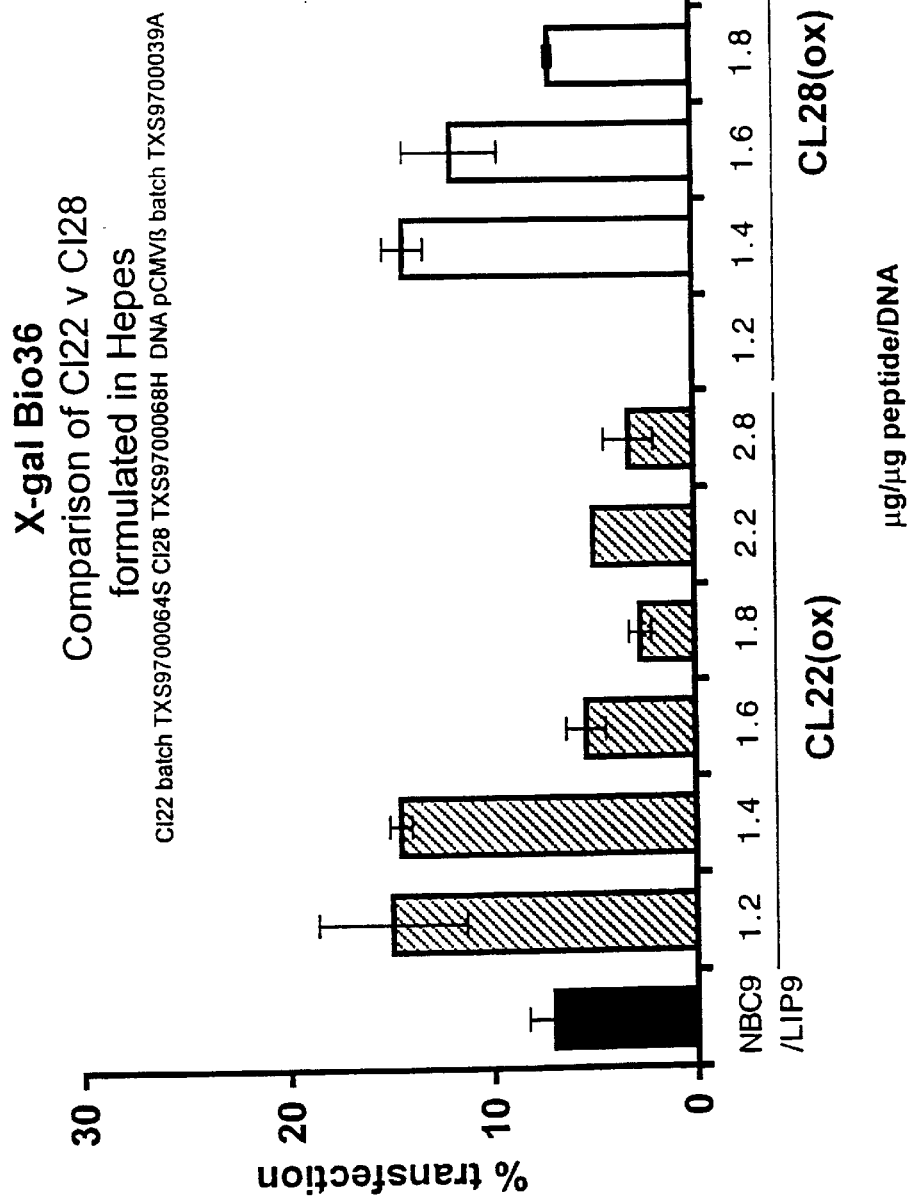
Figure 28A:
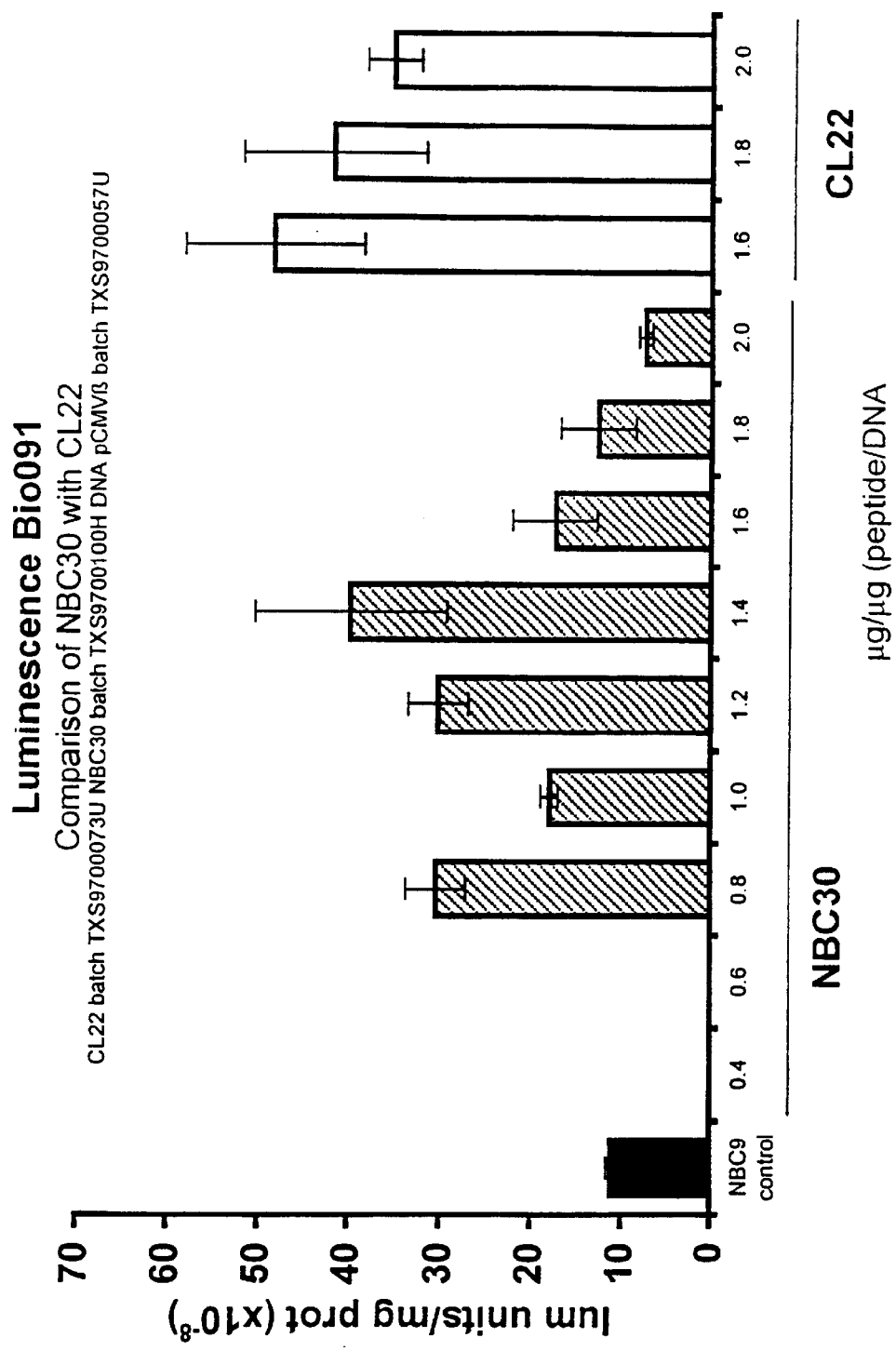
FIGS. 28A and 28B are bar graphs of transfection efficiencies of NBC30 and CL22 monomer transfection complexes.
Figure 28B:
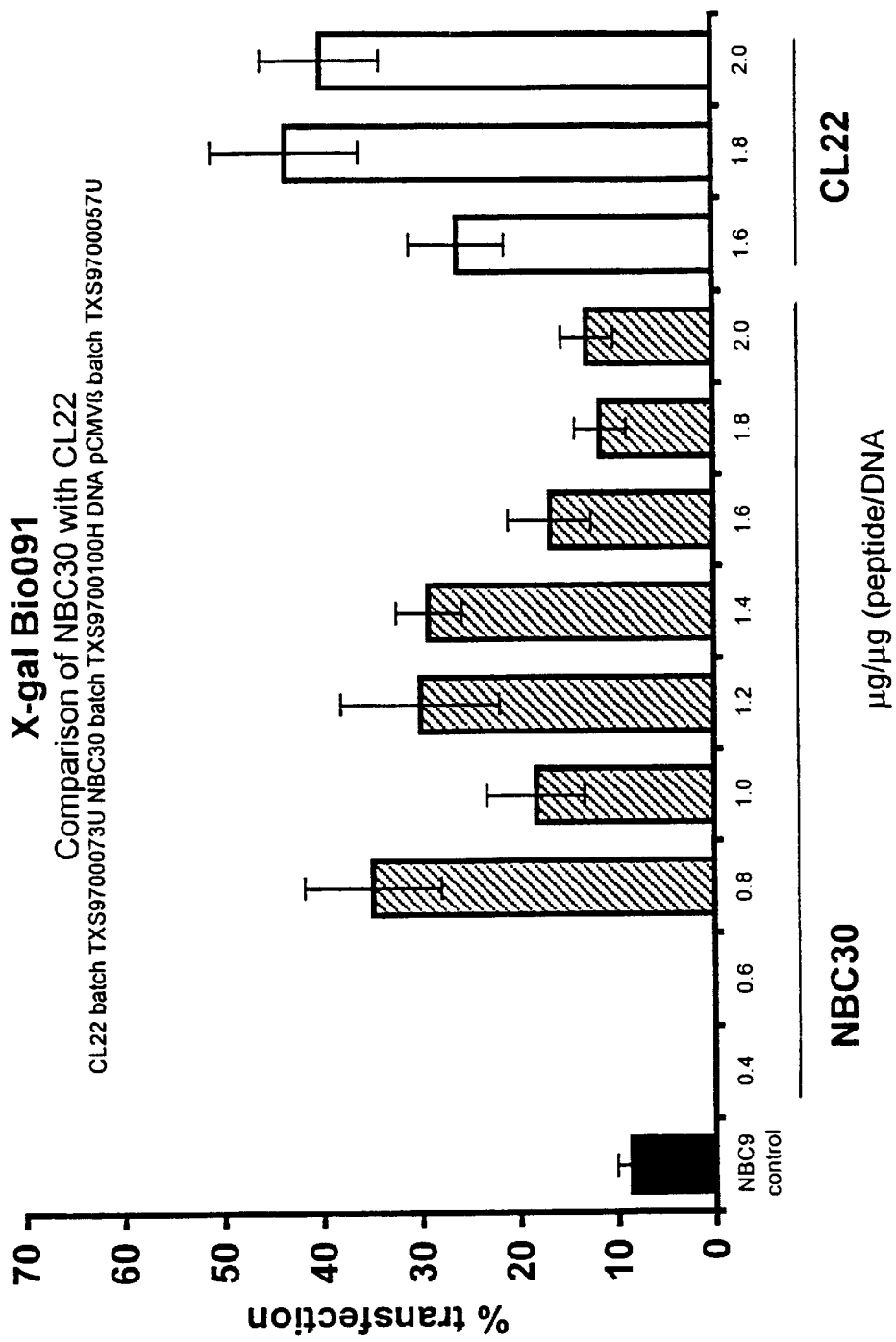
Figure 29:
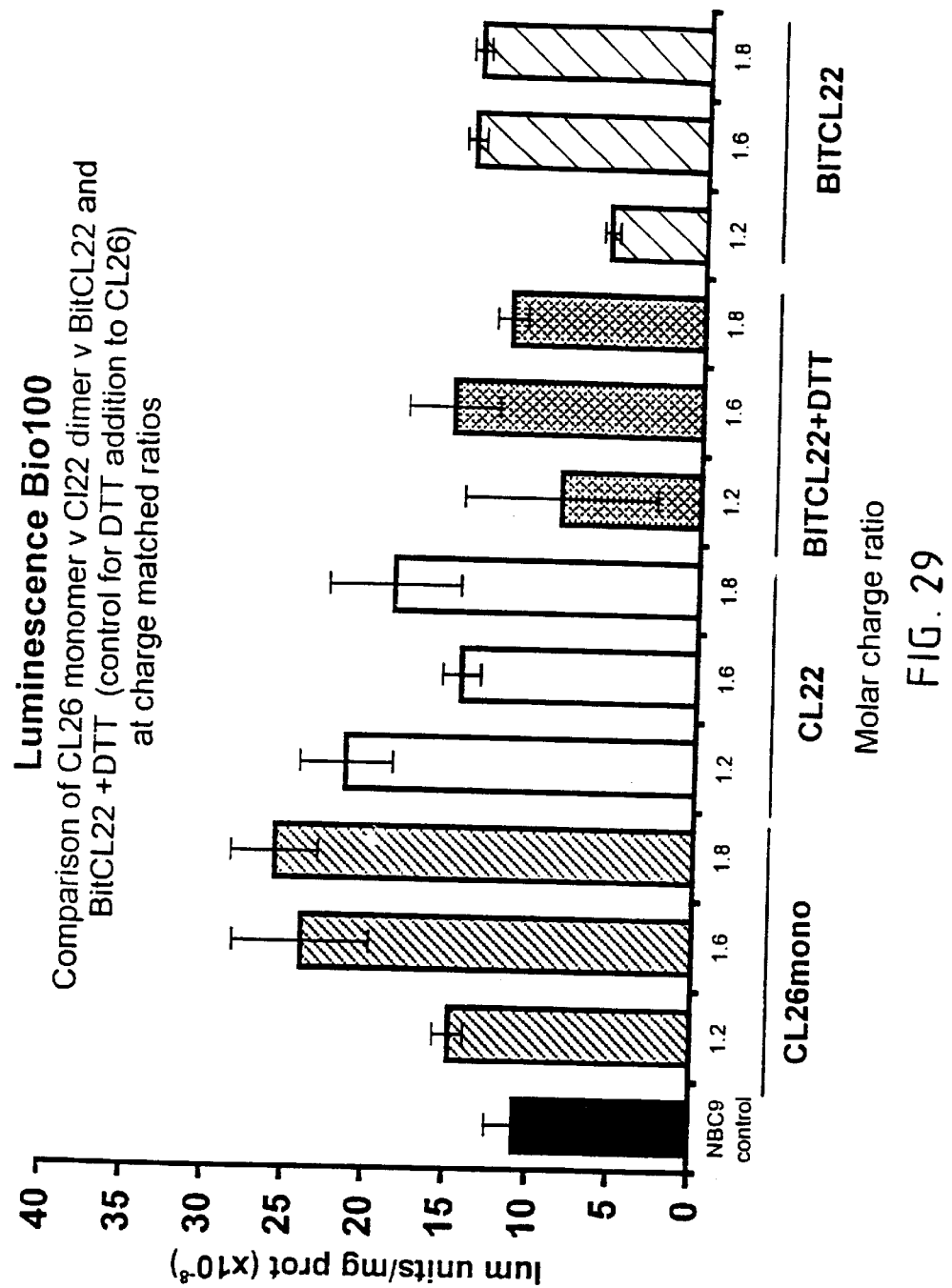
FIG. 29 is a bar graph of transfection efficiency of CL26 monomer and CL22 monomer transfection complexes.

In FIG. 22, a schematic illustration of K6CL22 monomer (a) and dimer (b) is shown. Transfection results demonstrate that K6CL22 monomer transfects poorly compared with K6CL22 dimer. FIG. 22 also shows a schematic illustration of CL26 in monomer (c) and dimer (d) form. Transfection results demonstrate that CL26 monomer and dimer transfect equally well. FIG. 22 is a schematic illustration of NBC30 (monomer). Transfection results demonstrate that NBC30 (monomer) and K6CL22 dimer transfect equally well. Transfection results are shown in FIGS. 23–29. The data in FIG. 29 shows a comparison of the CL26 monomer with the K6CL22 dimer. Also included in the figure are data on the K6CL22 dimer which contains a stable thioether bond in place of the disulphide (BITCL22).

EXAMPLE 10

Uptake of DNA Complexes by KLN 205 Cells

Example 10 demonstrates that KLN 205 cells can be transfected according to the method of the invention. This new example expands upon this observation by demonstrating that although K6CL22-complexed DNA is taken up as efficiently by these cells, as compared to DNA complexed with a polylysine peptide described in the prior art, the efficiency of transfection is far greater with K6CL22-complexed DNA. Furthermore, even when uptake of K6CL22-complexed DNA is less than that of a polylysine peptide, for example in the presence of FCS, the efficiency of transfection is still greater with K6CL22-complexed DNA.

KLN 205 cells were plated at a density of $1.5 \times 10^5$ cells per well in 6 well plates one day prior to the addition of DNA. Plasmid DNA (pCMVgal) was labeled with the fluorescent dye: YOYO-1 (Molecular Probes, Eugene, Oreg.) at a ratio of 1 dye molecule per 100 bp (i.e. 1.5 μl of a 10 μM YOYO-1 solution per jig of DNA). The DNA was diluted to 40 μg/ml with 10 mM HEPES, pH 7.3. Transfection complexes were formed between DNA and either K6CL22 or NBC32 (a polylysine peptide of sequence $TK_{36}YCG$) (SEQ ID NO:9) by mixing equal volumes of DNA solution (40 μg/ml) and peptide solution (K6CL22 at 90.3 μg/ml; NBC32 at 37.1 μg/ml) in 10 mM HEPES pH 7.3 to give a charge ratio of +2 and a final DNA concentration of 20 μg/ml. The transfection complex solution was left for 1 hour at room temperature before it was applied to the cells in EMEM/120 μM chloroquine with or without FCS at a DNA concentration of 2 µg/well (i.e. 100 µl of complex added to 900 µl medium for one well). After 4 hours of incubation at 37° C. the cells were washed twice with PBS and harvested with Trypsin/EDTA. The cell associated fluorescence was analyzed using a FACScan (Becton Dickinson). FIG. 30 shows the fluorescence of unlabeled cells (control; thin line), cells incubated with complexes in medium without FCS (bold line) and cells inclubated with complexes in medium containing FCS (dashed line). The average light units (% expressing cells) obtained under these conditions were 3000×10$^6$ RLU (35%) with K6CL22 in the absence of FCS, 77×10$^6$ RLU (5%) with K6CL2 in the presence of FCS, 29×10$^6$ RLU (1.5%) with NBC32 in the absence of FCS and 12×10$^6$ RLU (1.5%) in the presence of FCS.

The results of this experiment demonstrate that gene expression is higher in KLN 205 cells that have been transfected with K6CL22 complexed plasmid DNA as compared to KLN 205 cells that have been transfected with NBC32 complexed plasmid DNA. Thus, even under conditions where relatively minor amounts of DNA enter the cells, transfection with K6CL22 condensed DNA leads to high gene expression.

EXAMPLE 11

CL26 Enhances Transfection of FGF-targeted DNA Complexes

Recombinant human fibroblast growth factor (rFGF2/3) engineered to contain only one cysteine instead of two (Cys at position 96 was mutagenised to Ser) to allow for site specific peptide conjugation was obtained from Prizm Pharmaceuticals, San Diego, Calif.

CL26, (CL22 synthesised with an additional 6 lysine residues on the N-terminus) was conjugated to FGF (fibroblast growth factor) by the following method: 12 mg CL26 (2.5 µmol) was dissolved in 800 µl 0.1 M HEPES, pH 7.4, containing 0.1 M DTT. After 30 min at room temperature, DTT was removed from the peptide by gel filtration on a Sephadex G-25 column run in 25 mM HEPES, pH 7.4. The freshly reduced peptide was activated 2 with 2,2'-dipyridyldisulphide by first dissolving a five- fold molar excess of the reagent in 200 µl ethanol before addition to the pooled peptide fractions (fmal volume 2.2 ml). After 2 h at room temperature the peptide was again purified by gel filtration on a G-25 column. The eluted peptide was snap frozen and lyophilised. To 900 µl of a stirred solution of 4.0 mg/ml rFGF2/3 (210 µmol) in 25 mM citrate, pH 6, 80 mM NaCl, 1 mM EDTA, 56 nmol solid activated CL26 was added. The reaction was monitored by HPLC. After 30 min at room temperature an additional 56 nmol of peptide was added. This process was repeated twice until the final molar ratio of peptide:FGF was 5:4. After the reaction was complete free FGF and unreacted peptide were removed from the conjugate by ion exchange chromatography on SP-Sepharose. The fractions containing conjugate were identified by HPLC, pooled and desalted by gel filtration into 25 mM HEPES, pH 7.4. The final concentration of the conjugate was 0.8 mg/ml. The conjugate was greater than 90% pure as determined by HPLC. The mass of the conjugate was confirmed by MALDI-MS (observed: 21954; expected 21973). The conjugate was termed: FGF-CL26.

The polyLys peptide NBC28 has the sequence TK$_{18}$YCG (SEQ ID NO:10). NBC28 was prepared using the method described for NBC26 and was conjugated to rFGF using a method similar to that described above. The final concentration of the conjugage was 1.65 mg/ml. The conjugage was greater than 90% pure as determined by HPLC. The mass of the conjugage was confirmed by MALDI-MS (observed: 19879; expected 19853). The conjugage was termed: FGF-NBC28.

Transfection complexes between pCMVβ DNA and either FGF-CL26 or FGF-NBC28 were prepared at different charge ratios of peptide to DNA as described in the section entitled "Preparation of K6CL22-DNA complexes for PCS and Zeta analysis and transfection". The charge of rFGF was not taken into account. These complexes were tested for their ability to transfect BHK21 cells in vitro according to the method described in "transfection of cells". BHK21 cells (hamster kidney cells, A.T.C.C., CRL 8544).

Figure 31A:
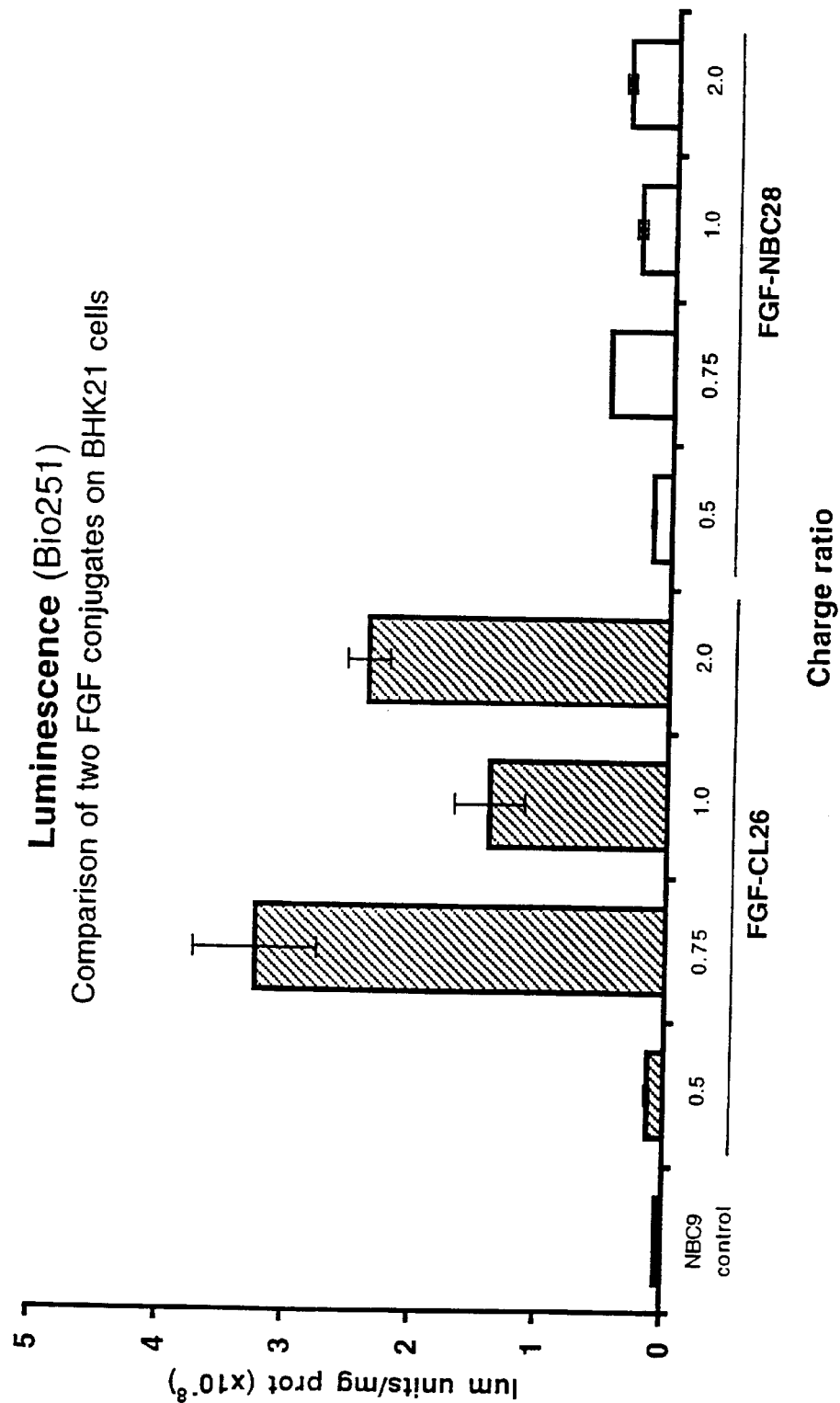
FIG. 31 shows luminescence and X-gal results of BHK21 cell transfection with FGF-peptide/DNA transfection complexes.
Figure 31B:
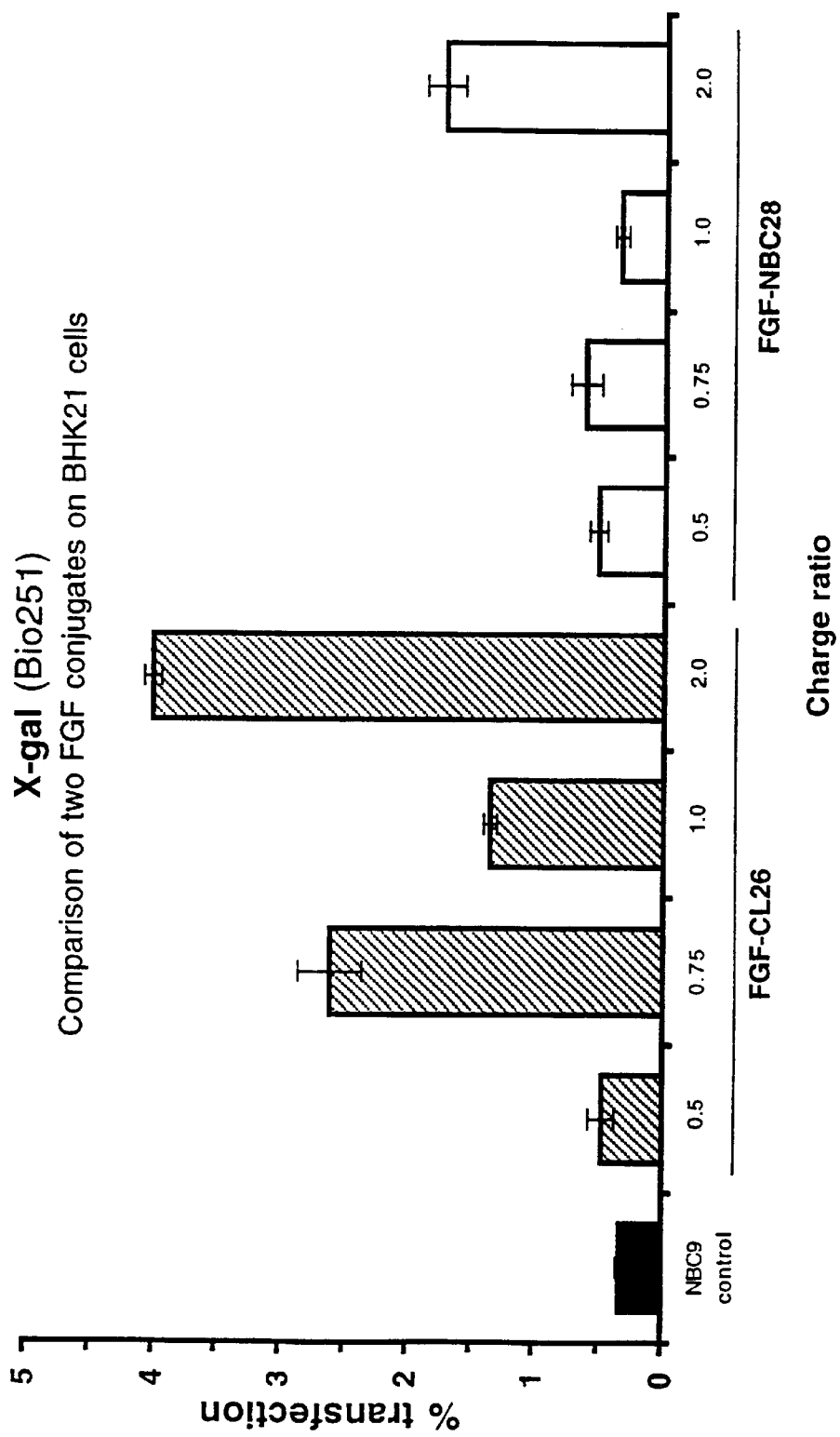

These data indicate that the transfection efficiency with FGF-CL26 is approximately 4–6 fold greater than with FGF-NBC28 (FIG. 31).

EXAMPLE 12

Figure 32A:
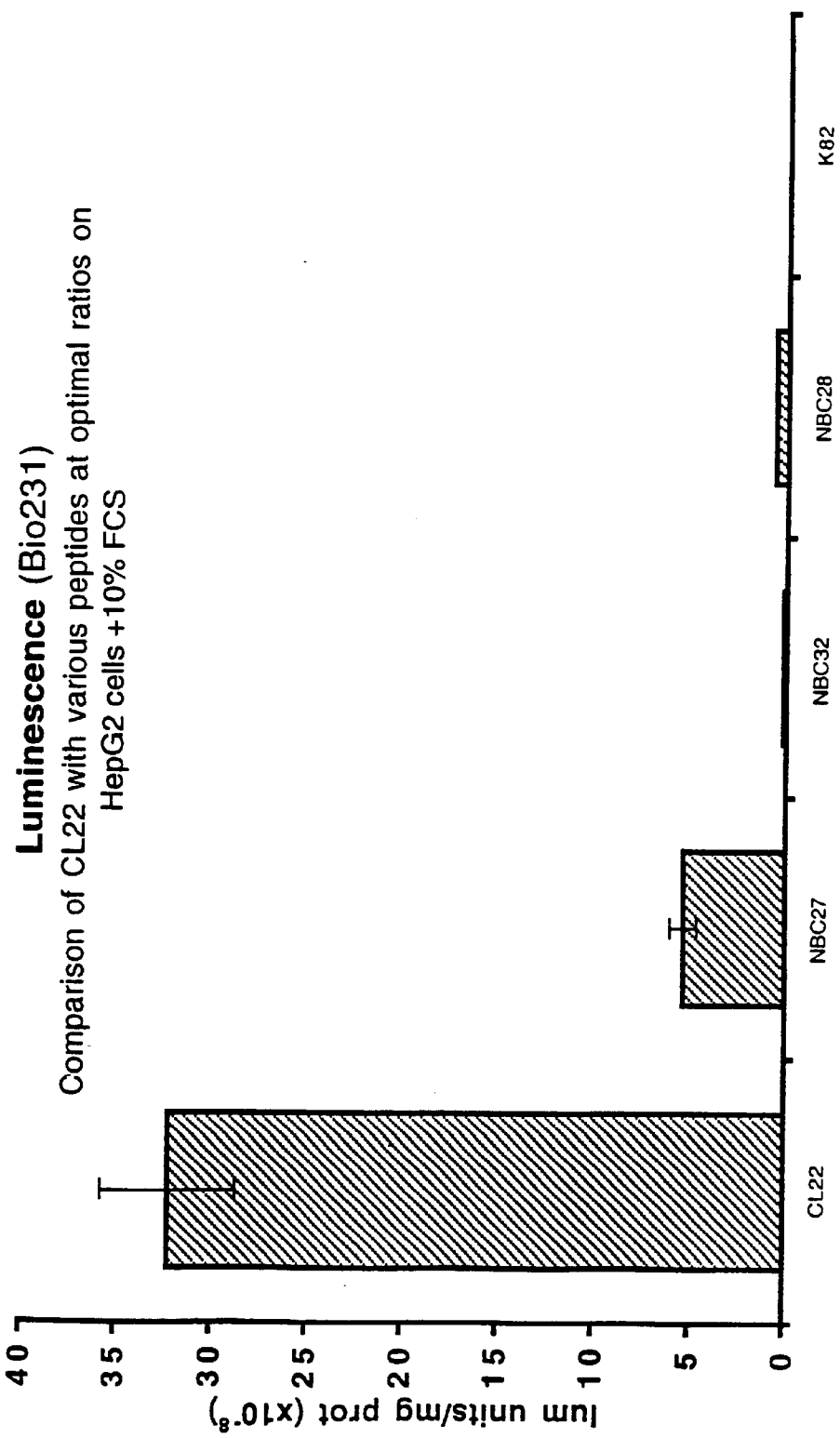
FIG. 32 shows the luminescence and X-gal results of HepG2 cell transfection with different peptide/DNA transfection complexes in the presence of FCS.

Transfection of HepG2 Cells with K6CL22/ DNA or Polylysine/DNA in the Presence of Serum K6CL22, NBC27 (a histone based peptide of sequence T[KKSPKKAKKPAA]$_2$KKSPKKAKKPAYCG) (SEQ ID NO:6), NBC32 (a polylysine peptide of sequence TK$_{36}$YCG) (SEQ ID NO:9), NBC28 (a polylysine based peptide of sequence TK$_{18}$ YCG) (SEQ ID NO:10) and K84 (polylysine of DP=84) were used to prepare transfection complexes at various optimum peptide to pCMVβ DNA charge ratios (the optimum charge ratio for each peptide transfection complex having previously been determined in a separate experiment on HepG2 cells in the presence of 10% FCS). These transfection complexes were then tested for their comparative ability to transfect HepG2 cells in the presence of 10% FCS (FIG. 32). The results indicate that transfection in the presence of 10% FCS is greater with transfection complexes prepared with K6CL22 than with polylysine peptides or a histone based peptide.

EXAMPLE 13

Transfection of Human Dendritic Cells with CL22 or CL26

Figure 33:
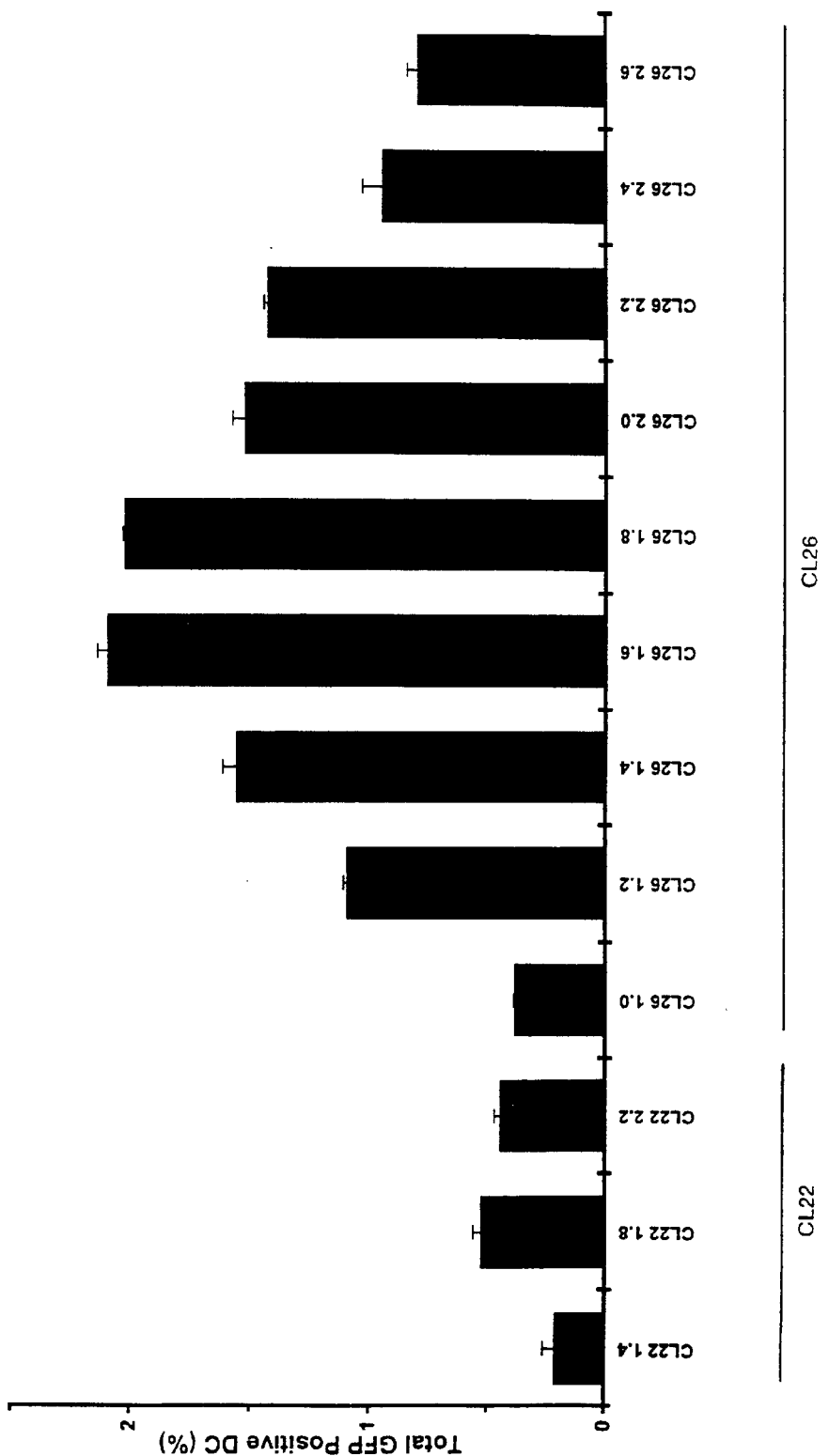
FIG. 33 shows results of transfection of dendritic cells with CL22 and CL26.
Figure 34:
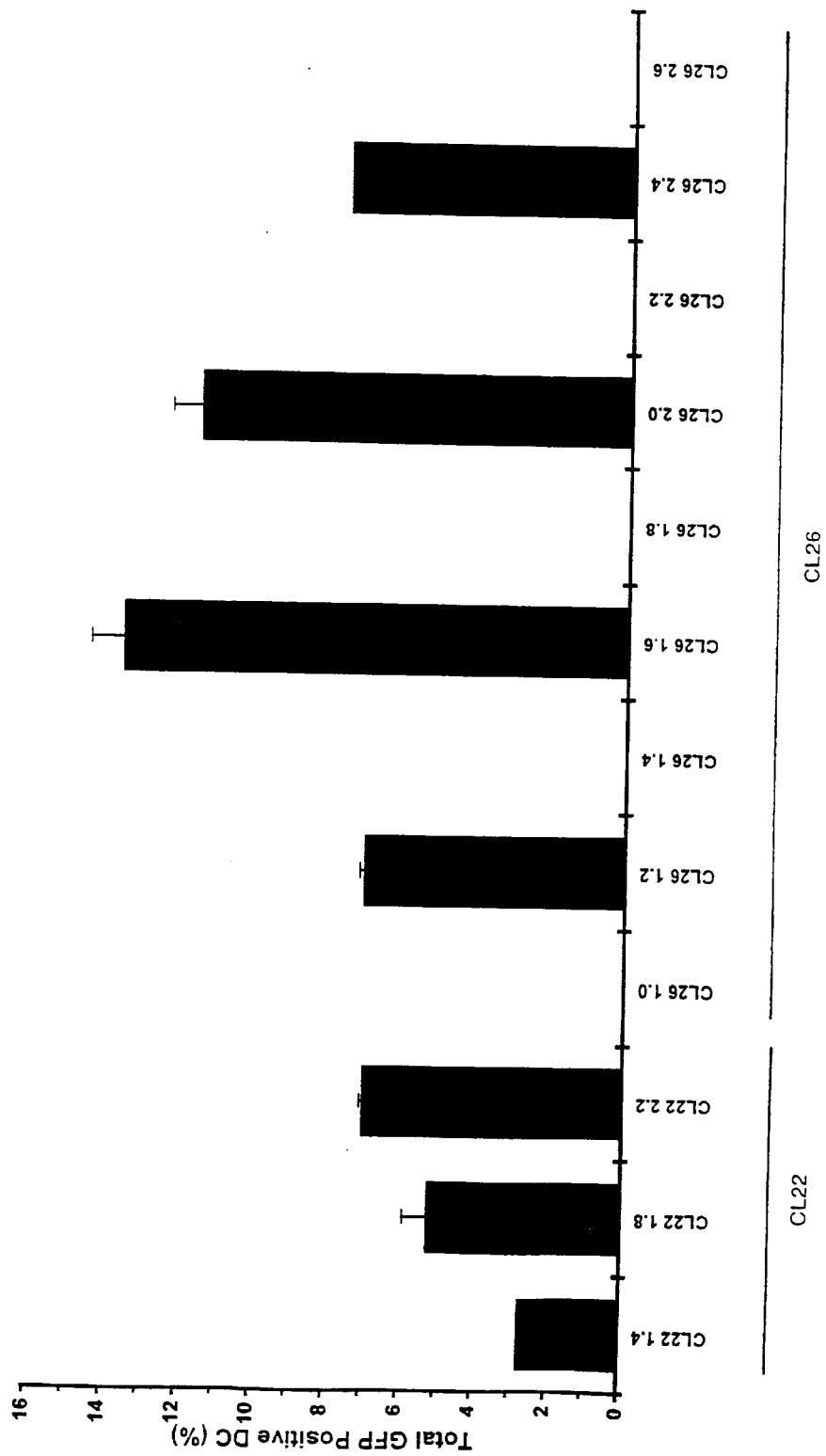
FIG. 34 shows results of transfection of dendritic cells with CL22 and CL26.
Figure 35:
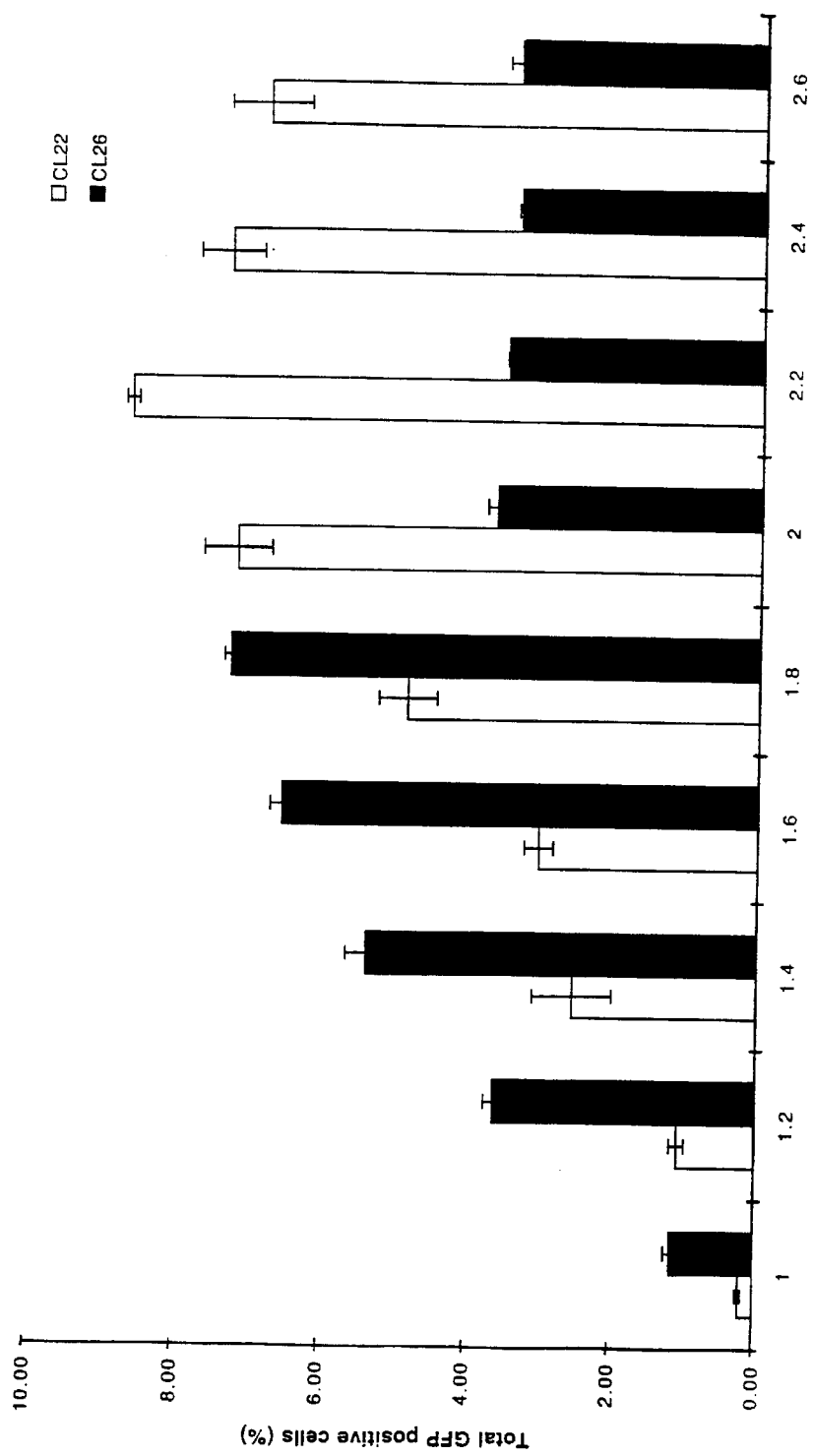
FIG. 35 shows results of transfection of dendritic cells with CL22 and CL26.

FIGS. 33–37 show comparisons of the transfection of dendritic cells with different polypeptides according to the invention. Dendritic cells were generated and transfected as described in Example 2. In the experiments described in this example, DNA (pEGFP-N1) was used at 1 µg. FIGS. 33–35 show results of transfections for three different preparations of dendritic cells in which the transfection efficiency with CL22-complexed DNA and CL26-complexed DNA was compared. In FIGS. 33 and 34, the peptide/DNA ratio was varied between 1.4 and 2.2 for CL22 and 1.0 and 2.6 for CL22. The optimal ratio is 1.6µg CL26:1 µg DNA for CL22 and is in the range of 1.6–2.2 µg CL22:1 µg DNA for CL22. These data demonstrate that dendritic cells are transfected at a higher efficiency with CL26-complexed DNA as compared to CL22-complexed DNA.

In FIG. 35 dendritic cells were transfected with either CL22-complexed DNA or CL26 complexed DNA. The peptide/DNA ratio was varied between 1.0 and 2.6. In this experiment, dendritic cells are transfected at a higher efficiency with CL26-complexed DNA as compared to CL22-complexed DNA when the peptide/DNA ratio is between 1 and 1.8. However, when the peptide/DNA ratio is between 2 and 2.6, the efficiency of transfection is greater with CL22-complexed DNA as compared to CL26-complexed DNA.

Figure 36:
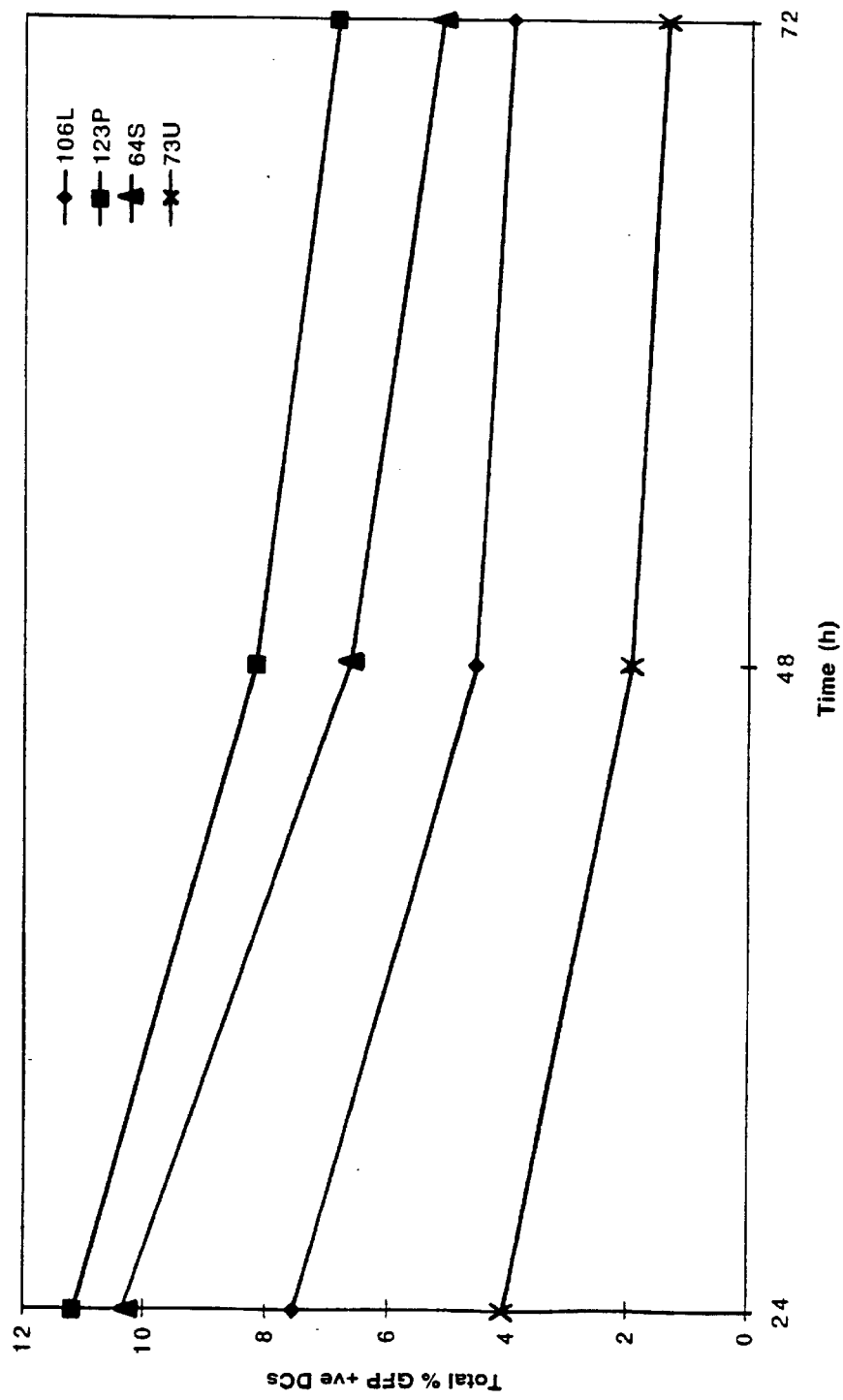
FIG. 36 is a comparison of the transfection efficiency of different preparations of CL22.

The variation in the relative ability of these two peptides to deliver DNA to dendritic cells can be explained, in part, by a variation in the transfection efficiency of different peptide preparations. FIG. 36 is a comparison of the transfection efficiency of different preparations of CL22 (designated as 108L, 123P, 64S and 73U. This figure demonstrates the variation in the transfection efficiency that is observed with different preparations of the CL22 peptide.

FIG. 37 compares the transfection efficiency of dendritic cells with CL22 in either monomeric (reduced) or dimeric (oxidized) form. Transfection results demonstrate that CL22 monomer transfects dendritic cells poorly compared with CL22 dimer when the peptide/DNA ratio is between 2.0 and 4.0. Dendritic cells are transfected at a higher efficiency with CL22 dimer as compared to CL22 monomer in the presence or absence of FCS although the transfection efficiency is greatly reduced in the presence of FCS as compared to in the absence of FCS.

Dosage, Therapeutic Use and Pharmaceutical Formulation

Polypeptides according to the invention and the nucleic acid to be delivered to cells may be formulated separately for parenteral administration or as the transfection complex. In the latter case the transfection complex may be assembled just prior to use. In the case of a pharmaceutical composition, the nucleic acid includes a gene whose expression would have some beneficial therapeutic effect on the cells of the recipient. For optimal efficiency of delivery of a therapeutic gene to a target cell, it is preferred that the therapeutic nucleic acid, in condensed formn, be less than about 100 nm, i.e., in the size range of approximately 1–100 nm, or less than AT approximately 50 kb in length. The nucleic acid may be in the form of plasmid DNA, either in linear or circular, or in the form of a DNA fragment.

Examples of therapeutic genes are well known in the art and include but are not limited to the β-glucocerebrosidase gene, the Bruton's thymidine kinase gene, genes encoding cytokines, such as TNF, interleukins 1–12, interferons (α, β,γ), F2 receptor, and T-cell receptor. The DNA may also include marker genes, such as drug resistance genes, the β-galactosidase gene, the dihydrofolate reductase gene, and the chloramphenicol acetyl transferase gene, genes encoding antigens, and genes encoding prodrug activating enzymes.

The peptides and DNA are exchanged into isotonic phosphate free buffer and sterile filtered through a 0.45 or 0.22 μm filter. The formulated solution or transfection complex (a mixture of the peptide conjugated to a selected functional group, DNA and free peptide) may be sterile filtered and aliquotted into suitable vials. The vials may be stored at 4° C., 2° C. or 80° C. or alternatively the DNA, peptide or transfection complex may be freeze dried from a buffer containing an appropriated carrier and bulking agent. In these cases, the dosage form is reconstituted with a sterile solution before administration. A pharmaceutical formulation according to the invention may include any physiologically compatible solution or diluent which contains less than 0.5% tissue culture serum, such as fetal or bovine calf serum.

Use of this type of pharmaceutical composition in vivo or ex vivo with a nucleic acid containing a gene of physiological importance, such as a gene that serves as a replacement for a defective gene or a gene with an additional potentially beneficial function, is expected to confer long term genetic modification of the cells and be effective in the treatment of disease.

For example, a patient that is subject to a viral or genetic disease may be treated in accordance with the invention via in vivo or ex vivo methods. For example in vivo treatments, a delivery vehicle of the invention can be administered to the patient, preferably in a biologically compatible solution or a pharmaceutically acceptable carrier, by ingestion, injection, inhalation or any number of other methods. The dosages administered will vary from patient to patient; a "therapeutically effective dose" will be determined by the level of enhancement of function of the transferred genetic material balanced against any risk or deleterious side effects. Monitoring levels of gene introduction, gene expression and/or the presence or levels of the encoded anti-viral protein will assist in selecting and adjusting the dosages administered. Generally, a composition including a transfection complex will be administered in a single dose in the range of 10 ng–100 μg/kg body weight, preferably in the range of 100 ng–10 μg/kg body weight, such that at least one copy of the therapeutic gene is delivered to each target cell. The therapeutic gene will, of course, be associated with appropriate regulatory sequences for expression of the gene in the target cell.

Ex vivo treatment is also contemplated within the present invention. Cell populations can be removed from the patient or otherwise provided, transduced with a therapeutic gene in accordance with the invention, then reintroduced into the patient. In general, ex vivo cell dosages will be determined according to the desired therapeutic effect balanced against any deleterious side-effects. Such dosages will usually be in the range of 10,000–100,000,000 cells per patient, daily weekly, or intermittently; preferably 1,000,000–10,000,000 cells per patient.

A complex according to the invention may be used to treat X-linked γ-globulinemia. The condensed nucleic acid in the transfection complex will contain the Bruton's tyrosine kinase gene (Vetrie et al., 1993, Nature 361:226–233), which is carried on a 2.1 kb fragment delineated by the PvuI site at position (+33) and the HindIII site at position (+2126). if desired, the plasmid also may include sequences which confer position independent, tissue specific gene expression, as taught in PCT/GB88/00655. The therapeutic gene may also encode a splice site and poly A tail, which may include portions of the human b globin locus splice and poly A signals; i.e., a BamHI XbaI 2.8 kb 3' splice/poly A flanking sequence containing exon 2 IVSII-exon 3 —polyA sequences.

A transfection complex containing the Bruton's tyrosine kinase gene is assembled as described herein and used to treat X-linked γ-globulinemia by introducing the construct directly into a patient for in vivo gene therapy or into pre-B cells for ex vivo therapy, as described in Martensson et al.; Eur. Jour. Immunol. (1987) 17:1499; Okabe et al., Eur. Jour. Immunol. (1992) 22:37; and Baneiji et al., Cell 33:729, 1983, and administering the transfected pre-B cells into a patient afflicted with X-linked γ-globulinemia. A transfection complex for treatment of X-linked γ-globulinemia will include a ligand for targeting of a preB cell. Such ligands are well-known in the art and will be specific for and capable of targeting one or more of the following cell surface markers: CD9, CD10, CD19, CD20, CD22, CD24, CD38, CD40, CD72, and CD74.

A transfection complex described herein also may be used for treatment of Gaucher's disease. Gaucher's disease stems from one of two different genetic mutations. Gaucher's type 1 is a CGG→>CAG mutation, which results in an Arg→>Gln substitution at position 119 of the β-glucocerebrosidase polypeptide (Graves, DNA 7:521, 1988). Gaucher's type 2 is a CTG—>CCG mutation, which results in a Leu—>Pro substitution at position 444 of the β-glucocerebrosidase polypeptide (Tsuji, NEJM 316:570, 1987). The presence of a β-glucocerebrosidase gene encoding a wild type polypeptide is believed to substantially correct Gaucher's disease. Therefore, a therapeutic nucleic acid useful according to the invention includes the β-glucocerebrosidase gene, as described in Horowitz et al., 1989, Genomics 4:87–96, which is carried, as disclosed in Horowitz et al., on a 9722 base pair fragment extending from a BaniHI site in exon 1 to an EcoRV site 31 to polyadenylation site. This fragment contains 11 exons and all intervening sequences, with translational start in exon 2. Sequences conferring position-independent and tissue-specific gene expression may be included in the construct and are carried on an 11.8 kb XhoI - Sacd fragment from the pIII.lyx construct as described in Bonifer et al., 1990, Euro. Mol. Biol. Org. Jour. 9:2843.

A transfection complex containing the p-glucocerebrosidase gene is assembled as described herein and used to treat Gaucher's disease by introducing the transfection complex directly into the host for in vivo treatment, or into isolated macrophages for ex vivo therapy, as described in Immunology and Cell Biology, 1993, 71:75–78 and introducing the transfected macrophages into a patient afflicted with Gaucher's disease. Expression of the wild type transgene in a patient afflicted with Gaucher's disease should result in correction of the diseased state. The transfection complex will contain a ligand that specifically targets a cell surface antigen on a macrophage. Such ligands are well-known in the art, for example, monoclonal antibody having specificity for and capable of targeting one or more of the following cell surface markers: CD14, CD16, CD26, CD31, CDw32, CD36, CD45RO, CD45RB, CD63, CD71, CD74, CD23, CD25 and CD69.

The cells targeted for in vivo or ex vivo gene transfer in accordance with the invention include any cells to which the delivery of the therapeutic gene is desired. Such cells will bear a cell surface marker for which a corresponding specific ligand is available or can be prepared to allow for cell-specific targeting according to the invention. For example, cells of the immune system such as T-cells, B-cells, and macrophages, hematopoietic cells, and dendritic cells have one or more well-known cell surface receptors having corresponding ligands which may be used as a targeting ligand in the transfection complex of the invention. Using established technologies, stem cells may be used for gene transfer after enrichment procedures (see, for example, European Patent Applications 0 455 482 and 0 451 611, which disclose methods for separating stem cells from a population of hematopoietic cells). Alternatively, unseparated hematopoietic cells and stem cell populations may be used as a target population for DNA transfer as described herein.

OTHER EMBODIMENTS

Other embodiments will be evident to those of skill in the art. It should be understood that the foregoing detailed description is provided for clarity only and is merely exemplary. The spirit and scope of the present invention are not limited to the above examples, but are encompassed by the following claims.

What is claimed is:

1. A polypeptide comprising the amino acid sequence NH2-KKKKKKGGFLGFWRGENGRKTRSAYERMCNILKGK-COOH (SEQ ID NO:1).

2. A compound having the following structure:

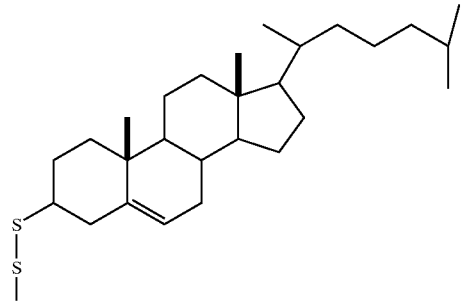

NH2-KKKKKKGGFLGFWRGENGRKTRSAYERMCNILKGK-COOH
(SEQ ID NO: 1).

3. A transfection complex comprising a polypeptide comprising the amino acid sequence NH2-KKKKKKGGFLGFWRGENGRKTRSAYERMCNILKGK-COOH (SEQ ID NO:1), and an isolated nucleic acid.

4. A transfection complex comprising a polypeptide having the following structure:

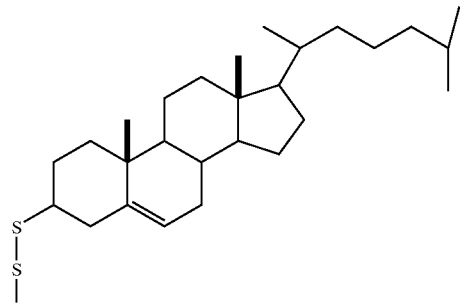

NH2-KKKKKKGGFLGFWRGENGRKTRSAYERMCNILKGK-COOH
(SEQ ID NO: 1), and an isolated nucleic acid.

5. A polypeptide comprising the amino acid sequence, from amino to carboxy termini, NH2-KKKKKKGGFLGFWRGENGRKTRSAYERMCNILKGK-COOH (SEQ ID NO: 1)
NH2-KKKKKKGGFLGFWRGENGRKTRSAYERMCNILKGK-COOH (SEQ ID NO: 1)

wherein S-S refers to a disulfide bond between each cysteine residue of the two peptides.

6. A polypeptide comprising the following amino acid sequence from amino to carboxy terminus:

H-KKKKKKKKKKKKGGFLGFWRGENGRKTRSAYERMCNILKGK-OH (CL26) (SEQ ID NO:3).

7. A dimerized CL26 polypeptide comprising the following amino acid sequence from amino to carboxy terminus:

H-KKKKKKKKKKKKGGFLGFWRGENGRKTRSAYERMCNILKGK-OH (SEQ ID NO: 3
H-KKKKKKKKKKKKGGFLGFWRGENGRKTRSAYERMCNILKGK-OH (SEQ ID NO: 3 wherein S-S refers to a disulfide bond between each cysteine residue of the two polypeptides.

8. A polypeptide comprising the amino acid sequence:

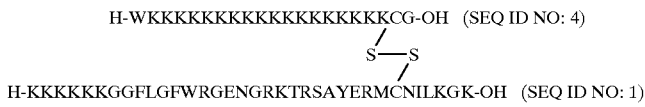

wherein S-S refers to a disulfide bond between each cysteine residue of the two polypeptides.

9. A transfection complex comprising a mixture of polypeptides, the mixture comprising the polypeptide of claim 1, 2, 5, 6, 7, or 8 and another polypeptide having a different sequence, and an isolated nucleic acid.

10. A formulation for transfection of cells, comprising the polypeptide of claim 1, 2, 5, 6, 7, or 8, an isolated nucleic acid, and an acceptable diluent.

11. The formulation of claim 10 wherein said polypeptide and said nucleic acid are associated such that said nucleic acid is condensed.

12. A method of transfecting a host cell comprising contacting said cell with the formulation of claim 11.

13. A method of transfecting a host cell comprising contacting said cell with the formulation of claim 10.

14. The method of claim 13, said host cell being a eukaryotic cell.

15. The method of claim 14, said host cell being a eukaryotic cell.

16. The method of claim 15, said eukaryotic cell being a mammalian cell.

17. The method of claim 16, said eukaryotic cell being a mammalian cell.

18. The method of claim 17, said mammalian cell being a human cell.

19. The method of claim 18, said mammalian cell being a human cell.

20. An improved method of delivering a nucleic acid to a cell wherein a nucleic acid delivery complex is administered to a patient, the improvement comprising wherein the delivery complex comprises a nucleic acid and a polypeptide comprising the polypeptide of claim 1, 2, 5, 6, 7, or 8.

21. A method of preparing a transfection complex, comprising contacting the polypeptide of claim 1, 2, 5, 6, 7, or 8 with a nucleic acid.

22. A transfection complex comprising a polypeptide comprising the amino acid sequence

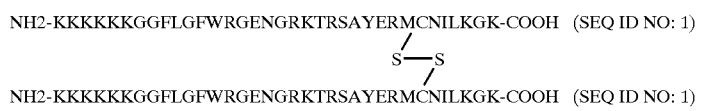

wherein S-S refers to a disulfide bond between each cysteine residue of the two peptides, and an isolated nucleic acid.

23. A transfection complex comprising the polypeptide: H-KKKKKKKKKKKKGGFLGFWRGENGRKTRS AYERMCNILKGK-OH (CL26) (SEQ ID NO:3), and an isolated nucleic acid.

24. A transfection complex comprising the polypeptides:

wherein S-S refers to a disulfide bond between each cysteine residue of the two polypeptides, and an isolated nucleic acid.

25. A transfection complex comprising the polypeptides:

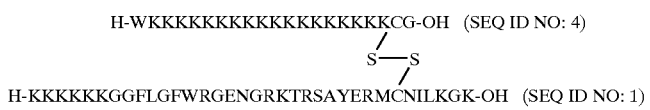

wherein S-S refers to a disulfide bond between each cysteine residue of the two polypeptides, and an isolated nucleic acid.

26. The transfection complex of claim 3, 4, 22, 23, 24, or 25 wherein said polypeptide and said nucleic acid are associated such that said nucleic acid is condensed.

27. A host cell containing the polypeptide of claim 1, 2, 5, 6, 7, or 8 or the transfection complex of claim 3, 4, 22, 23, 24, or 25.

28. A method of transfecting a host cell comprising contacting said cell with the transfection complex of claim 3, 4, 22, 23, 24, or 25.

29. The method of claim 28, said host cell being a eukaryotic cell.

30. The method of claim 29, said eukaryotic cell being a mammalian cell.

31. The method of claim 30, said mammalian cell being a human cell.

* * * * *

SEQUENCE LISTING

<160> NUMBER OF SEQ ID NOS: 10

<210> SEQ ID NO 1
<211> LENGTH: 35
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 1

Lys Lys Lys Lys Lys Lys Gly Gly Phe Leu Gly Phe Trp Arg Gly Glu
 1               5                  10                  15

Asn Gly Arg Lys Thr Arg Ser Ala Tyr Glu Arg Met Cys Asn Ile Leu
            20                  25                  30

Lys Gly Lys
        35

<210> SEQ ID NO 2
<211> LENGTH: 35
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 2

Lys Lys Lys Lys Lys Lys Gly Gly Phe Leu Gly Phe Asn Thr Lys Glu
 1               5                  10                  15

```
Arg Asn Leu Lys Arg Gly Trp Glu Ile Cys Arg Ser Ala Met Gly Tyr
            20                  25                  30

Gly Arg Lys
        35

<210> SEQ ID NO 3
<211> LENGTH: 41
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 3

Lys Lys Lys Lys Lys Lys Lys Lys Lys Lys Lys Gly Gly Phe Leu
 1               5                  10                  15

Gly Phe Trp Arg Gly Glu Asn Gly Arg Lys Thr Arg Ser Ala Tyr Glu
            20                  25                  30

Arg Met Cys Asn Ile Leu Lys Gly Lys
            35                  40

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 4

Trp Lys Lys Lys Lys Lys Lys Lys Lys Lys Lys Lys Lys Lys Lys
 1               5                  10                  15

Lys Lys Lys Cys Gly
            20

<210> SEQ ID NO 5
<211> LENGTH: 38
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 5

Thr Lys Lys Ser Pro Lys Lys Ala Lys Lys Pro Ala Ala Lys Lys Ser
 1               5                  10                  15

Pro Lys Lys Ala Lys Lys Pro Ala Ala Lys Lys Ser Pro Lys Lys Ala
            20                  25                  30

Lys Lys Pro Ala Ala Cys
        35

<210> SEQ ID NO 6
<211> LENGTH: 39
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 6

Thr Lys Lys Ser Pro Lys Lys Ala Lys Lys Pro Ala Ala Lys Lys Ser
 1               5                  10                  15

Pro Lys Lys Ala Lys Lys Pro Ala Ala Lys Lys Ser Pro Lys Lys Ala
            20                  25                  30
```

```
Lys Lys Pro Ala Tyr Cys Gly
        35

<210> SEQ ID NO 7
<211> LENGTH: 105
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 7
aaaaaaaaga aaaaaaaagg tggtttgctg ggtttctggc gtggtgaaaa cggtcgtaaa     60
acccgttctg cttacgaacg tatgtgcaac atcctgaaag gtaaa                   105

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 8

Gly Gly Gly Gly Gly Gly Phe Phe Leu Leu Trp Arg Arg Arg Glu
 1               5                  10                  15

Glu Asn Asn Lys Lys Lys Thr Ser Ala Tyr Met Cys Ile
             20                  25

<210> SEQ ID NO 9
<211> LENGTH: 40
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 9

Thr Lys Lys Lys Lys Lys Lys Lys Lys Lys Lys Lys Lys Lys Lys
 1               5                  10                  15

Lys Lys Lys Lys Lys Lys Lys Lys Lys Lys Lys Lys Lys Lys
             20                  25                  30

Lys Lys Lys Lys Lys Tyr Cys Gly
             35                  40

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 10

Thr Lys Lys Lys Lys Lys Lys Lys Lys Lys Lys Lys Lys Lys Lys
 1               5                  10                  15

Lys Lys Lys Tyr Cys Gly
             20
```